US012384780B2

(12) United States Patent
Dong et al.

(10) Patent No.: US 12,384,780 B2
(45) Date of Patent: Aug. 12, 2025

(54) PARP1 INHIBITORS AND USES THEREOF

(71) Applicant: XinThera, Inc., Foster City, CA (US)

(72) Inventors: Qing Dong, San Diego, CA (US);
Robert L. Hoffman, San Diego, CA (US); Stephen W. Kaldor, Foster City, CA (US); Joseph Robert Pinchman, San Diego, CA (US); Lynnie Trzoss, San Diego, CA (US); Porino Jinjo Va, San Diego, CA (US)

(73) Assignee: XinThera, Inc., Foster City, CA (US)

( * ) Notice: Subject to any disclaimer, the term of this patent is extended or adjusted under 35 U.S.C. 154(b) by 0 days.

(21) Appl. No.: 18/777,202

(22) Filed: Jul. 18, 2024

(65) Prior Publication Data

US 2024/0368162 A1 Nov. 7, 2024

Related U.S. Application Data

(63) Continuation of application No. 18/433,128, filed on Feb. 5, 2024, now abandoned, which is a continuation of application No. 18/099,770, filed on Jan. 20, 2023, now Pat. No. 11,939,329.

(60) Provisional application No. 63/376,338, filed on Sep. 20, 2022, provisional application No. 63/301,907, filed on Jan. 21, 2022.

(51) Int. Cl.
*C07D 471/04* (2006.01)
*C07D 401/12* (2006.01)

(52) U.S. Cl.
CPC ......... *C07D 471/04* (2013.01); *C07D 401/12* (2013.01); *C07B 2200/05* (2013.01)

(58) Field of Classification Search
CPC .................................................. C07D 471/04
See application file for complete search history.

(56) References Cited

U.S. PATENT DOCUMENTS

| | | | |
|---|---|---|---|
| 8,404,713 B2 | 3/2013 | Angibaud et al. |
| 8,541,417 B2 | 9/2013 | Brown et al. |
| 10,464,919 B2 | 11/2019 | Lee et al. |
| 11,325,906 B2 | 5/2022 | Johannes et al. |
| 11,591,331 B2 | 2/2023 | Trzoss et al. |
| 11,795,173 B1 | 10/2023 | Hoffman et al. |
| 11,802,128 B2 | 10/2023 | Hoffman et al. |
| 11,939,329 B2 | 3/2024 | Hoffman et al. |
| 12,006,322 B2 | 6/2024 | Hoffman et al. |
| 2021/0009577 A1 | 1/2021 | Lanman et al. |
| 2021/0040084 A1 | 2/2021 | Johannes et al. |
| 2022/0015338 A1 | 1/2022 | Zhang et al. |
| 2022/0348574 A1 | 11/2022 | Trzoss et al. |
| 2023/0128041 A1 | 4/2023 | Trzoss et al. |
| 2023/0159525 A1 | 5/2023 | Hoffman et al. |
| 2023/0203033 A1 | 6/2023 | Hoffman et al. |
| 2023/0234952 A1 | 7/2023 | Hoffman et al. |
| 2023/0348473 A1 | 11/2023 | Hoffman et al. |
| 2024/0109904 A1 | 4/2024 | Hoffman et al. |
| 2024/0174669 A1 | 5/2024 | Reddy et al. |
| 2024/0317746 A1 | 9/2024 | Liu et al. |
| 2024/0400569 A1 | 12/2024 | Hoffman et al. |

FOREIGN PATENT DOCUMENTS

| | | |
|---|---|---|
| AU | 2016276806 B2 | 2/2019 |
| CN | 115232129 A | 10/2022 |
| CN | 115403595 A | 11/2022 |
| CN | 116143776 A | 5/2023 |
| CN | 116535401 A | 8/2023 |
| CN | 116987066 A | 11/2023 |
| CN | 117017962 A | 11/2023 |
| CN | 117447449 A | 1/2024 |
| CN | 118084916 A | 5/2024 |
| JP | 2018-523679 | 8/2018 |
| JP | 2023-506368 | 2/2023 |
| WO | WO 2003/080581 A1 | 10/2003 |
| WO | WO 2009/053373 A1 | 4/2009 |
| WO | WO 2009/076512 A1 | 6/2009 |
| WO | WO 2010/085570 A1 | 7/2010 |
| WO | WO 2011/014681 A1 | 2/2011 |
| WO | WO 2014/064149 A1 | 5/2014 |
| WO | WO 2015/134973 A1 | 9/2015 |
| WO | WO 2016/107603 A1 | 7/2016 |
| WO | WO 2016/200101 A2 | 12/2016 |
| WO | WO 2020/098630 A1 | 5/2020 |
| WO | WO 2021/013735 A1 | 1/2021 |
| WO | WO 2021/260092 A1 | 12/2021 |
| WO | WO 2022/222921 A1 | 10/2022 |
| WO | WO 2022/222964 A1 | 10/2022 |
| WO | WO 2022/222965 A1 | 10/2022 |
| WO | WO 2022/222966 A1 | 10/2022 |
| WO | WO 2022/222995 A1 | 10/2022 |
| WO | WO 2022/223025 A1 | 10/2022 |
| WO | WO 2022/225934 A1 | 10/2022 |
| WO | WO 2022/228387 A1 | 11/2022 |
| WO | WO 2022/247816 A1 | 12/2022 |

(Continued)

OTHER PUBLICATIONS

WO 2023/046034 English translation, 2023.*
Boehler et al. Poly(ADP-ribose) polymerase 3 (PARP3), a newcomer in cellular response to DNA damage and mitotic progression. PNAS USA 108(7):2783-2788 (2011).
Co-pending U.S. Appl. No. 17/723,929, inventors Trzoss; Lynnie. et al., filed Apr. 19, 2022.
Co-pending U.S. Appl. No. 17/933,326, inventors Trzoss; Lynnie. et al., filed Sep. 19, 2022.
Co-pending U.S. Appl. No. 17/957,584, inventors Hoffman; Robert L. et al., filed Sep. 30, 2022.
Co-pending U.S. Appl. No. 18/099,770, inventors Hoffman; Robert L. et al., filed Jan. 20, 2023.
Co-pending U.S. Appl. No. 18/115,314, inventors Hoffman; Robert L. et al., filed Feb. 28, 2023.
Gill et al. The novel PARP1-selective inhibitor AZD5305 has reduced haematological toxicity when compared to PARP1/2 inhibitors in pre-clinical models. Poster# 1374 AACR 2021 Annual Apr. 10-19, 2020.

(Continued)

*Primary Examiner* — Brian E McDowell
(74) *Attorney, Agent, or Firm* — Sheppard Mullin Richter & Hampton LLP

(57) ABSTRACT

Described herein are PARP1 inhibitors and pharmaceutical compositions comprising said inhibitors. The subject compounds and compositions are useful for the treatment of cancer.

2 Claims, No Drawings

(56) References Cited

FOREIGN PATENT DOCUMENTS

| | | |
|---|---|---|
| WO | WO 2022/261777 A1 | 12/2022 |
| WO | WO 2023/025307 A1 | 3/2023 |
| WO | WO 2023/036285 A1 | 3/2023 |
| WO | WO 2023/046034 A1 | 3/2023 |
| WO | WO 2023/046149 A1 | 3/2023 |
| WO | WO 2023/046158 A1 | 3/2023 |
| WO | WO 2023/051716 A1 | 4/2023 |
| WO | WO 2023/051807 A1 | 4/2023 |
| WO | WO 2023/051812 A1 | 4/2023 |
| WO | WO 2023/056039 A1 | 4/2023 |
| WO | WO 2023/061406 A1 | 4/2023 |
| WO | WO 2023/088408 A1 | 5/2023 |
| WO | WO 2023/109521 A1 | 6/2023 |
| WO | WO 2023/133413 A1 | 7/2023 |
| WO | WO 2023/134647 A1 | 7/2023 |
| WO | WO 2023/138541 A1 | 7/2023 |
| WO | WO 2023/143236 A1 | 8/2023 |
| WO | WO 2023/144450 A1 | 8/2023 |
| WO | WO 2023/146294 A1 | 8/2023 |
| WO | WO 2023/146957 A1 | 8/2023 |
| WO | WO 2023/146960 A1 | 8/2023 |
| WO | WO 2023/147009 A1 | 8/2023 |
| WO | WO 2023/156386 A1 | 8/2023 |
| WO | WO 2023/169226 A1 | 9/2023 |
| WO | WO 2023/207283 A1 | 11/2023 |
| WO | WO 2023/207284 A1 | 11/2023 |
| WO | WO 2023/217045 A1 | 11/2023 |
| WO | WO 2023/227052 A1 | 11/2023 |
| WO | WO 2023/232069 A1 | 12/2023 |
| WO | WO 2024/041643 A1 | 2/2024 |
| WO | WO 2024/046366 A1 | 3/2024 |
| WO | WO 2024/046420 A1 | 3/2024 |
| WO | WO 2024/050370 A1 | 3/2024 |
| WO | WO2024/067691 A1 | 4/2024 |
| WO | WO2024/067694 A1 | 4/2024 |
| WO | WO2024/077137 A1 | 4/2024 |
| WO | WO2024/082654 A1 | 4/2024 |
| WO | WO2024/083201 A1 | 4/2024 |
| WO | WO2024/083211 A1 | 4/2024 |
| WO | WO2024/083218 A1 | 4/2024 |
| WO | WO2024/099364 A2 | 5/2024 |
| WO | WO2024/099416 A1 | 5/2024 |
| WO | WO2024/109871 A1 | 5/2024 |
| WO | WO2024/206172 A1 | 10/2024 |

OTHER PUBLICATIONS

Gozgit et al. PARP7 negatively regulates the type I interferon response in cancer cells and its inhibition triggers antitumor immunity. Cancer Cell 39(9):1214-1226 (2021).

Hande et al. Structure-based and property-based drug design of AZD5305, a highly selective PARP1 inhibitor and trapper. Poster #296 AACR 2021. Apr. 10-15, 2021.

Illuzzi et al. In vitro cellular profiling of AZD5305, novel PARP1-selective inhibitor and trapper. Poster #1272 AACR2021, Apr. 10-15, 2021.

Johannes et al., "Discovery of 5-{4-[(7-Ethyl-6-oxo-5,6-dihydro-1,5-naphthyridin-3-yl)methyl]piperazin-1-yl}-N-methylpyridine-2-carboxamide (AZD5305): A PARP1-DNA Trapper with High Selectivity for PARP1 over PARP2 and Other PARPs," Journal of Medicinal Chemistry, 2021, vol. 64, pp. 14498-14512.

Johannes et al. Discovery and first structural disclosure of AZD5305, a next generation, highly selective PARP1 inhibitor and trapper. AstraZeneca—AZD5305—a best in class highly selective PARP1 inhibitor. Presentation at AACR 2021 Apr. 10, 2021.

Krug et al., "Inhibition of host PARP1 contributes to the anti-inflammatory and antitubercular activity of pyrazinamide," Nature Communications, Dec. 2023, 15 pages.

Kulak et al. Disruption of Wnt/β-Catenin Signaling and Telomeric Shortening Are Inextricable Consequences of Tankyrase Inhibition in Human Cells. Mol Cell Biol. 35(14):2425-2435 (2015).

PCT/US2022/025357 International Search Report and Written Opinion dated Jun. 30, 2022.

PCT/US2022/045415 International Search Report and Written Opinion dated Nov. 25, 2022.

PCT/US2023/011268 International Search Report and Written Opinion dated Apr. 4, 2023.

PCT/US2023/011609 International Search Report and Written Opinion dated Mar. 29, 2023.

PCT/US2023/011613 International Search Report and Written Opinion dated Apr. 11, 2023.

PCT/US2023/076075 International Search Report and Written Opinion dated Jan. 25, 2024.

Ren et al. Synthesis and in vitro biological evaluation of 3-ethyl-1,5-naphthyridin-2 (1H)-one derivatives as potent PARP-1 selective inhibitors and PARP-1 DNA trappers. Bioorg Med Chem Lett. 129046 (2022).

Staniszewska et al. The novel PARP1-selective inhibitor, AZD5305, is efficacious as monotherapy and in combination with standard of care chemotherapy in in vivo preclinical models. Poster#1270 AACR 2021. Apr. 10-15, 2021 and May 17-21.

U.S. Appl. No. 17/957,584 Office Action dated Feb. 15, 2023.

U.S. Appl. No. 18/099,770 Office Action dated Apr. 26, 2023.

U.S. Appl. No. 18/115,314 Office Action dated May 30, 2023.

Vermehren-Schmaedick et al. Characterization of PARP6 Function in Knockout Mice and Patients with Developmental Delay. Cells 10(6):1289 (2021).

Vyas et al. A Systematic Analysis of the PARP Protein Family Identifies New Functions Critical for Cell Physiology. Nat. Commun. 4(1):2240 (2013).

Yu et al. PARP-10, a novel Myc-interacting protein with poly(ADP-ribose) polymerase activity, inhibits transformation. Oncogene 24:1982-1993 (2005).

Loryan et al. "Unbound Brain-to-Plasma Partition Coefficient, $K_{p,uu,brain}$-a Game Changing Parameter for CNS Drug Discovery and Development", Pharmaceutical Research (2022) 39: 1321-1341.

Zefirova et al. "About the History and Development of the Concept of Bioisosterism", Bulletin of Moscow University. SER.2. Chemistry. 2002, vol. 43, No. 4, 14 pages with English translation.

* cited by examiner

PARP1 INHIBITORS AND USES THEREOF

CROSS-REFERENCE

This application is a continuation of U.S. patent application Ser. No. 18/433,128 filed Feb. 5, 2024, which is a continuation of U.S. patent application Ser. No. 18/099,770 filed Jan. 20, 2023, now U.S. Pat. No. 11,939,329, which claims the benefit of U.S. Provisional Application Ser. No. 63/301,907 filed Jan. 21, 2022 and U.S. Provisional Application Ser. No. 63/376,338 filed Sep. 20, 2022, each of which are hereby incorporated by reference in their entirety.

BACKGROUND OF THE INVENTION

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut, and skeletal muscle. Inhibitors have been efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors have also shown benefit in several models of degenerative disease including diabetes (as well as complications) and Parkinson's disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

PARP1 and PARP2 are the most extensively studied PARPs for their role in DNA damage repair. PARP1 is activated by DNA damage breaks and functions to catalyze the addition of poly (ADP-ribose) (PAR) chains to target proteins. This post-translational modification, known as PARylation, mediates the recruitment of additional DNA repair factors to DNA lesions.

Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy.

Inhibition of PARP family enzymes has been exploited as a strategy to selectively kill cancer cells by inactivating complementary DNA repair pathways. A number of preclinical and clinical studies have demonstrated that tumor cells bearing deleterious alterations of BRCA1 or BRCA2, key tumor suppressor proteins involved in double-strand DNA break (DSB) repair by homologous recombination (HR), are selectively sensitive to small molecule inhibitors of the PARP family of DNA repair enzymes. Such tumors have deficient homologous recombination repair (HRR) pathways and are dependent on PARP enzymes function for survival. Although PARP inhibitor therapy has predominantly targeted SRCA-mutated cancers, PARP inhibitors have been tested clinically in non-SRCA-mutant tumors, those which exhibit homologous recombination deficiency (HRD).

It is believed that PARP inhibitors having improved selectivity for PARP1 may possess improved efficacy and reduced toxicity compared to other clinical PARP1/2 inhibitors. It is believed also that selective strong inhibition of PARP1 would lead to trapping of PARP1 on DNA, resulting in DNA double strand breaks (DSBs) through collapse of replication forks in S-phase. It is believed also that PARP1-DNA trapping is an effective mechanism for selectively killing tumor cells having HRD. An unmet medical need therefore exists for effective and safe PARP inhibitors. Especially PARP inhibitors having selectivity for PARP1.

SUMMARY OF THE INVENTION

Disclosed herein is a compound of Formula (I), or a pharmaceutically acceptable salt, solvate, or stereoisomer thereof:

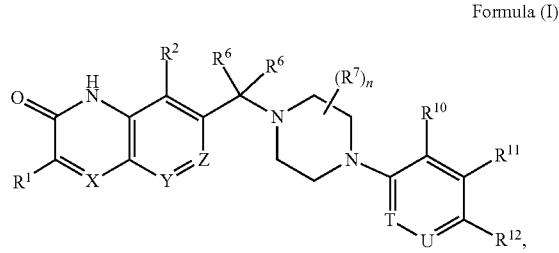

Formula (I)

wherein:
$R^1$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^2$ is hydrogen, deuterium, halogen, —CN, —OR$^a$, —NR$^c$R$^d$, $C_1$-$C_6$alkyl, $C_1$-$C_6$haloalkyl, or $C_1$-$C_6$deuteroalkyl;

X is N or CR$^3$;
Y is N or CR$^4$;
Z is N or CR$^5$;

$R^3$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^4$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^5$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

each $R^6$ is independently hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; wherein the alkyl, cycloalkyl, and heterocycloalkyl is optionally substituted with one or more R;

or two $R^6$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^7$ is independently deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, or $C_2$-$C_6$alkynyl;

or two $R^7$ on the same carbon are taken together to form an oxo;

or two $R^7$ on the same carbon or different carbons are taken together to form a cycloalkyl or heterocycloalkyl; each optionally substituted with one or more R;

n is 0-4;

T is N or CR$^B$;

U is N or CR$^9$;

$R^8$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^9$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^{10}$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^{11}$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^{12}$ is cyano or halogen;

each R$^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently optionally substituted with one or more R;

each R$^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently optionally substituted with one or more R; and each R$^c$ and R$^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently optionally substituted with one or more R;

or R$^c$ and R$^d$ are taken together with the atom to which they are attached to form a heterocycloalkyl optionally substituted with one or more R;

each R is independently deuterium, halogen, —CN, —OH, —OC$_1$-C$_6$alkyl, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(=O)NHC$_1$-C$_6$alkyl, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or two R on the same atom are taken together to form an oxo;

provided that when X is CR$^3$, Y is CR$^4$, and Z is CR$^5$; then one of R$^3$, R$^4$, and R$^5$ is not hydrogen and R$^4$ is not —OMe; and provided that when X is CH, Y is CH, and Z is CH; then R$^2$ is not hydrogen.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating a cancer comprising a BRCA1 and/or a BRCA2 mutation in a subject in need thereof, the method comprising administering a compound disclosed herein, or a pharmaceutically acceptable salt, solvate, or stereoisomer thereof. Also disclosed herein is a method of treating a cancer comprising a mutation in a gene conferring homologous repair deficiency in a subject in need thereof, the method comprising administering a compound disclosed herein, or a pharmaceutically acceptable salt, solvate, or stereoisomer thereof. In some embodiments, the mutation in a gene conferring homologous repair deficiency comprises ATM, BRCA1, BRCA2, BARD1, BRIP1, CDK12, CHEK1, CHEK2, FANCL, PALB2, RAD51B, RAD51C, RAD51D, or RAD54L, or any combinations thereof. In some embodiments, the cancer is bladder cancer, brain & CNS cancer, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer. In some embodiments, the cancer is metastatic cancer. In some embodiments, the cancer has metastasized in the brain.

Also disclosed herein is a method of treating a cancer that is present in the brain in a subject in need thereof, the method comprising administering a compound disclosed herein, or a pharmaceutically acceptable salt, solvate, or stereoisomer thereof.

Also disclosed herein is a method of treating brain cancer in a subject in need thereof, the method comprising administering a compound disclosed herein, or a pharmaceutically acceptable salt, solvate, or stereoisomer thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms (C$_3$-C$_{15}$ cycloalkyl or C$_3$-C$_{15}$ cycloalkenyl), from three to ten carbon atoms (C$_3$-C$_{10}$ cycloalkyl or C$_3$-C$_{10}$ cycloalkenyl), from three to eight carbon atoms (C$_3$-C$_8$ cycloalkyl or C$_3$-C$_8$ cycloalkenyl), from three to six carbon atoms (C$_3$-C$_6$ cycloalkyl or C$_3$-C$_6$ cycloalkenyl), from three to five carbon atoms (C$_3$-C$_5$ cycloalkyl or C$_3$-C$_5$ cycloalkenyl), or three to four carbon atoms (C$_3$-C$_4$ cycloalkyl or C$_3$-C$_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through anon-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-$C_{15}$ heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or $C_2$-$C_7$ heterocycloalkenyl), from two to six carbon atoms ($C_2$-$C_6$ heterocycloalkyl or $C_2$-$C_6$ heterocycloalkenyl), from two to five carbon atoms ($C_2$-$C_5$ heterocycloalkyl or $C_2$-$C_5$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

The terms "treat," "treated," "treatment," or "treating" as used herein refers to therapeutic treatment, wherein the object is to slow (lessen) an undesired physiological condition, disorder, or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. The terms "treat," "treated," "treatment," or "treating" as well as words stemming therefrom, as used herein, do not necessarily imply 100% or complete treatment. Rather, there are varying degrees of treatment of which one of ordinary skill in the art recognizes as having a potential benefit or therapeutic effect. In this respect, the disclosed methods can provide any amount of any level of treatment of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. "Synergy" or "synergize" refers to an effect of a combination that is greater than additive of the effects of each component alone at the same doses.

As used herein, a "disease or disorder associated with PARP" or, alternatively, "a PARP-mediated disease or disorder" means any disease or other deleterious condition in which PARP, or a mutant thereof, is known or suspected to play a role.

As used herein, a "disease or disorder associated with PARP1" or, alternatively, "a PARP1-mediated disease or disorder" means any disease or other deleterious condition in which PARP1, or a mutant thereof, is known or suspected to play a role.

Compounds

Described herein are compounds, or a pharmaceutically acceptable salt, solvate, or stereoisomer thereof useful in the treatment of cancer.

Disclosed herein is a compound of Formula (I), or a pharmaceutically acceptable salt, solvate, or stereoisomer thereof:

Formula (I)

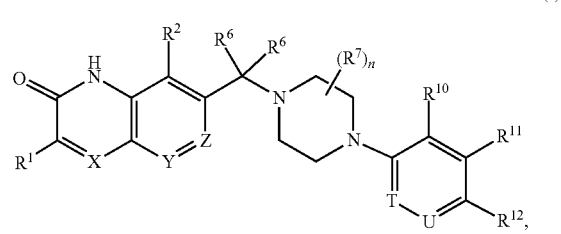

wherein:
R$^1$ is hydrogen, deuterium, halogen, —CN, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein the alkyl, alkenyl, alkynyl, cycloalkyl, and heterocycloalkyl is optionally substituted with one or more R;

$R^2$ is hydrogen, deuterium, halogen, —CN, —OR$^a$, —NR$^c$R$^d$, $C_1$-$C_6$alkyl, $C_1$-$C_6$haloalkyl, or $C_1$-$C_6$deuteroalkyl;

X is N or CR$^3$;

Y is N or CR$^4$;

Z is N or CR$^5$;

$R^3$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^4$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^5$ is hydrogen, deuterium, halogen, —CN, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

each $R^6$ is independently hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; wherein the alkyl, cycloalkyl, and heterocycloalkyl is optionally substituted with one or more R;

or two $R^6$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^7$ is independently deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, or $C_2$-$C_6$alkynyl;

or two $R^7$ on the same carbon are taken together to form an oxo;

or two $R^7$ on the same carbon or different carbons are taken together to form a cycloalkyl or heterocycloalkyl; each optionally substituted with one or more R;

n is 0-4;

T is N or CR;

U is N or CR$^9$;

$R^8$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^9$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^{10}$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^{11}$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^{12}$ is cyano or halogen;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently optionally substituted with one or more R; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R;

each R is independently deuterium, halogen, —CN, —OH, —OC$_1$-$C_6$alkyl, —NH$_2$, —NHC$_1$-$C_6$alkyl, —N(C$_1$-$C_6$alkyl)$_2$, —NHC(=O)OC$_1$-$C_6$alkyl, —C(=O)C$_1$-$C_6$alkyl, —C(=O)OH, —C(=O)OC$_1$-$C_6$alkyl, —C(=O)NH$_2$, —C(=O)N(C$_1$-$C_6$alkyl)$_2$, —C(=O)NHC$_1$-$C_6$alkyl, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two R on the same atom are taken together to form an oxo;

provided that when X is CR$^3$, Y is CR$^4$, and Z is CR$^5$; then one of R$^3$, R$^4$, and R$^5$ is not hydrogen and R$^4$ is not —OMe; and provided that when X is CH, Y is CH, and Z is CH; then R$^2$ is not hydrogen.

In some embodiments of a compound of Formula (I), the compound is not 7-(1-(4-(2,4-difluorophenyl)piperazin-1-yl)ethyl)-3-methylquinolin-2(1H)-one.

In some embodiments of a compound of Formula (I), the compound is not 7-((4-(3,4-dichlorophenyl)piperazin-1-yl)methyl)-3-ethylquinolin-2(1H)-one.

In some embodiments of a compound of Formula (I), the compound is not 7-((5-(4-chlorophenyl)-2,5-diazabicyclo[2.2.1]heptan-2-yl)methyl)-3-ethylquinolin-2(1H)-one.

In some embodiments of a compound of Formula (I), the compound is not 6-(4-(cyclohexyl(3-methyl-2-oxo-1,2-dihydroquinolin-7-yl)methyl)piperazin-1-yl)nicotinonitrile.

In some embodiments of a compound of Formula (I), the compound is not 6-(4-((3-ethyl-5-methoxy-2-oxo-1,2-dihydroquinolin-7-yl)methyl)piperazin-1-yl)nicotinonitrile.

In some embodiments of a compound of Formula (I), the compound is not 6-(4-(2-methyl-1-(3-methyl-2-oxo-1,2-dihydroquinolin-7-yl)propyl)piperazin-1-yl)nicotinonitrile.

In some embodiments of a compound of Formula (I), the compound is not 6-(4-((3-ethyl-2-oxo-1,2-dihydroquinolin-7-yl)methyl)piperazin-1-yl)nicotinonitrile.

In some embodiments of a compound of Formula (I), the compound is not 6-(4-(1-(3-ethyl-2-oxo-1,2-dihydroquinolin-7-yl)-2-methylpropyl)piperazin-1-yl)nicotinonitrile.

In some embodiments of a compound of Formula (I), X is N. In some embodiments of a compound of Formula (I), X is $CR^3$.

In some embodiments of a compound of Formula (I), Y is N. In some embodiments of a compound of Formula (I), Y is $CR^4$.

In some embodiments of a compound of Formula (I), Z is N. In some embodiments of a compound of Formula (I), Z is $CR^5$.

In some embodiments of a compound of Formula (I), X is N; Y is N or $CR^4$; and Z is N or $CR^5$. In some embodiments of a compound of Formula (I), X is N or $CR^3$; Y is N; and Z is N or $CR^5$. In some embodiments of a compound of Formula (I), X is N or $CR^3$; Y is N or $CR^4$; and Z is N. In some embodiments of a compound of Formula (I), one of X, Y, or Z is N. In some embodiments of a compound of Formula (I), two of X, Y, or Z are N. In some embodiments of a compound of Formula (I), X is $CR^3$; Y is $CR^4$; and Z is $CR^5$. In some embodiments of a compound of Formula (I), X is CH; Y is CH; and Z is CH. In some embodiments of a compound of Formula (I), X is $CR^3$; Y is N; and Z is $CR^5$. In some embodiments of a compound of Formula (I), X is CH; Y is N; and Z is CH. In some embodiments of a compound of Formula (I), X is N; Y is $CR^4$; and Z is $CR^5$. In some embodiments of a compound of Formula (I), X is N; Y is CH; and Z is CH.

In some embodiments of a compound of Formula (I), the compound is of Formula (Ia):

Formula (Ia)

In some embodiments of a compound of Formula (I), the compound is of Formula (Ib):

Formula (Ib)

In some embodiments of a compound of Formula (I), the compound is of Formula (Ic):

Formula (Ic)

In some embodiments of a compound of Formula (I), the compound is of Formula (Id):

Formula (Id)

wherein one of $R^3$, $R^4$, and $R^5$ is not hydrogen and $R^4$ is not —OMe.

In some embodiments of a compound of Formula (I), the compound is of Formula (Ie):

Formula (Ie)

wherein $R^2$ is deuterium, halogen, —CN, —$OR^a$, —$NR^cR^d$, $C_1$-$C_6$alkyl, $C_1$-$C_6$haloalkyl, or $C_1$-$C_6$deuteroalkyl.

In some embodiments of a compound of Formula (I) or (Ia)-(Ie), $R^1$ is hydrogen, deuterium, halogen, —CN, —$OR^a$, —$NR^cR^d$, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R.

In some embodiments of a compound of Formula (I) or (Ia)-(Ie), $R^1$ is hydrogen, deuterium, halogen, $C_1$-$C_6$alkyl, $C_1$-$C_6$haloalkyl, $C_1$-$C_6$deuteroalkyl, $C_2$-$C_6$alkynyl, cycloalkyl, or heterocycloalkyl; wherein the alkyl, alkynyl, cycloalkyl, and heterocycloalkyl is optionally substituted with one or more R. In some embodiments of a compound of Formula (I) or (Ia)-(Ie), $R^1$ is hydrogen, deuterium, halogen, $C_1$-$C_6$alkyl, $C_1$-$C_6$haloalkyl, $C_2$-$C_6$alkynyl, cycloalkyl, or heterocycloalkyl; wherein the alkyl, alkynyl, cycloalkyl, and heterocycloalkyl is optionally substituted with one or more R. In some embodiments of a compound of Formula (I) or (Ia)-(Ie), $R^1$ is halogen, $C_1$-$C_6$alkyl, $C_1$-$C_6$haloalkyl, $C_2$-$C_6$alkynyl, or cycloalkyl; wherein the alkyl, alkynyl, and cycloalkyl is optionally substituted with one or more R. In some embodiments of a compound of Formula (I) or (Ia)-(Ie), $R^1$ is halogen, $C_1$-$C_6$alkyl, $C_1$-$C_6$haloalkyl, $C_2$-$C_6$alkynyl, or cycloalkyl. In some embodiments of a compound of Formula (I) or (Ia)-(Ie), $R^1$ is $C_1$-$C_6$alkyl, $C_1$-$C_6$haloalkyl, $C_2$-$C_6$alkynyl, or cycloalkyl. In some embodiments of a compound of Formula (I) or (Ia)-(Ie), $R^1$ is $C_1$-$C_6$alkyl or cycloalkyl. In some embodiments of a compound of Formula (I) or (Ia)-(Ie), $R^1$ is $C_1$-$C_6$alkyl. In some embodiments of a compound of Formula (I) or (Ia)-(Ie), $R^1$ is methyl or ethyl. In some embodiments of a compound of Formula (I) or (Ia)-(Ie), $R^1$ is methyl. In some embodiments of a compound of Formula (I) or (Ia)-(Ie), $R^1$ is ethyl. In some embodiments of a compound of Formula (I) or (Ia)-(Ie), $R^1$ is cycloalkyl. In some embodiments of a compound of Formula (I) or (Ia)-(Ie), $R^1$ is cyclopropyl. In some embodiments of a compound of Formula (I) or (Ia)-(Ie), $R^1$ is heterocycloalkyl. In some embodiments of a compound of Formula (I) or (Ia)-(Ie), $R^1$ is $C_1$-$C_6$haloalkyl. In some embodiments of a compound of Formula (I) or (Ia)-(Ie), $R^1$ is difluoromethyl. In some embodiments of a compound of Formula (I) or (Ia)-(Ie), $R^1$ is halogen, $C_1$-$C_6$haloalkyl, or cycloalkyl. In some embodiments of a compound of Formula (I) or (Ia)-(Ie), $R^1$ is halogen or cycloalkyl. In some embodiments of a compound of Formula (I) or (Ia)-(Ie), $R^1$ is halogen. In some embodiments of a compound of Formula (I) or (Ia)-(Ie), $R^1$ is fluoro or chloro. In some embodiments of a compound of Formula (I) or (Ia)-(Ie), $R^1$ is chloro.

In some embodiments of a compound of Formula (I) or (Ia)-(Ie), $R^2$ is hydrogen, deuterium, halogen, —$OR^a$, $C_1$-$C_6$alkyl, or $C_1$-$C_6$haloalkyl. In some embodiments of a compound of Formula (I) or (Ia)-(Ie), $R^2$ is hydrogen, halogen, —$OR^a$, or $C_1$-$C_6$alkyl. In some embodiments of a compound of Formula (I) or (Ia)-(Ie), $R^2$ is hydrogen or halogen. In some embodiments of a compound of Formula (I) or (Ia)-(Ie), $R^2$ is halogen. In some embodiments of a compound of Formula (I) or (Ia)-(Ie), $R^2$ is fluoro. In some embodiments of a compound of Formula (I) or (Ia)-(Ie), $R^2$ is methyl. In some embodiments of a compound of Formula (I) or (Ia)-(Ie), $R^2$ is —$OR^a$. In some embodiments of a compound of Formula (I) or (Ia)-(Ie), $R^2$ is —$OCF_3$. In some embodiments of a compound of Formula (I) or (Ia)-(Ie), $R^2$ is hydrogen, deuterium, halogen, —CN, —$OR^a$, —$NR^cR^d$, $C_1$-$C_2$alkyl, $C_1$-$C_2$haloalkyl, or $C_1$-$C_2$deuteroalkyl. In some embodiments of a compound of Formula (I) or (Ia)-(Ie), $R^2$ is hydrogen, halogen, —$OR^a$, or $C_1$-$C_2$alkyl. In some embodiments of a compound of Formula (I) or (Ia)-(Ie), $R^2$ is halogen, —$OR^a$, or $C_1$-$C_2$alkyl. In some embodiments of a compound of Formula (I) or (Ia)-(Ie), $R^2$ is halogen or $C_1$-$C_2$alkyl.

In some embodiments of a compound of Formula (I) or (Ia)-(Ie), $R^3$ is hydrogen, deuterium, halogen, —$OR^a$, $C_1$-$C_6$alkyl, $C_1$-$C_6$haloalkyl, or $C_1$-$C_6$deuteroalkyl. In some embodiments of a compound of Formula (I) or (Ia)-(Ie), $R^3$ is hydrogen, halogen, —$OR^a$, or $C_1$-$C_6$alkyl. In some embodiments of a compound of Formula (I) or (Ia)-(Ie), $R^3$ is hydrogen, or halogen, or $C_1$-$C_6$alkyl.

In some embodiments of a compound of Formula (I) or (Ia)-(Ie), $R^3$ is hydrogen or halogen.

In some embodiments of a compound of Formula (I) or (Ia)-(Ie), $R^3$ is halogen. In some embodiments of a compound of Formula (I) or (Ia)-(Ie), $R^3$ is hydrogen. In some embodiments of a compound of Formula (I) or (Ia)-(Ie), $R^3$ is not hydrogen.

In some embodiments of a compound of Formula (I) or (Ia)-(Ie), $R^4$ is hydrogen, deuterium, halogen, —CN, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R. In some embodiments of a compound of Formula (I) or (Ia)-(Ie), $R^4$ is hydrogen, deuterium, halogen, —$OR^a$, $C_1$-$C_6$alkyl, $C_1$-$C_6$haloalkyl, or $C_1$-$C_6$deuteroalkyl. In some embodiments of a compound of Formula (I) or (Ia)-(Ie), $R^4$ is hydrogen, halogen, —$OR^a$, or $C_1$-$C_6$alkyl. In some embodiments of a compound of Formula (I) or (Ia)-(Ie), $R^4$ is hydrogen, or halogen, or $C_1$-$C_6$alkyl. In some embodiments of a compound of Formula (I) or (Ia)-(Ie), $R^4$ is hydrogen or halogen. In some embodiments of a compound of Formula (I) or (Ia)-(Ie), $R^4$ is halogen. In some embodiments of a compound of Formula (I) or (Ia)-(Ie), $R^4$ is hydrogen. In some embodiments of a compound of Formula (I) or (Ia)-(Ie), $R^4$ is not hydrogen.

In some embodiments of a compound of Formula (I) or (Ia)-(Ie), $R^5$ is hydrogen, deuterium, halogen, —$OR^a$, $C_1$-$C_6$alkyl, $C_1$-$C_6$haloalkyl, or $C_1$-$C_6$deuteroalkyl. In some embodiments of a compound of Formula (I) or (Ia)-(Ie), $R^5$ is hydrogen, halogen, —$OR^a$, or $C_1$-$C_6$alkyl. In some embodiments of a compound of Formula (I) or (Ia)-(Ie), $R^5$ is hydrogen, or halogen, or $C_1$-$C_6$alkyl.

In some embodiments of a compound of Formula (I) or (Ia)-(Ie), $R^5$ is hydrogen or halogen. In some embodiments of a compound of Formula (I) or (Ia)-(Ie), $R^5$ is halogen. In some embodiments of a compound of Formula (I) or (Ia)-(Ie), $R^5$ is hydrogen. In some embodiments of a compound of Formula (I) or (Ia)-(Ie), $R^5$ is not hydrogen.

In some embodiments of a compound of Formula (I) or (Ia)-(Ie), each $R^6$ is independently hydrogen, deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ie), each $R^6$ is independently hydrogen, deuterium, or $C_1$-$C_6$alkyl. In some embodiments of a compound of Formula (I) or (Ia)-(Ie), one $R^6$ is hydrogen and the other $R^6$ is $C_1$-$C_6$alkyl. In some embodiments of a compound of Formula (I) or (Ia)-(Ie), each $R^6$ is deuterium. In some embodiments of a compound of Formula (I) or (Ia)-(Ie), each $R^6$ is independently $C_1$-$C_6$alkyl. In some embodiments of a compound of Formula (I) or (Ia)-(Ie), each $R^6$ is hydrogen. In some embodiments of a compound of Formula (I) or (Ia)-(Ie), two $R^6$ are taken together to form a cycloalkyl. In some embodiments of a compound of Formula (I) or (Ia)-(Ie), two $R^6$ are taken together to form a cyclopropyl.

In some embodiments of a compound of Formula (I) or (Ia)-(Ie), each $R^7$ is independently $C_1$-$C_6$alkyl, $C_1$-$C_6$haloalkyl, or $C_1$-$C_6$deuteroalkyl. In some embodiments of a compound of Formula (I) or (Ia)-(Ie), each $R^7$ is independently $C_1$-$C_6$alkyl. In some embodiments of a compound of Formula (I) or (Ia)-(Ie), two $R^7$ on the same carbon or different carbons are taken together to form a cycloalkyl. In some embodiments of a compound of Formula (I) or (Ia)-(Ie), two $R^7$ on the same carbon or different carbons are taken together to form a cyclopropyl.

In some embodiments of a compound of Formula (I) or (Ia)-(Ie), n is 0 or 1. In some embodiments of a compound of Formula (I) or (Ia)-(Ie), n is 0-2. In some embodiments of a compound of Formula (I) or (Ia)-(Ie), n is 1 or 2. In some embodiments of a compound of Formula (I) or (Ia)-(Ie), n is 1. In some embodiments of a compound of Formula (I) or (Ia)-(Ie), n is 2. In some embodiments of a compound of Formula (I) or (Ia)-(Ie), n is 3. In some embodiments of a compound of Formula (I) or (Ia)-(Ie), n is 4.

In some embodiments of a compound of Formula (I) or (Ia)-(Ie), T is N. In some embodiments of a compound of Formula (I) or (Ia)-(Ie), T is $CR^8$.

In some embodiments of a compound of Formula (I) or (Ia)-(Ie), U is N. In some embodiments of a compound of Formula (I) or (Ia)-(Ie), U is $CR^9$.

In some embodiments of a compound of Formula (I) or (Ia)-(Ie),

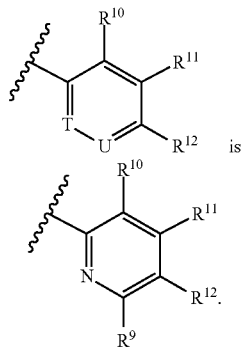

is

In some embodiments of a compound of Formula (I) or (Ia)-(Ie),

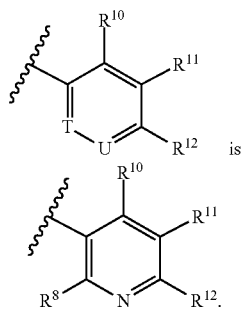

is

In some embodiments of a compound of Formula (I) or (Ia)-(Ie), $R^8$ is hydrogen, deuterium, halogen, —CN, —OH, —$OR^a$, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^8$ is hydrogen, halogen, —CN, —$OR^a$, $C_1$-$C_6$alkyl, or $C_1$-$C_6$haloalkyl. In some embodiments of a compound of Formula (I) or (Ia)-(Ie), $R^8$ is hydrogen, halogen, —CN, —$OR^a$, or $C_1$-$C_6$haloalkyl. In some embodiments of a compound of Formula (I) or (Ia)-(Ie), $R^8$ is hydrogen, halogen, or $C_1$-$C_6$haloalkyl. In some embodiments of a compound of Formula (I) or (Ia)-(Ie), $R^8$ is hydrogen or halogen. In some embodiments of a compound of Formula (I) or (Ia)-(Ie), $R^8$ is hydrogen.

In some embodiments of a compound of Formula (I) or (Ia)-(Ie), $R^9$ is hydrogen, deuterium, halogen, —CN, —OH, —$OR^a$, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^9$ is hydrogen, deuterium, halogen, —CN, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^9$ is hydrogen, halogen, —$C_1$-$C_6$alkyl, $C_1$-$C_6$haloalkyl, or cycloalkyl. In some embodiments of a compound of Formula (I) or (Ia)-(Ie), $R^9$ is hydrogen, halogen, or cycloalkyl. In some embodiments of a compound of Formula (I) or (Ia)-(Ie), $R^9$ is hydrogen or halogen. In some embodiments of a compound of Formula (I) or (Ia)-(Ie), $R^9$ is hydrogen.

In some embodiments of a compound of Formula (I) or (Ia)-(Ie), $R^{10}$ is hydrogen, deuterium, halogen, —CN, —OH, —$OR^E$, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^{10}$ is hydrogen, deuterium, halogen, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^{10}$ is hydrogen, halogen, $C_1$-$C_6$alkyl, or $C_1$-$C_6$haloalkyl. In some embodiments of a compound of Formula (I) or (Ia)-(Ie), $R^{10}$ is hydrogen or halogen. In some embodiments of a compound of Formula (I) or (Ia)-(Ie), $R^{10}$ is hydrogen.

In some embodiments of a compound of Formula (I) or (Ia)-(Ie), $R^{11}$ is hydrogen, deuterium, halogen, —CN, —OH, —$OR^a$, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^{11}$ is hydrogen, deuterium, halogen, $C_1$-$C_6$alkyl, $C_1$-$C_6$haloalkyl, $C_1$-$C_6$deuteroalkyl, or cycloalkyl. In some embodiments of a compound of Formula (I) or (Ia)-(Ie), $R^{11}$ is hydrogen, halogen, $C_1$-$C_6$alkyl, or $C_1$-$C_6$haloalkyl. In some embodiments of a compound of Formula (I) or (Ia)-(Ie), $R^{11}$ is hydrogen or halogen. In some embodiments of a compound of Formula (I) or (Ia)-(Ie), $R^{11}$ is hydrogen.

In some embodiments of a compound of Formula (I) or (Ia)-(Ie), $R^{12}$ is cyano. In some embodiments of a compound of Formula (I) or (Ia)-(Ie), $R^{12}$ is halogen. In some embodiments of a compound of Formula (I) or (Ia)-(Ie), $R^{12}$ is fluoro or chloro. In some embodiments of a compound of Formula (I) or (Ia)-(Ie), $R^{12}$ is fluoro. In some embodiments of a compound of Formula (I) or (Ia)-(Ie), $R^{12}$ is chloro. In some embodiments of a compound of Formula (I) or (Ia)-(Ie), $R^{12}$ is fluoro or bromo.

In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^a$ is independently $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^a$ is independently $C_1$-$C_6$alkyl, $C_1$-$C_6$haloalkyl, or cycloalkyl, heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl. In some embodiments of a compound disclosed herein, each $R^a$ is independently $C_1$-$C_6$haloalkyl.

In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^b$ is independently hydrogen, $C_1$-$C_6$alkyl, $C_1$-$C_6$haloalkyl, or cycloalkyl, heterocycloalkyl. In some embodiments of a compound disclosed herein, each $R^b$ is independently hydrogen, $C_1$-$C_6$alkyl or $C_1$-$C_6$haloalkyl. In some embodiments of a compound disclosed herein, each $R^b$ is independently hydrogen or $C_1$-$C_6$alkyl. In some embodiments of a compound disclosed herein, each $R^b$ is hydrogen. In some embodiments of a compound disclosed herein, each $R^b$ is independently $C_1$-$C_6$alkyl. In some embodiments of a compound disclosed herein, each $R^b$ is independently $C_1$-$C_6$haloalkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^c$ and $R^d$ are independently hydrogen, $C_1$-$C_6$alkyl, $C_1$-$C_6$haloalkyl, or cycloalkyl, heterocycloalkyl. In some embodiments of a compound disclosed herein, each $R^c$ and $R^d$ are independently hydrogen, $C_1$-$C_6$alkyl or $C_1$-$C_6$haloalkyl. In some embodiments of a compound disclosed herein, each $R^c$ and $R^d$ are independently hydrogen or $C_1$-$C_6$alkyl. In some embodiments of a compound disclosed herein, each $R^c$ and $R^d$ are hydrogen. In some embodiments of a compound disclosed herein, each $R^c$ and $R^d$ are independently $C_1$-$C_6$alkyl. In some embodiments of a compound disclosed herein, each $R^c$ and $R^d$ are independently $C_1$-$C_6$haloalkyl.

In some embodiments of a compound disclosed herein, $R^c$ and $R^d$ are taken together with the atom to which they are attached to form a heterocycloalkyl optionally substituted with one or more R.

In some embodiments of a compound disclosed herein, each R is independently deuterium, halogen, —CN, —OH, —O$C_1$-$C_6$alkyl, —NH$_2$, —NH$C_1$-$C_6$alkyl, —N($C_1$-$C_6$alkyl)$_2$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; or two R on the same atom are taken together to form an oxo. In some embodiments of a compound disclosed herein, each R is independently deuterium, halogen, —CN, —OH, —O$C_1$-$C_6$alkyl, —NH$_2$, —NH$C_1$-$C_6$alkyl, —N($C_1$-$C_6$alkyl)$_2$, $C_1$-$C_6$alkyl, $C_1$-$C_6$haloalkyl, or $C_1$-$C_6$deuteroalkyl; or two R on the same atom are taken together to form an oxo. In some embodiments of a compound disclosed herein, each R is independently deuterium, halogen, —CN, —OH, —O$C_1$-$C_6$alkyl, —NH$_2$, $C_1$-$C_6$alkyl, or $C_1$-$C_6$haloalkyl; or two R on the same atom are taken together to form an oxo.

Any combination of the groups described above for the various variables is contemplated herein. Throughout the specification, groups and substituents thereof are chosen by one skilled in the field to provide stable moieties and compounds.

In some embodiments, the compound disclosed herein, or a pharmaceutically acceptable salt, solvate, or stereoisomer thereof, is selected from a compound of Table 1.

TABLE 1

| Example | Structure |
|---------|-----------|
| 1 | 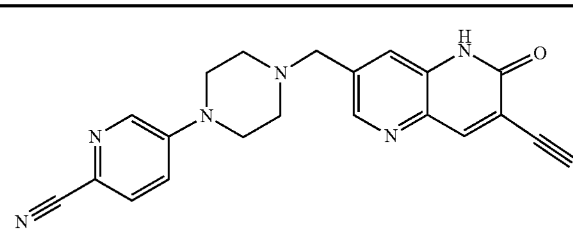 |

TABLE 1-continued

| Example | Structure |
|---|---|
| 2 | 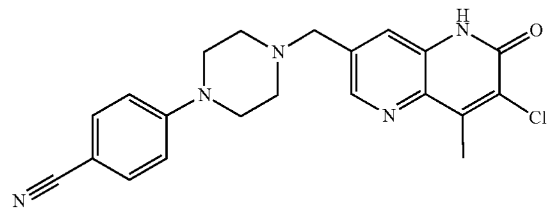 [SMILES: Cc1c(Cl)c(=O)[nH]c2cc(CN3CCN(c4ccc(C#N)cc4)CC3)cnc12] |
| 3 | 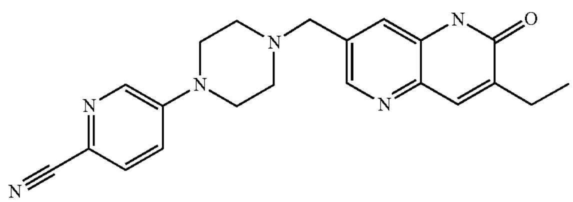 |
| 4 | 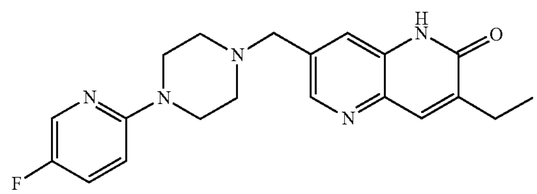 [SMILES: CCc1cc2ncc(CN3CCN(c4ccc(F)cn4)CC3)cc2[nH]c1=O] |
| 5 | 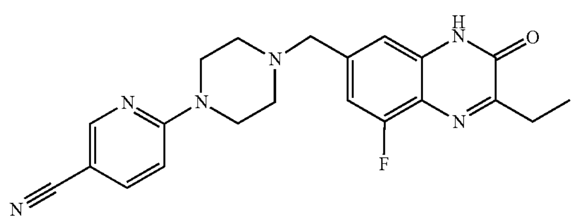 [SMILES: CCc1nc2c(F)cc(CN3CCN(c4ccc(C#N)cn4)CC3)cc2[nH]c1=O] |
| 6 | 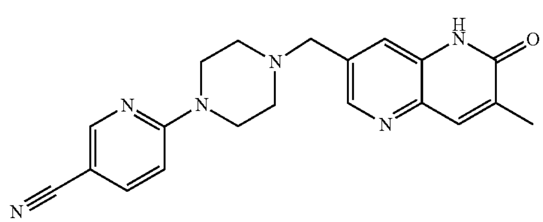 [SMILES: Cc1cc2ncc(CN3CCN(c4ccc(C#N)cn4)CC3)cc2[nH]c1=O] |
| 7 | 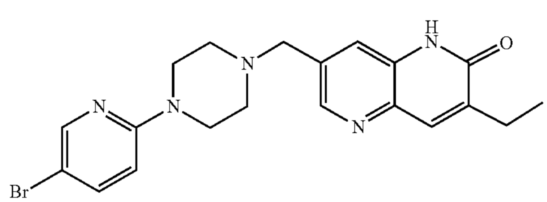 [SMILES: CCc1cc2ncc(CN3CCN(c4ccc(Br)cn4)CC3)cc2[nH]c1=O] |
| 8 | 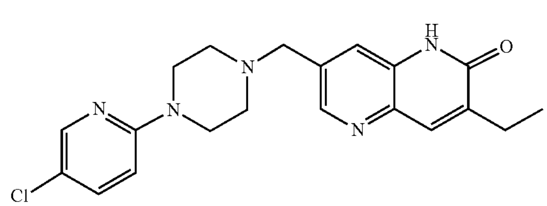 [SMILES: CCc1cc2ncc(CN3CCN(c4ccc(Cl)cn4)CC3)cc2[nH]c1=O] |

TABLE 1-continued
| Example | Structure |
|---|---|
| 9 | 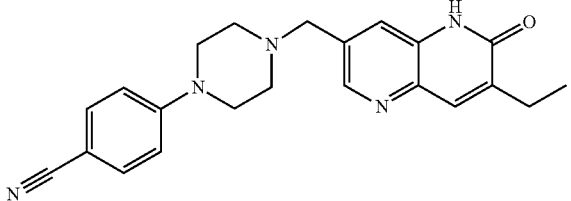 [SMILES: CCc1cc2ncc(CN3CCN(c4ccc(C#N)cc4)CC3)cc2[nH]c1=O] |
| 10 | 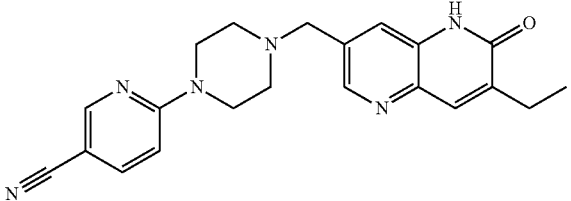 [SMILES: CCc1cc2ncc(CN3CCN(c4ccc(C#N)cn4)CC3)cc2[nH]c1=O] |
| 11 | 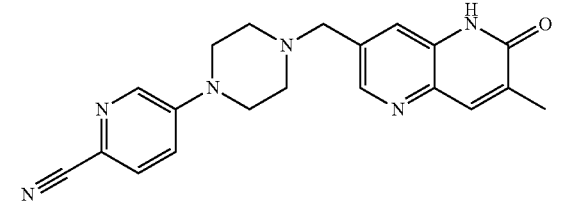 |
| 12 | 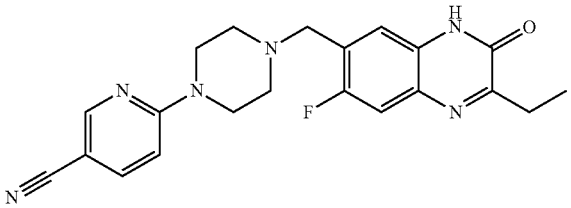 [SMILES: CCc1nc2cc(F)c(CN3CCN(c4ccc(C#N)cn4)CC3)cc2[nH]c1=O] |
| 13 | 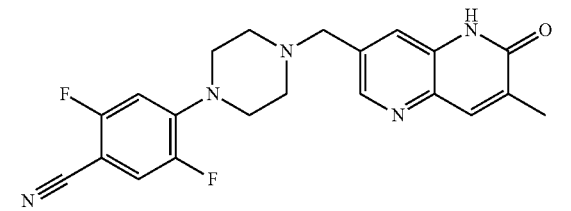 [SMILES: Cc1cc2ncc(CN3CCN(c4cc(F)c(C#N)cc4F)CC3)cc2[nH]c1=O] |
| 14 | 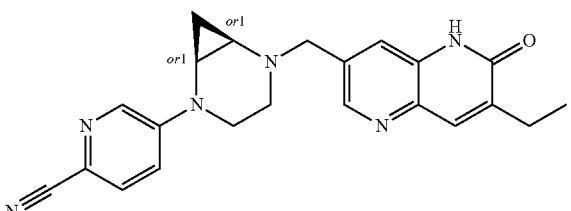 |
| 15 | 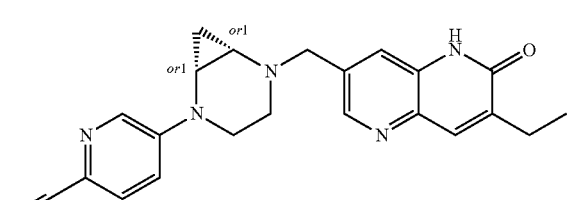 |

TABLE 1-continued

| Example | Structure |
|---|---|
| 16 | 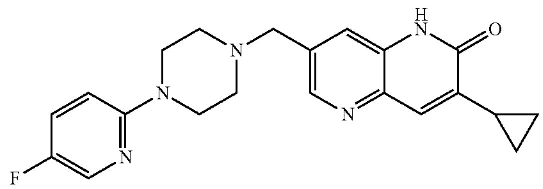 [SMILES: O=c1[nH]c2cc(CN3CCN(c4ccc(F)cn4)CC3)cnc2cc1C1CC1] |
| 17 | 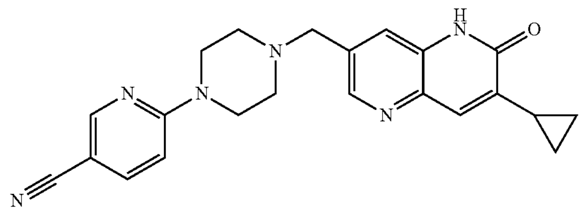 [SMILES: N#Cc1ccc(N2CCN(Cc3cnc4cc(C5CC5)c(=O)[nH]c4c3)CC2)nc1] |
| 18 | 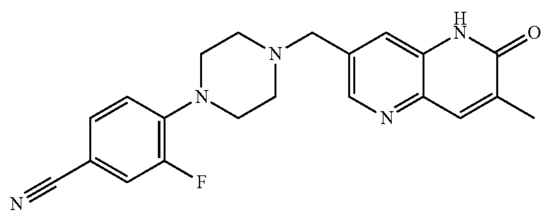 [SMILES: Cc1cc2ncc(CN3CCN(c4ccc(C#N)cc4F)CC3)cc2[nH]c1=O] |
| 19 | 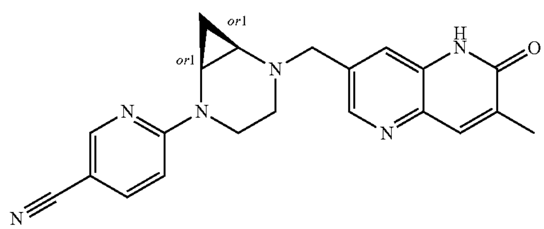 [SMILES: Cc1cc2ncc(CN3CCN(c4ccc(C#N)cn4)[C@H]4C[C@H]43)cc2[nH]c1=O] |
| 20 | 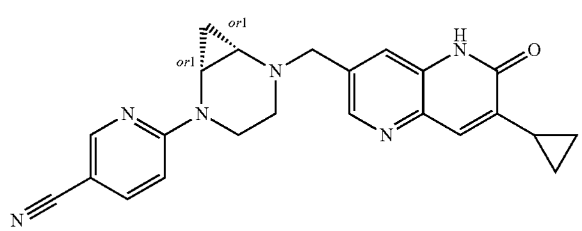 [SMILES: N#Cc1ccc(N2CCN(Cc3cnc4cc(C5CC5)c(=O)[nH]c4c3)[C@H]3C[C@H]32)nc1] |
| 21 | 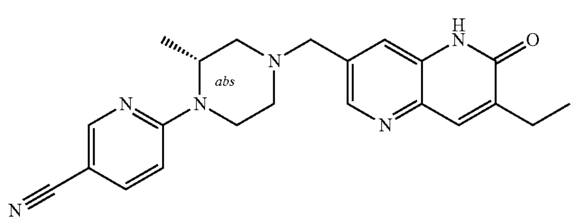 [SMILES: CCc1cc2ncc(CN3CCN(c4ccc(C#N)cn4)[C@H](C)C3)cc2[nH]c1=O] |
| 22 | 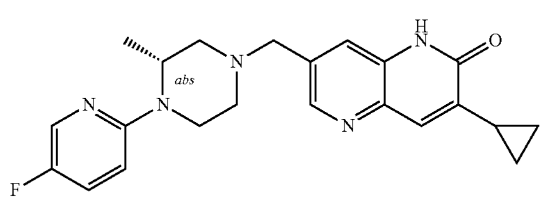 [SMILES: C[C@@H]1CN(Cc2cnc3cc(C4CC4)c(=O)[nH]c3c2)CCN1c1ccc(F)cn1] |

TABLE 1-continued

| Example | Structure |
|---|---|
| 23 | *(chemical structure: 3-methyl-7-{[(2S)-2-methyl-4-(5-fluoropyridin-2-yl)piperazin-1-yl]methyl}-1,5-naphthyridin-2(1H)-one)* |
| 24 | *(chemical structure: 6-{(3S)-3-methyl-4-[(3-methyl-2-oxo-1,2-dihydro-1,5-naphthyridin-7-yl)methyl]piperazin-1-yl}pyridine-3-carbonitrile)* |
| 25 | *(chemical structure: 6-{(3S)-3-methyl-4-[(3-cyclopropyl-2-oxo-1,2-dihydro-1,5-naphthyridin-7-yl)methyl]piperazin-1-yl}pyridine-3-carbonitrile)* |
| 26 | *(chemical structure: 7-{[4-(3,5-difluoropyridin-2-yl)piperazin-1-yl]methyl}-3-methyl-1,5-naphthyridin-2(1H)-one)* |
| 27 | *(chemical structure: 6-cyclopropyl-5-{4-[(3-methyl-2-oxo-1,2-dihydro-1,5-naphthyridin-7-yl)methyl]piperazin-1-yl}pyridine-2-carbonitrile)* |
| 28 | *(chemical structure with abs and or1 stereochemistry labels: piperazine-cyanopyridine-naphthyridinone with chiral methyl)* |
| 29 | *(chemical structure with abs and or1 stereochemistry labels: piperazine-cyanopyridine-naphthyridinone with chiral methyl, opposite configuration)* |

TABLE 1-continued

| Example | Structure |
|---|---|
| 30 | 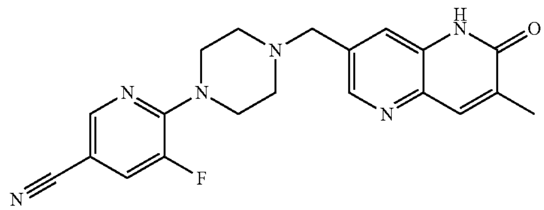 [SMILES: Cc1cc2ncc(CN3CCN(c4ncc(C#N)cc4F)CC3)cc2[nH]c1=O] |
| 31 | 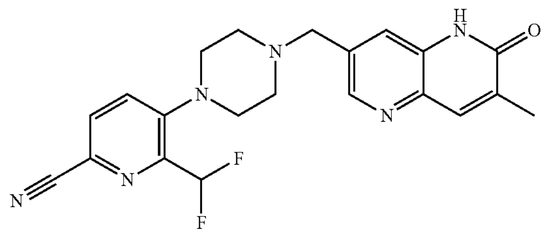 [SMILES: Cc1cc2ncc(CN3CCN(c4ccc(C#N)nc4C(F)F)CC3)cc2[nH]c1=O] |
| 32 | 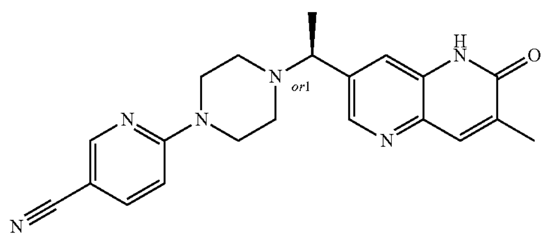 [SMILES: Cc1cc2ncc([C@H](C)N3CCN(c4ccc(C#N)cn4)CC3)cc2[nH]c1=O] |
| 33 | 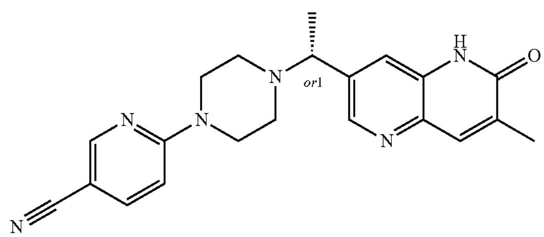 [SMILES: Cc1cc2ncc([C@@H](C)N3CCN(c4ccc(C#N)cn4)CC3)cc2[nH]c1=O] |
| 34 | 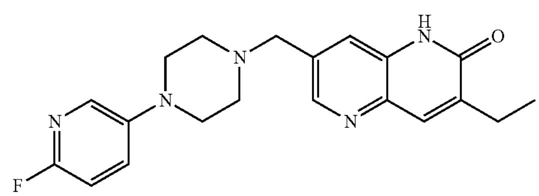 [SMILES: CCc1cc2ncc(CN3CCN(c4ccc(F)nc4)CC3)cc2[nH]c1=O] |
| 35 | 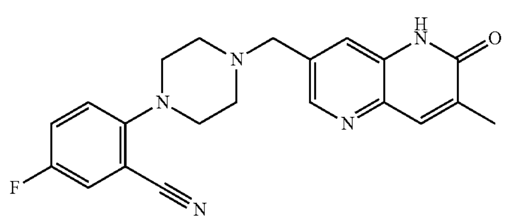 [SMILES: Cc1cc2ncc(CN3CCN(c4ccc(F)cc4C#N)CC3)cc2[nH]c1=O] |
| 36 | 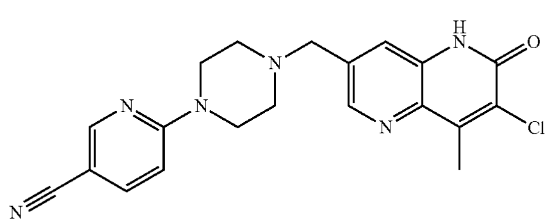 [SMILES: Cc1c(Cl)c(=O)[nH]c2cc(CN3CCN(c4ccc(C#N)cn4)CC3)cnc12] |

TABLE 1-continued
| Example | Structure |
|---------|-----------|
| 37 | 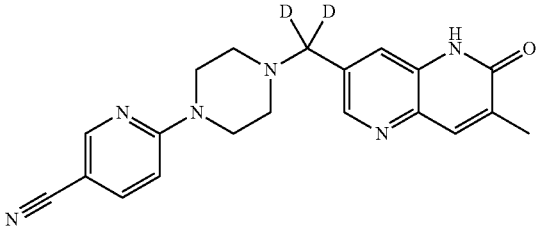 [SMILES: [2H]C([2H])(c1cnc2cc(C)c(=O)[nH]c2c1)N1CCN(c2ccc(C#N)cn2)CC1] |
| 38 | 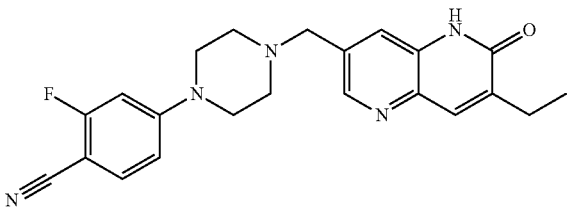 [SMILES: CCc1cc2ncc(CN3CCN(c4ccc(C#N)c(F)c4)CC3)cc2[nH]c1=O] |
| 39 | 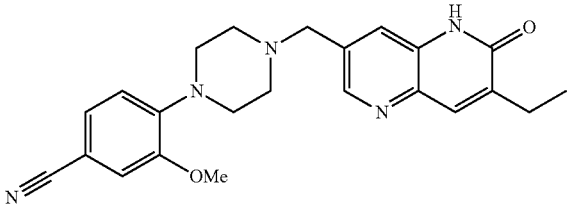 [SMILES: CCc1cc2ncc(CN3CCN(c4ccc(C#N)cc4OC)CC3)cc2[nH]c1=O] |
| 40 | 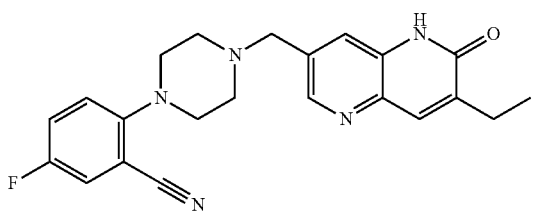 [SMILES: CCc1cc2ncc(CN3CCN(c4ccc(F)cc4C#N)CC3)cc2[nH]c1=O] |
| 41 | 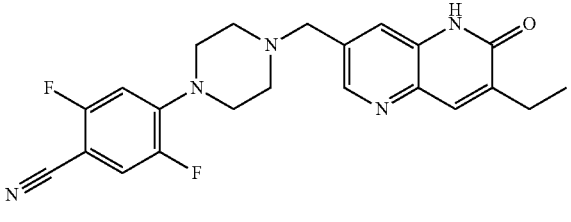 [SMILES: CCc1cc2ncc(CN3CCN(c4cc(F)c(C#N)cc4F)CC3)cc2[nH]c1=O] |
| 42 | 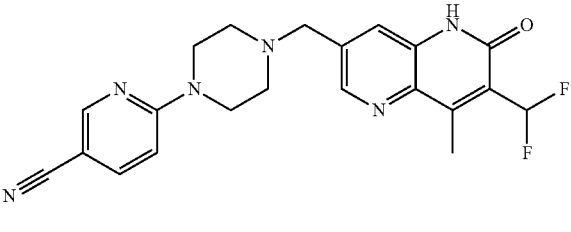 [SMILES: Cc1c(C(F)F)c(=O)[nH]c2cc(CN3CCN(c4ccc(C#N)cn4)CC3)cnc12] |
| 43 | 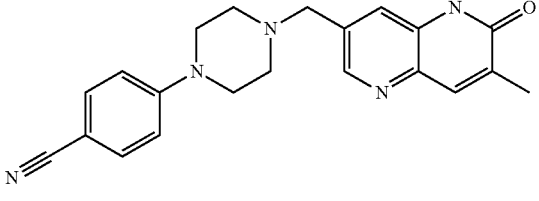 |

TABLE 1-continued
| Example | Structure |
|---|---|
| 44 | 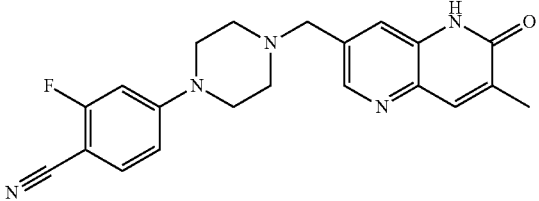 [SMILES: Cc1cc2ncc(CN3CCN(c4ccc(C#N)c(F)c4)CC3)cc2[nH]c1=O] |
| 45 | 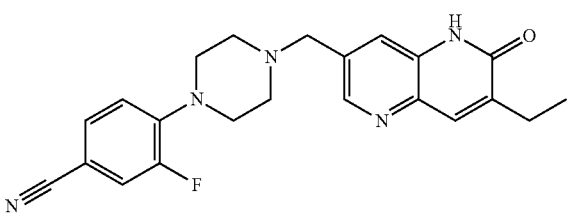 [SMILES: CCc1cc2ncc(CN3CCN(c4ccc(C#N)cc4F)CC3)cc2[nH]c1=O] |
| 46 | 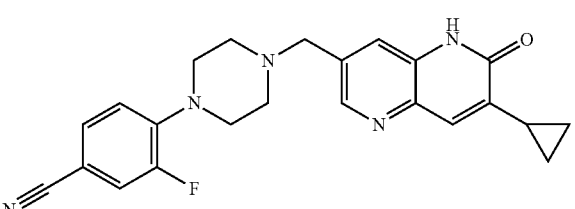 |
| 47 | 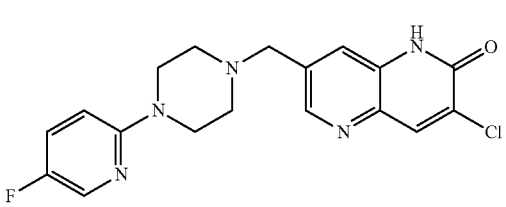 [SMILES: O=c1[nH]c2cc(CN3CCN(c4ccc(F)cn4)CC3)cnc2cc1Cl] |
| 48 | 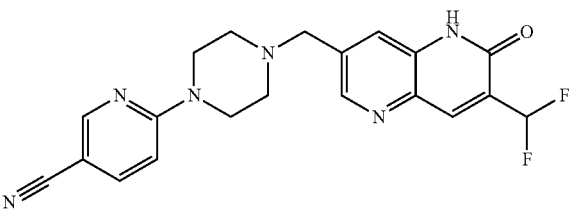 [SMILES: N#Cc1ccc(N2CCN(Cc3cnc4cc(C(F)F)c(=O)[nH]c4c3)CC2)nc1] |
| 49 | 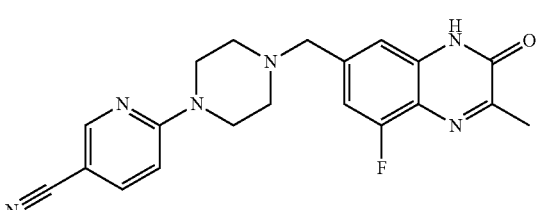 |
| 50 | 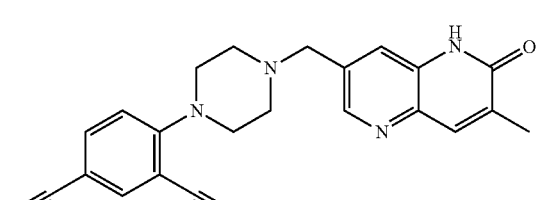 |

TABLE 1-continued

| Example | Structure |
| --- | --- |
| 51 | 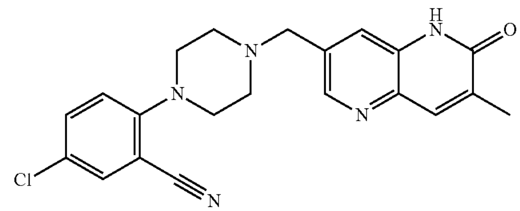 [SMILES: Cc1cc2ncc(CN3CCN(c4ccc(Cl)cc4C#N)CC3)cc2[nH]c1=O] |
| 52 | 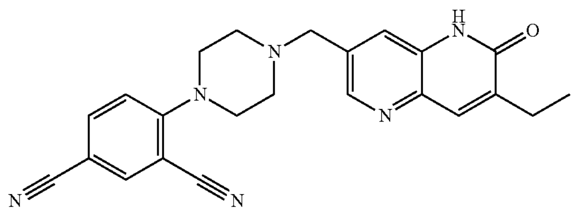 [SMILES: CCc1cc2ncc(CN3CCN(c4ccc(C#N)cc4C#N)CC3)cc2[nH]c1=O] |
| 53 | 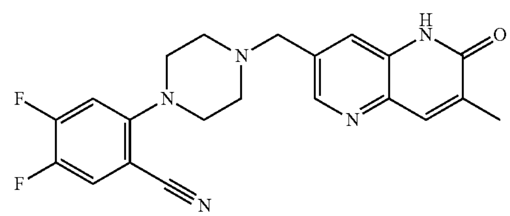 [SMILES: Cc1cc2ncc(CN3CCN(c4cc(F)c(F)cc4C#N)CC3)cc2[nH]c1=O] |
| 54 | 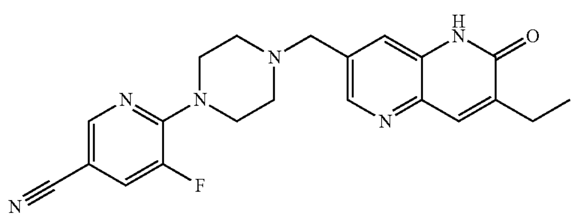 [SMILES: CCc1cc2ncc(CN3CCN(c4ncc(C#N)cc4F)CC3)cc2[nH]c1=O] |
| 55 | 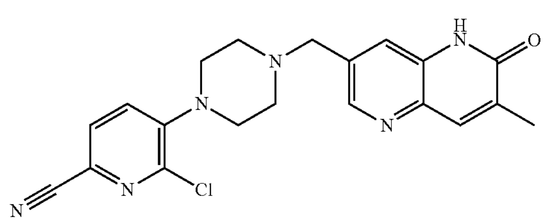 |
| 56 | 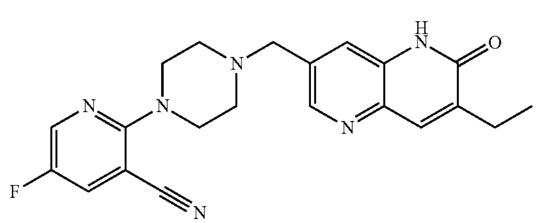 [SMILES: CCc1cc2ncc(CN3CCN(c4ncc(F)cc4C#N)CC3)cc2[nH]c1=O] |
| 57 | 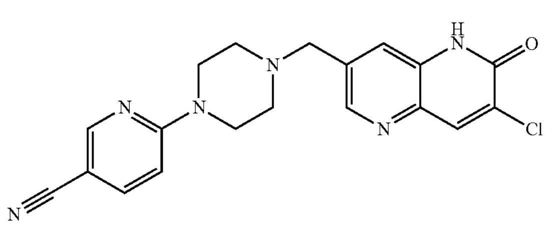 [SMILES: N#Cc1ccc(N2CCN(Cc3cnc4cc(Cl)c(=O)[nH]c4c3)CC2)nc1] |

TABLE 1-continued
| Example | Structure |
|---|---|
| 58 | 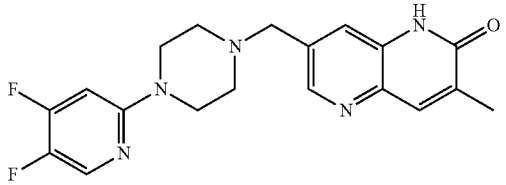 [SMILES: Cc1cc2ncc(CN3CCN(c4cc(F)c(F)cn4)CC3)cc2[nH]c1=O] |
| 59 | 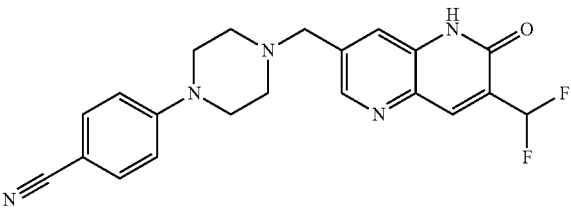 [SMILES: N#Cc1ccc(N2CCN(Cc3cnc4cc(C(F)F)c(=O)[nH]c4c3)CC2)cc1] |
| 60 | 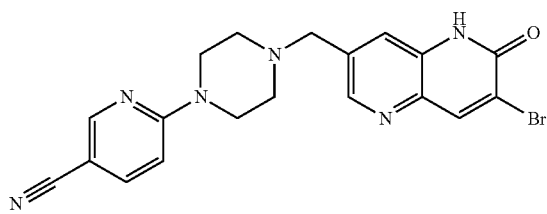 [SMILES: N#Cc1ccc(N2CCN(Cc3cnc4cc(Br)c(=O)[nH]c4c3)CC2)nc1] |
| 61 | 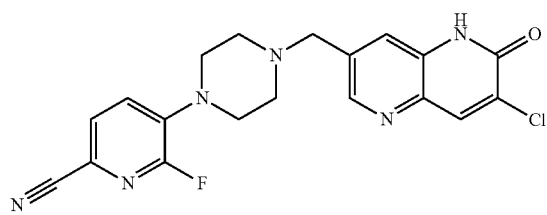 [SMILES: N#Cc1ccc(N2CCN(Cc3cnc4cc(Cl)c(=O)[nH]c4c3)CC2)c(F)n1] |
| 62 | 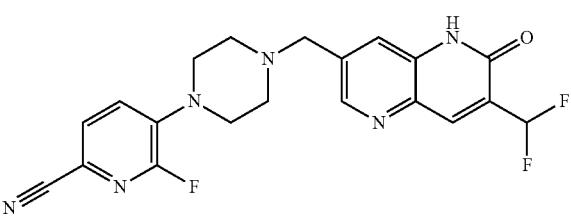 [SMILES: N#Cc1ccc(N2CCN(Cc3cnc4cc(C(F)F)c(=O)[nH]c4c3)CC2)c(F)n1] |
| 63 | 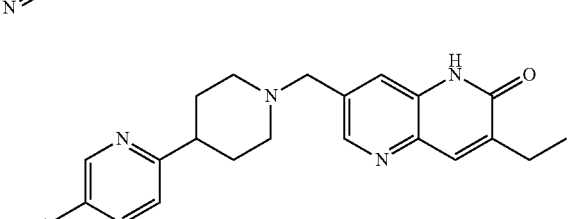 |
| 64 | 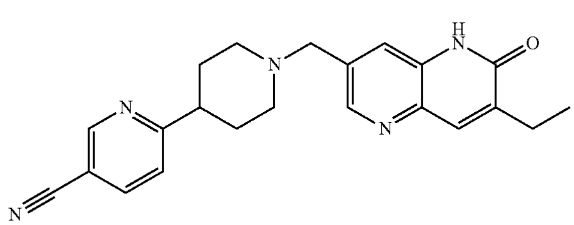 |

TABLE 1-continued

| Example | Structure |
|---|---|
| 65 | 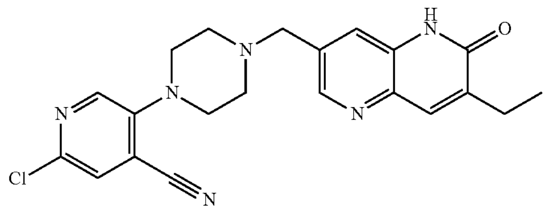 [SMILES: CCc1cc2ncc(CN3CCN(c4cnc(Cl)cc4C#N)CC3)cc2[nH]c1=O] |
| 66 | 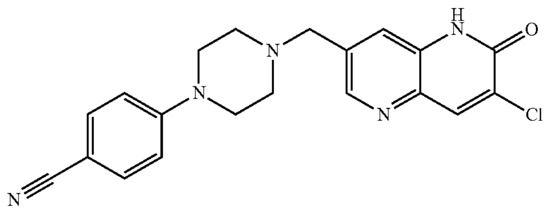 [SMILES: N#Cc1ccc(N2CCN(Cc3cnc4cc(Cl)c(=O)[nH]c4c3)CC2)cc1] |
| 67 | 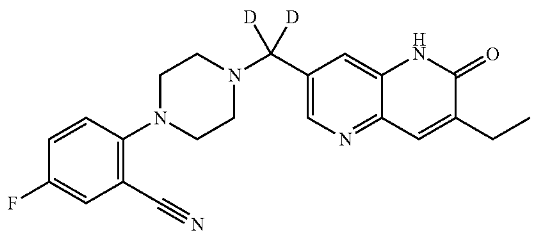 [SMILES: [2H]C([2H])(c1cnc2cc(CC)c(=O)[nH]c2c1)N1CCN(c2ccc(F)cc2C#N)CC1] |
| 68 | 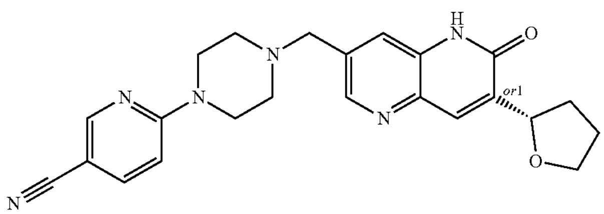 [SMILES: N#Cc1ccc(N2CCN(Cc3cnc4cc([C@@H]5CCCO5)c(=O)[nH]c4c3)CC2)nc1] |
| 69 | 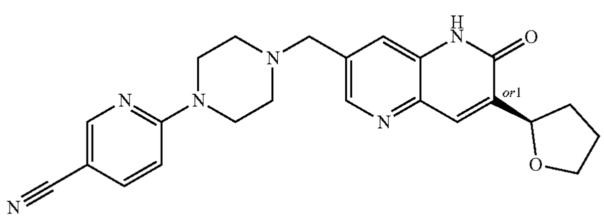 [SMILES: N#Cc1ccc(N2CCN(Cc3cnc4cc([C@H]5CCCO5)c(=O)[nH]c4c3)CC2)nc1] |
| 70 | 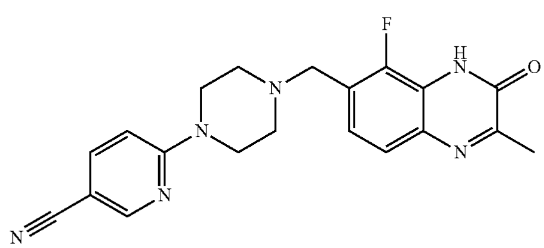 [SMILES: Cc1nc2ccc(CN3CCN(c4ccc(C#N)cn4)CC3)c(F)c2[nH]c1=O] |
| 71 | 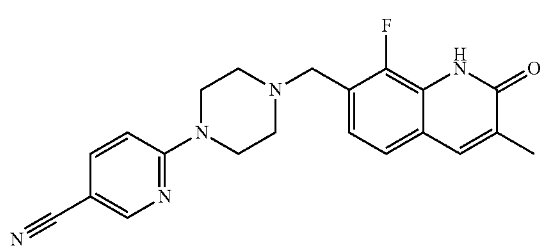 [SMILES: Cc1cc2ccc(CN3CCN(c4ccc(C#N)cn4)CC3)c(F)c2[nH]c1=O] |

TABLE 1-continued

| Example | Structure |
|---|---|
| 72 | 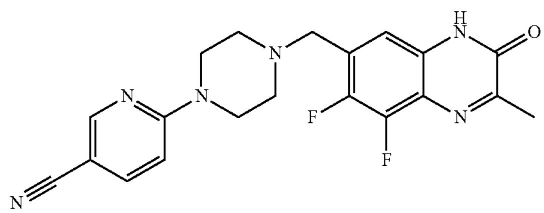 [SMILES: Cc1nc2c(F)c(F)c(CN3CCN(c4ccc(C#N)cn4)CC3)cc2[nH]c1=O] |
| 73 | 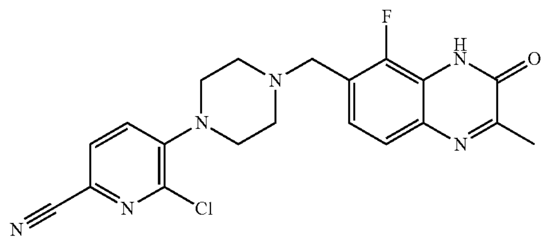 [SMILES: Cc1nc2ccc(CN3CCN(c4ccc(C#N)nc4Cl)CC3)c(F)c2[nH]c1=O] |
| 74 | 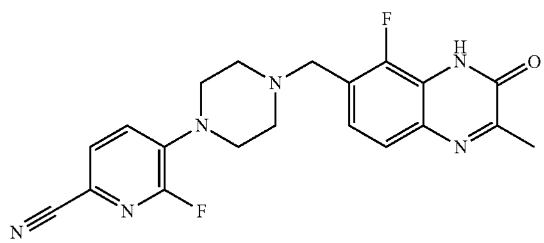 [SMILES: Cc1nc2ccc(CN3CCN(c4ccc(C#N)nc4F)CC3)c(F)c2[nH]c1=O] |
| 75 | 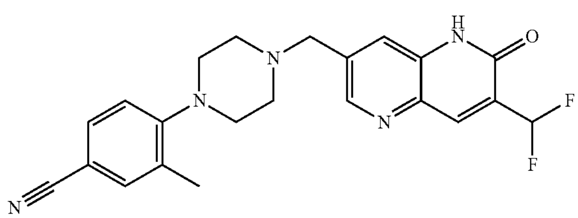 [SMILES: Cc1cc(C#N)ccc1N1CCN(Cc2cnc3cc(C(F)F)c(=O)[nH]c3c2)CC1] |
| 76 | 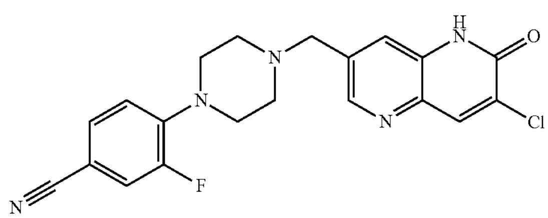 [SMILES: N#Cc1ccc(N2CCN(Cc3cnc4cc(Cl)c(=O)[nH]c4c3)CC2)c(F)c1] |
| 77 | 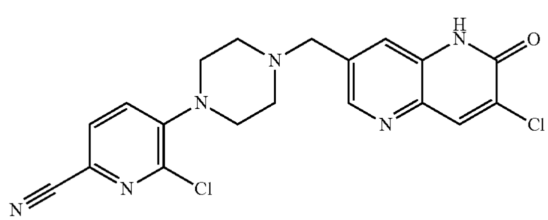 [SMILES: N#Cc1ccc(N2CCN(Cc3cnc4cc(Cl)c(=O)[nH]c4c3)CC2)c(Cl)n1] |
| 78 | 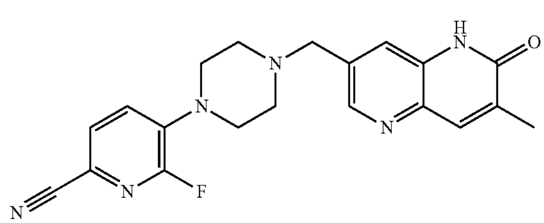 [SMILES: Cc1cc2ncc(CN3CCN(c4ccc(C#N)nc4F)CC3)cc2[nH]c1=O] |

TABLE 1-continued

| Example | Structure |
|---|---|
| 79 | 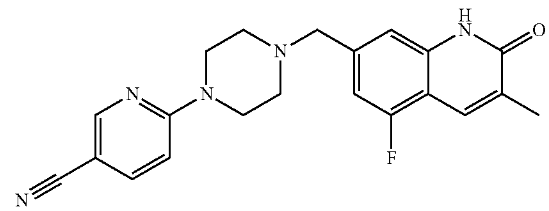 [SMILES: Cc1cc2c(F)cc(CN3CCN(c4ccc(C#N)cn4)CC3)cc2[nH]c1=O] |
| 80 | 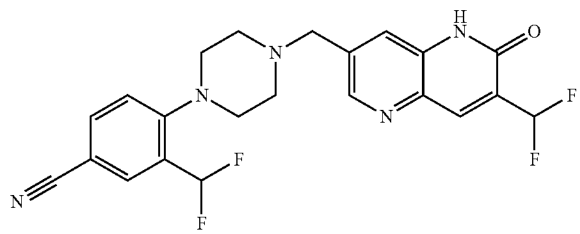 [SMILES: N#Cc1ccc(N2CCN(Cc3cnc4cc(C(F)F)c(=O)[nH]c4c3)CC2)c(C(F)F)c1] |
| 81 | 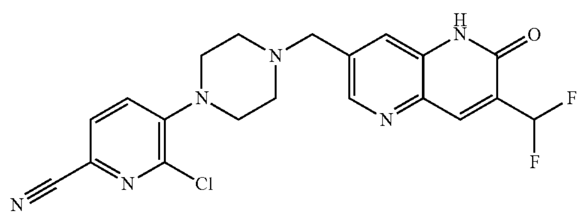 [SMILES: N#Cc1ccc(N2CCN(Cc3cnc4cc(C(F)F)c(=O)[nH]c4c3)CC2)c(Cl)n1] |
| 82 | 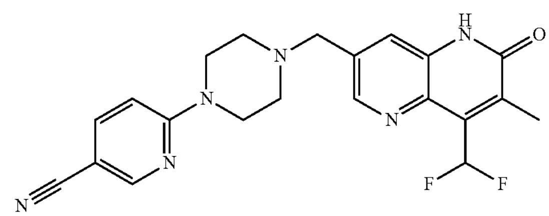 [SMILES: Cc1c(C(F)F)c2ncc(CN3CCN(c4ccc(C#N)cn4)CC3)cc2[nH]c1=O] |
| 83 | 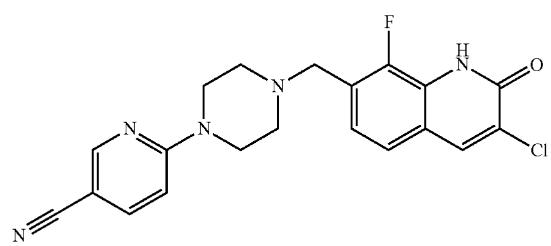 [SMILES: N#Cc1ccc(N2CCN(Cc3ccc4cc(Cl)c(=O)[nH]c4c3F)CC2)nc1] |
| 84 | 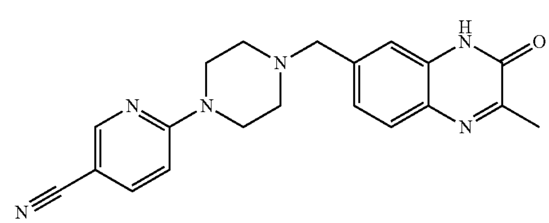 [SMILES: Cc1nc2ccc(CN3CCN(c4ccc(C#N)cn4)CC3)cc2[nH]c1=O] |

The absolute label (abs) is added to a chiral center to denote that it is unambiguously a pure sample of the drawn stereoisomer.

The OR label (or) denotes a pure substance, but the absolute configuration of the stereochemical center is unknown. After chiral separation with pure structures isolated, multiple OR labels (OR indicates purity) with the same numerical value will indicates that a sample is one of a pair of pure enantiomers (but the absolute configuration of the stereochemical center is unknown).

The AND label (and) denotes both isomers are present at the depicted stereochemical center. Assigning different numerical values to the AND labels denotes that they are independent of each other. The use of AND labels with the same values indicate that the two stereocenters are relative to each other and can only change in concert.

In some embodiments, the compound disclosed herein, or a pharmaceutically acceptable salt, solvate, or stereoisomer thereof, is selected from

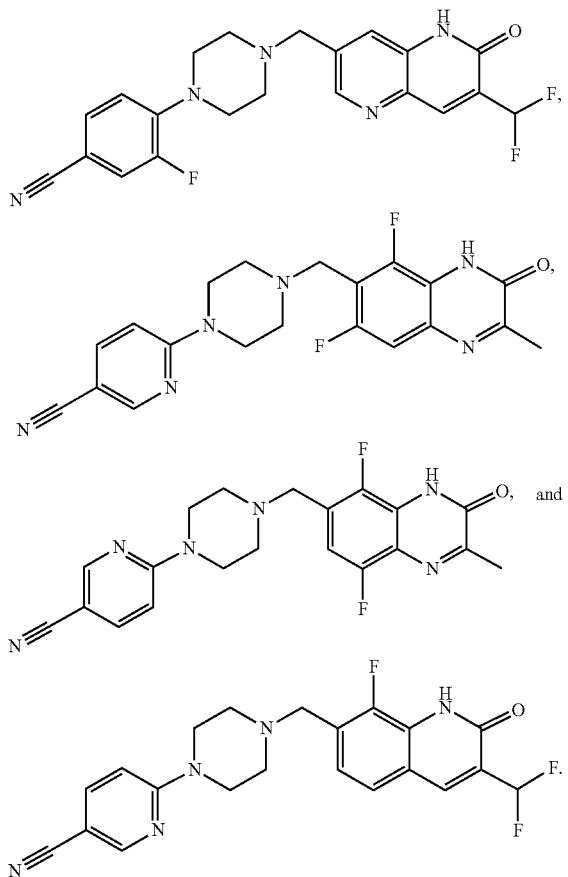

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^2H$, $^3H$, $^{13}C$, $^{14}C$, $^5N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein are methods of treatment of a disease in which inhibition of PARP is beneficial, the method comprising administering a compound disclosed herein. Also disclosed herein are methods of treatment of a disease in which inhibition of PARP1 is beneficial, the method comprising administering a compound disclosed herein. In some embodiments, the disease is cancer. In some embodiments, the cancer is breast cancer, ovarian cancer, pancreatic cancer, prostate cancer, a hematological cancer, a gastrointestinal cancer such as gastric cancer and colorectal cancer, or lung cancer. In some embodiments, the cancer is breast cancer, ovarian cancer, pancreatic cancer, or prostate cancer. In some embodiment, the cancer is leukemia, colon cancer, glioblastoma, lymphoma, melanoma, or cervical cancer. In some embodiments, the cancer is bladder cancer, brain & CNS cancer, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

In some embodiments, the cancer is metastatic cancer. In some embodiments, the cancer has metastasized in the brain.

In some embodiments, the cancer comprises a BRCA1 and/or a BRCA2 mutation.

In some embodiments, the cancer comprising a BRCA1 and/or a BRCA2 mutation is bladder cancer, brain & CNS cancers, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

In some embodiments, the cancer is a cancer deficient in Flomologous Recombination (FIR) dependent DNA DSB repair activity. The FIR dependent DNA DSB repair pathway repairs double-strand breaks (DSBs) in DNA via homologous mechanisms to reform a continuous DNA helix. The components of the FIR dependent DNA DSB repair pathway include, but are not limited to, ATM (NM 000051), RAD51 (NM 002875), RAD51 L1 (NM 002877), RAD51 C (NM 002876), RAD51 L3 (NM 002878), DMC1 (NM_007068), XRCC2 (NM 005431), XRCC3 (NM 005432), RAD52 (NM 002879), RAD54L (NM_003579), RAD54B (NM 012415), BRCA1 (NM 007295), BRCA2 (NM 000059), RAD50 (NM_005732), MRE1 1 A (NM 005590) and NBS1 (NM_002485). Other proteins involved in the FIR dependent DNA DSB repair pathway include regulatory factors such as EMSY. In some embodiments, the cancer which is deficient in FIR dependent DNA DSB repair comprises one or more cancer cells which have a reduced or abrogated ability to repair DNA DSBs through that pathway, relative to normal cells i.e. the activity of the FIR dependent DNA DSB repair pathway may be reduced or abolished in the one or more cancer cells.

In some embodiments, the activity of one or more components of the FIR dependent DNA DSB repair pathway is abolished in the one or more cancer cells of an individual having a cancer which is deficient in FIR dependent DNA DSB repair.

In some embodiments, the cancer cells have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor. BRCA1 and BRCA2 are known tumor suppressors whose wild-type alleles are frequently lost in tumors of heterozygous carriers. Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast cancer, ovarian cancer, pancreatic cancer, prostate cancer, a hematological cancer, gastrointestinal cancer, and lung cancer.

Also disclosed herein is a method of treating a cancer comprising a mutation in a gene conferring homologous repair deficiency in a subject in need thereof, the method comprising administering a compound disclosed herein, or a pharmaceutically acceptable salt, solvate, or stereoisomer thereof. In some embodiments, the mutation in a gene conferring homologous repair deficiency comprises ATM, BRCA1, BRCA2, BARD1, BRIP1, CDK12, CHEK1, CHEK2, FANCL, PALB2, RAD51B, RAD51C, RAD51D, or RAD54L, or any combinations thereof.

Also disclosed herein is a method for treating a cancer that is present in the brain, the method comprising administering a compound disclosed herein, or a pharmaceutically acceptable salt, solvate, or stereoisomer thereof.

In some embodiments, the cancer that is present in the brain arises from primary peripheral tumors that have metastasized to the brain. In some embodiments, the cancer that is present in the brain arises from primary brain tissues.

Also disclosed herein is a method for treating brain cancer, the method comprising administering a compound disclosed herein, or a pharmaceutically acceptable salt, solvate, or stereoisomer thereof.

In some embodiments, the brain cancer is a primary brain tumor that starts in the brain and tends to stay there.

In some embodiments, the brain cancer is a secondary brain tumor. These cancers start somewhere else in the body and travel to the brain. Lung, breast, kidney, colon, and skin cancers are among the most common cancers that spread to the brain.

In some embodiments, the compound disclosed herein, or a pharmaceutically acceptable salt, solvate, or stereoisomer thereof, is capable of penetrating the blood brain barrier (BBB). In some embodiments, the ratio of compound that penetrates the BBB is >0.1, wherein 1 is complete BBB penetration, and 0 is no penetration. In some embodiments, the ratio of compound that penetrates the BBB is >0.2. In some embodiments, the ratio of compound that penetrates the BBB is >0.3. In some embodiments, the ratio of compound that penetrates the BBB is measured using the rat kp,uu assay. In some embodiments, the compound has a ratio of >0.3 (i.e. from 0.3 to 1) as determined in the rat kp,uu assay.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt, solvate, or stereoisomer thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt, solvate, or stereoisomer thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt, solvate, or stereoisomer thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating cancer using a compound disclosed herein, or a pharmaceutically acceptable salt, solvate, or stereoisomer thereof, in combination with an additional therapeutic agent.

In some embodiments, the additional therapeutic agent is an anticancer agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLES

The compounds described herein are synthesized as generally described in general scheme 1 and general scheme 2.

General Scheme 1

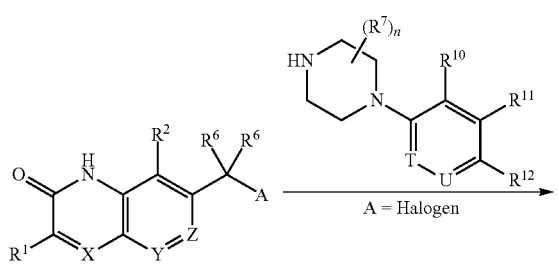

57
-continued
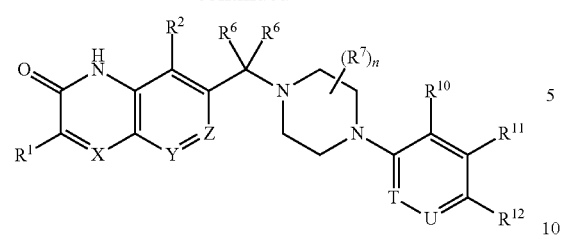
General Scheme 2
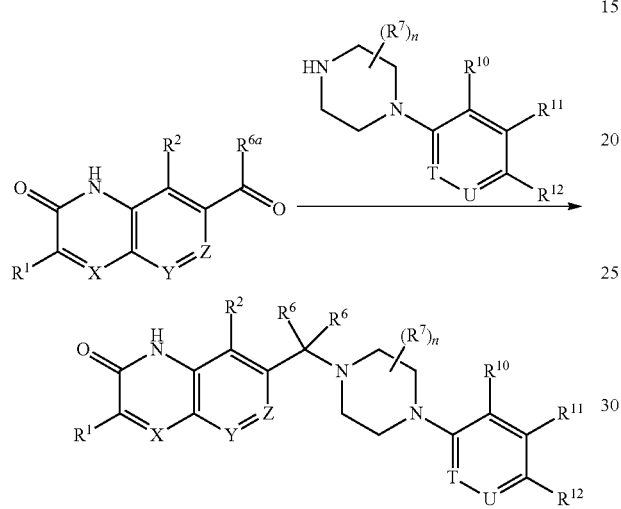
Example 1
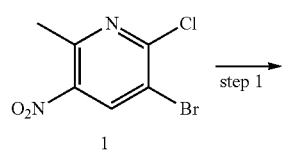
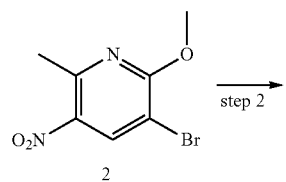
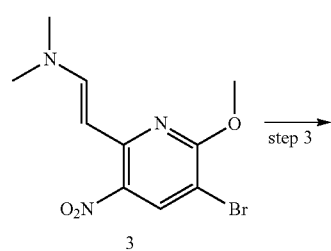
58
-continued
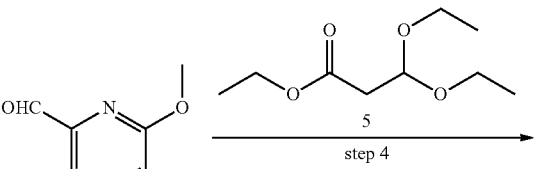
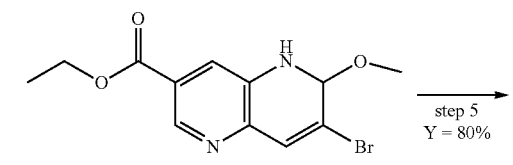
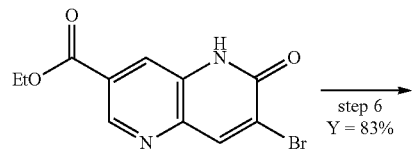
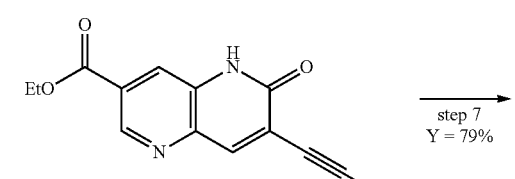
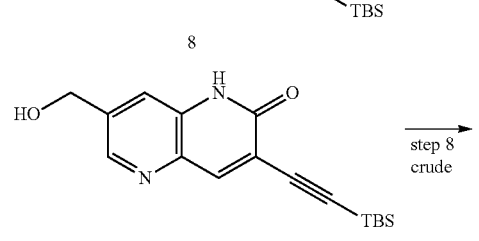
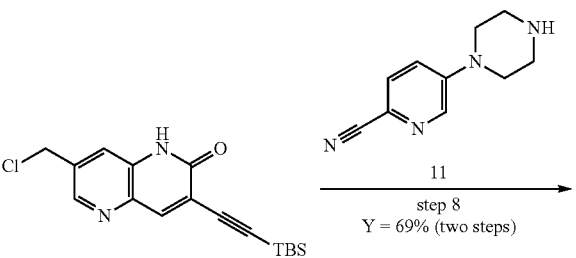

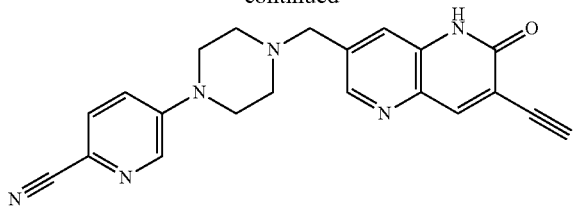

Example 1

Step 1: Preparation of 3-bromo-2-methoxy-6-methyl-5-nitropyridine

To a stirred mixture of 3-bromo-2-chloro-6-methyl-5-nitropyridine (20.00 g, 79.54 mmol, 1.00 equiv) in MeOH (50 mL) was added NaOMe (15.76 g, 87.49 mmol, 1.10 equiv, 30% wt) dropwise at 0° C. under nitrogen atmosphere. The resulting mixture was stirred overnight at rt under nitrogen atmosphere. The reaction was monitored by TLC (Pet. Ether:EtOAc=1:1, $R_f$=0.4). Upon completion, the reaction was concentrated under reduced pressure and water (100 mL) was added. The resulting mixture was extracted with EtOAc (3×100 mL). The combined organic layers were washed with brine (1×200 mL), dried over anhydrous $Na_2SO_4$, filtered and concentrated to afford 3-bromo-2-methoxy-6-methyl-5-nitropyridine (20 g, 99%). $^1$H NMR (400 MHz, DMSO-$d_6$) δ 8.66 (s, 1H), 4.04 (s, 3H), 2.70 (s, 3H).

Step 2: Preparation of (E)-2-(5-bromo-6-methoxy-3-nitropyridin-2-yl)-N,N-dimethylethen-1-amine A mixture of 3-bromo-2-methoxy-6-methyl-5-nitropyridine (15.00 g, 60.72 mmol, 1.00 equiv) in DMF-DMA (100 mL) and DMF (100 mL) was stirred overnight at 100° C. under nitrogen atmosphere. The reaction was monitored by TLC (Pet. Ether:EtOAc=1:1, $R_f$=0.5). The mixture was allowed to cool down to rt and then concentrated under reduced pressure to afford crude (E)-2-(5-bromo-6-methoxy-3-nitropyridin-2-yl)-N,N-dimethylethen-1-amine. The crude product was used in the next step directly without further purification.

Step 3: Preparation of 5-bromo-6-methoxy-3-nitropicolinaldehyde

To a stirred mixture of (E)-2-(5-bromo-6-methoxy-3-nitropyridin-2-yl)ethenyl]dimethylamine (18.01 g, crude) in THF (100 mL) and $H_2O$ (100 mL) was added $NaIO_4$ (28.00 g, 131.07 mmol, 2.20 equiv) in portions at 0° C. under nitrogen atmosphere. The resulting mixture was stirred for 2 h at rt under nitrogen atmosphere. The reaction was monitored by TLC (Pet. Ether:EtOAc=5:1, $R_f$=0.2). The reaction was quenched by the addition of sat. sodium hyposulfite (aq.) (100 mL) at rt. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The crude product was used in the next step directly without further purification. H NMR (400 MHz, DMSO-$d_6$) δ 10.16 (s, 1H), 8.87 (s, 1H), 4.10 (s, 3H).

Step 4: Preparation of ethyl 7-bromo-6-methoxy-1,5-naphthyridine-3-carboxylate To a stirred mixture of 5-bromo-6-methoxy-3-nitropyridine-2-carbaldehyde (7.00 g, crude) and ethyl 3,3-diethoxypropanoate (20.40 g, 107.27 mmol, 4.00 equiv) in EtOH (100 mL) were added $SnCl_2$ (26.25 g, 134.09 mmol, 5.00 equiv) in portions at rt under nitrogen atmosphere. The resulting mixture was stirred overnight at 90° C. under nitrogen atmosphere. The reaction was monitored by LCMS. The mixture was allowed to cool down to rt. The resulting mixture was concentrated under reduced pressure. The crude mixture was poured into saturated sodium bicarbonate (100 mL). The resulting mixture was extracted with EtOAc (3×100 mL). The combined organic layers were concentrated under reduced pressure and the residue was purified by silica gel column chromatography to afford the crude product. The crude product was further purified by trituration with hexane (50 mL) to afford ethyl 7-bromo-6-methoxy-1,5-naphthyridine-3-carboxylate (3.50 g, 18.5%, over three steps). LC-MS: (ES+H, m/z): $[M+H]^+$=311.0

Step 5: Preparation of ethyl 7-bromo-6-oxo-5H-1,5-naphthyridine-3-carboxylate A solution of ethyl 7-bromo-6-methoxy-1,5-naphthyridine-3-carboxylate (5.00 g, 16.07 mmol, 1.00 equiv) in ACN (400 mL) were added TMSI (13.8 mL, 96.42 mmol, 6.00 equiv) dropwise at rt. The final reaction mixture was stirred for 2 h at 80° C. under nitrogen atmosphere. The mixture was allowed to cool down to rt. The reaction was monitored by LCMS. The resulting mixture was concentrated under reduced pressure. The residue was purified by silica gel column chromatography to afford ethyl 7-bromo-6-oxo-5H-1,5-naphthyridine-3-carboxylate (3.8 g, 80%). LC-MS: (ES+H, m/z): $[M+H]^+$=296.95.

Step 6: Preparation of ethyl 7-[2-(tert-butyldimethylsilyl)ethynyl]-6-oxo-5H-1,5-naphthyridine-3-carboxylate A mixture of ethyl 7-bromo-6-oxo-5H-1,5-naphthyridine-3-carboxylate (1.50 g, 5.05 mmol, 1.00 equiv), tert-butyl (ethynyl)dimethylsilane (850 mg, 6.05 mmol, 1.20 equiv), CuI (0.19 g, 1.01 mmol, 0.20 equiv), $Et_3N$ (1.53 g, 15.15 mmol, 3 equiv) and $Pd(PPh_3)_2Cl_2$ (0.35 g, 0.51 mmol, 0.10 equiv) in DMF (45 mL) was stirred for 2 h at 50° C. under nitrogen atmosphere. The mixture was allowed to cool down to rt. The reaction was monitored by LCMS. The resulting mixture was diluted with water (450 mL). The resulting mixture was extracted with EtOAc (3×450 mL). The combined organic layers were washed with brine (3×450 mL), dried over anhydrous $Na_2SO_4$. After filtration, the filtrate was concentrated under reduced pressure. The residue was purified by silica gel column chromatography to afford ethyl 7-[2-(tert-butyldimethylsilyl)ethynyl]-6-oxo-5H-1,5-naphthyridine-3-carboxylate (1.5 g, 83%). LC-MS: (ES+H, m/z): $[M+H]^+$=357.2.

Step 7: Preparation of 3-[2-(tert-butyldimethylsilyl)ethynyl]-7-(hydroxymethyl)-1H-1,5-naphthyridin-2-one To a stirred mixture of ethyl 7-[2-(tert-butyldimethylsilyl)ethynyl]-6-oxo-5H-1,5-naphthyridine-3-carboxylate (1.20 g, 3.37 mmol, 1.00 equiv) in THF (30 mL) was added LiEt3BH (13.46 mL, 13.46 mmol, 4.00 equiv, 1M in THF) dropwise at 0° C. under nitrogen atmosphere. The resulting mixture was stirred for 1h at 0° C. under nitrogen atmosphere. The reaction was monitored by LCMS. The reaction was quenched by the addition of citric acid (5.05 mL, 5.05 mmol, 1.50 equiv, 1 M) at 0° C. The resulting mixture was concentrated under reduced pressure. The residue was purified by silica gel column chromatography to afford 3-[2-(tert-butyldimethylsilyl)ethynyl]-7-(hydroxymethyl)-1H-1,5-naphthyridin-2-one (840 mg, 79%). LC-MS: (ES+H, m/z): [M+H]$^+$=315.0.

Step 8: Preparation of 3-[2-(tert-butyldimethylsilyl)ethynyl]-7-(chloromethyl)-1H-1,5-naphthyridin-2-one To a stirred mixture of 3-[2-(tert-butyldimethylsilyl)ethynyl]-7-(hydroxymethyl)-1H-1,5-naphthyridin-2-one (92 mg, 0.29 mmol, 1.00 equiv) and DMF (1 mg, 0.01 mmol, 0.05 equiv) in DCM (5 mL) was added SOCl$_2$ (0.06 mL, 0.88 mmol, 3.00 equiv, 1.64 g/mL) dropwise at 0° C. under nitrogen atmosphere. The resulting mixture was stirred overnight at rt under nitrogen atmosphere. The reaction was monitored by LCMS. The resulting mixture was concentrated under reduced pressure to afford 3-[2-(tert-butyldimethylsilyl)ethynyl]-7-(chloromethyl)-1H-1,5-naphthyridin-2-one (97 mg, crude). The crude product was used in the next step directly without further purification. LC-MS: (ES+H, m/z): [M+H+MeCN]$^+$=374.2.

Step 9: Preparation of 5-[4-({7-[2-(tert-butyldimethylsilyl)ethynyl]-6-oxo-5H-1,5-naphthyridin-3-yl}methyl)piperazin-1-yl]pyridine-2-carbonitrile To a stirred mixture of 5-(piperazin-1-yl)pyridine-2-carbonitrile hydrochloride (119 mg, 0.53 mmol, 1.48 equiv), DIEA (232 mg, 1.80 mmol, 5.00 equiv) and 3-[2-(tert-butyldimethylsilyl)ethynyl]-7-(chloromethyl)-1H-1,5-naphthyridin-2-one (120 mg, 0.36 mmol, 1.00 equiv) in MeCN (5 mL) was added KI (11 mg, 0.07 mmol, 0.20 equiv) portion wise at rt under nitrogen atmosphere. The resulting mixture was stirred for 2 h at 80° C. under nitrogen atmosphere. The reaction was monitored by LCMS. The resulting mixture was concentrated under reduced pressure. The residue was purified by silica gel column chromatography to afford 5-[4-({7-[2-(tert-butyldimethylsilyl)ethynyl]-6-oxo-5H-1,5-naphthyridin-3-yl}methyl)piperazin-1-yl]pyridine-2-carbonitrile (120 mg, 69%).

Step 10: Preparation of 5-{4-[(7-ethynyl-6-oxo-5H-1,5-naphthyridin-3-yl)methyl]piperazin-1-yl}pyridine-2-carbonitrile To a stirred mixture of 5-[4-({7-[2-(tert-butyldimethylsilyl)ethynyl]-6-oxo-5H-1,5-naphthyridin-3-yl}methyl)piperazin-1-yl]pyridine-2-carbonitrile (120 mg, 0.24 mmol, 1.00 equiv) in THF (2.5 mL) was added TBAF (0.27 mL, 0.27 mmol, 1.10 equiv) dropwise at rt under nitrogen atmosphere. The resulting mixture was stirred for 1h at rt under nitrogen atmosphere. The reaction was monitored by LCMS. The resulting mixture was concentrated under reduced pressure. The resulting mixture was diluted with water (50 mL). The resulting mixture was extracted with EtOAc (3×25 mL). The combined organic layers were washed with brine (1×50 mL), dried over anhydrous Na$_2$SO$_4$. After filtration, the filtrate was concentrated under reduced pressure. The crude product (120 mg) was purified by prep HPLC to afford 5-{4-[(7-ethynyl-6-oxo-5H-1,5-naphthyridin-3-yl)methyl]piperazin-1-yl}pyridine-2-carbonitrile (31.3 mg, 34%). LC-MS: (ES-H, m/z): [M-H]$^-$=369.1; $^1$H NMR (300 MHz, DMSO-d$_6$) δ 12.17 (s, 1H), 8.48 (d, 1H), 8.42 (d, 1H), 8.15 (s, 1H), 7.75 (d, 1H), 7.64 (d, 1H), 7.36 (dd, 1H), 4.51 (s, 1H), 3.67 (s, 2H), 3.47-3.38 (m, 4H), 2.60-2.52 (m, 4H).

Example 2

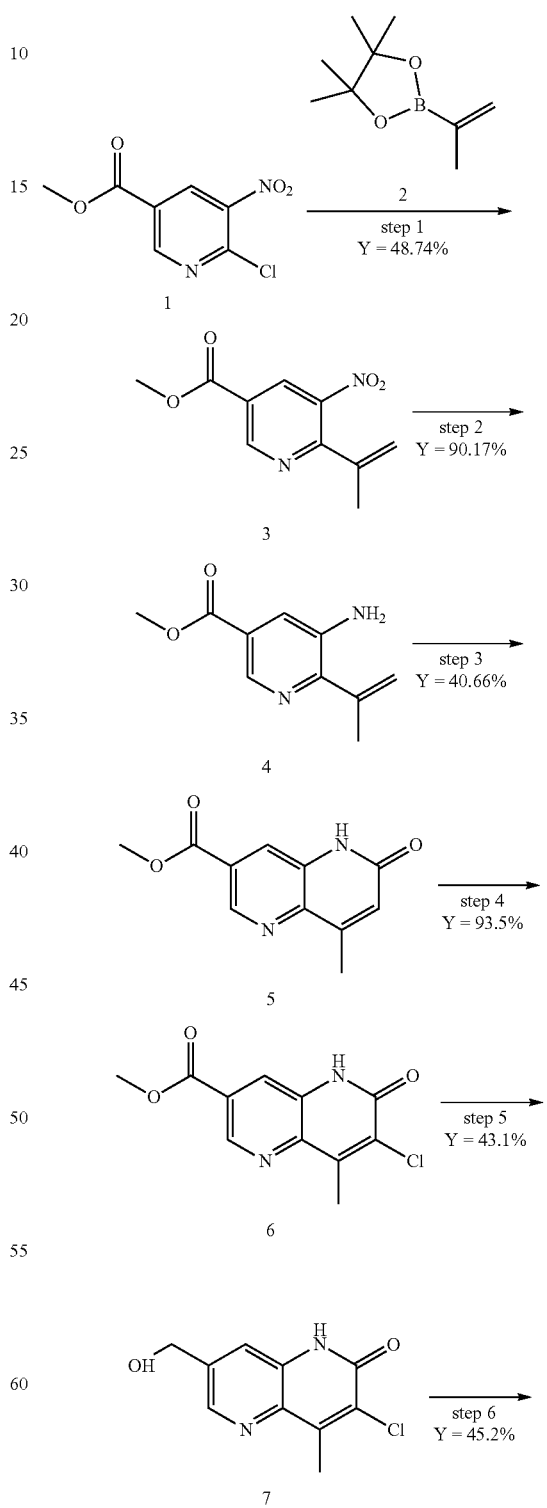

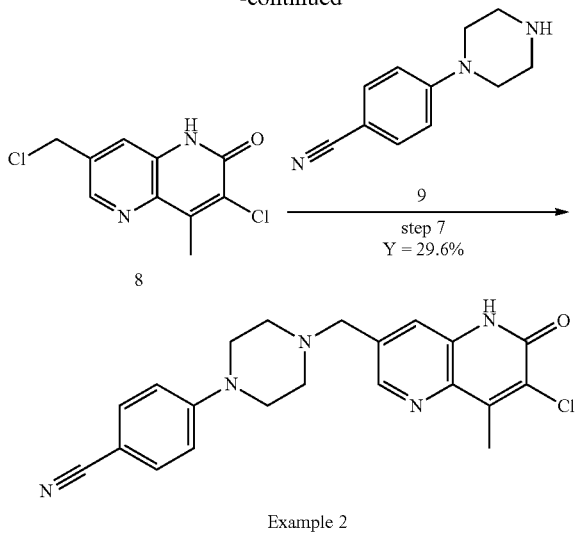

Example 2

Step 1: Preparation of methyl 5-nitro-6-(prop-1-en-2-yl)pyridine-3-carboxylate A mixture of methyl 6-chloro-5-nitropyridine-3-carboxylate (10.00 g, 46.17 mmol, 1.00 equiv.), 4,4,5,5-tetramethyl-2-(prop-1-en-2-yl)-1,3,2-dioxaborolane (15.52 g, 92.34 mmol, 2.00 equiv.), $K_2CO_3$ (12.76 g, 92.34 mmol, 2.00 equiv.) and Pd(dppf)Cl$_2$ (3.38 g, 4.62 mmol, 0.10 equiv.) in dioxane (150 mL) and water (15 mL) was stirred for 3 h at 100° C. under nitrogen atmosphere. The reaction was monitored by LCMS. The mixture was allowed to room temperature. The resulting mixture was diluted with water (300 mL) and extracted with EtOAc (3×300 mL). The combined organic layers were washed with sat. NaCl (aq.) (3×100 mL), dried over anhydrous $Na_2SO_4$, filtered and concentrated under reduced pressure. The filtrate was concentrated under reduced pressure. The residue was purified by silica gel column chromatography, eluted with PE/EA (1:1) to afford methyl 5-nitro-6-(prop-1-en-2-yl)pyridine-3-carboxylate (5.00 g, 48.74%) as a light yellow oil. LC-MS: (ES+H, m/z): [M+H]$^+$=222.95; $^1$H NMR (300 MHz, DMSO-d$_6$) δ 9.25 (d, 1H), 8.74 (d, 1H), 5.41-5.47 (m, 1H), 5.13-5.21 (M, 1H), 3.94 (s, 3H), 2.16 (dd, 3H).

Step 2: Preparation of methyl 5-nitro-6-(prop-1-en-2-yl)pyridine-3-carboxylate To a stirred solution of methyl 5-nitro-6-(prop-1-en-2-yl)pyridine-3-carboxylate (5.00 g, 22.50 mmol, 1.00 equiv.) in MeOH (100 mL) were added NH$_4$Cl (25 mL, sat. aq.) and Fe (5.03 g, 90.01 mmol, 4.00 equiv.). The reaction was stirred at 80° C. for 4 h under nitrogen atmosphere. The reaction was monitored by LCMS. The mixture was allowed to room temperature then concentrated under reduced pressure. The residue was diluted with CH$_2$Cl$_2$/2-Propanol (5:1, 200 mL) and washed with water (250 mL) and brine (250 mL). The organic layers were dried over anhydrous Na$_2$SO$_4$, filtered and concentrated under reduced pressure. This resulted in methyl 5-amino-6-(prop-1-en-2-yl)pyridine-3-carboxylate (3.90 g, 90.17%) which was used directly without further purification. LC-MS: (ES+H, m/z): [M+H]$^+$=193.15; $^1$H NMR (300 MHz, DMSO-d$_6$) δ 8.29 (d, 1H), 7.60 (d, 1H), 5.51-5.47 (m, 1H), 5.41 (s, 2H), 5.39-5.36 (m, 1H), 3.84 (s, 3H), 2.08 (t, 3H).

Step 3: Preparation of methyl 8-methyl-6-oxo-5H-1,5-naphthyridine-3-carboxylate A solution of triphosgene (1.54 g, 5.20 mmol, 0.50 equiv.) in toluene (20 mL) was added to the solution of methyl 5-amino-6-(prop-1-en-2-yl)pyridine-3-carboxylate (3.90 g, 20.29 mmol, 1.00 equiv.) and Et$_3$N (6.16 g, 60.87 mmol, 3.00 equiv.) in toluene (40 mL) at 0° C. under nitrogen atmosphere. The resulting mixture was stirred overnight at 60° C. under nitrogen. The reaction was monitored by LCMS. The reaction was quenched with MeOH (30 mL) at 0° C. The resulting mixture was diluted with water (200 mL) and extracted with CH$_2$Cl$_2$/2-Propanol (5:1, 3×200 mL). The combined organic layers were washed with water (3×100 mL), dried over anhydrous Na$_2$SO$_4$, filtered and concentrated under reduced pressure. The residue was purified by silica gel column chromatography to afford methyl 8-methyl-6-oxo-5H-1,5-naphthyridine-3-carboxylate (1.80 g, 40.66%). LC-MS: (ES+H, m/z): [M+H]$^+$=219.1; $^1$H NMR (400 MHz, DMSO-d$_6$) δ 11.92 (s, 1H), 8.92 (d, 1H), 8.15 (d, 1H), 6.79 (s, 1H), 3.93 (s, 3H), 2.48 (s, 3H).

Step 4: Preparation of methyl 7-chloro-8-methyl-6-oxo-5H-1,5-naphthyridine-3-carboxylate To a solution of methyl 8-methyl-6-oxo-5H-1,5-naphthyridine-3-carboxylate (600 mg, 2.75 mmol, 1.00 equiv.) and NCS (587 mg, 4.40 mmol, 1.60 equiv.) in CH$_3$COOH (7 mL) was added 2,2-dichloroacetic acid (71 mg, 0.55 mmol, 0.20 equiv.) dropwise at room temperature under nitrogen atmosphere. The resulting mixture was stirred overnight at 100° C. under nitrogen atmosphere. The reaction was monitored by LCMS. The mixture was allowed to cool down to room temperature. The resulting mixture was concentrated under reduced pressure. The residue was purified by silica gel column chromatography to afford methyl 7-chloro-8-methyl-6-oxo-5H-1,5-naphthyridine-3-carboxylate (650 mg, 93.5%). LC-MS: (ES+H, m/z): [M+H]$^+$=253.0; $^1$H NMR (300 MHz, DMSO-d$_6$) δ 8.90 (d, 1H), 8.13 (d, 1H), 3.93 (s, 3H), 2.60 (s, 3H).

Step 5: Preparation of 3-chloro-7-(hydroxymethyl)-4-methyl-1H-1,5-naphthyridin-2-one To a stirred solution of methyl 7-chloro-8-methyl-6-oxo-5H-1,5-naphthyridine-3-carboxylate (600 mg, 2.38 mmol, 1.00 equiv.) in THF (5 mL) was added LiAlH$_4$ (2 mL, 2.5 M in THF, 4.75 mmol, 2.00 equiv.) dropwise at 0° C. under nitrogen atmosphere. The resulting mixture was stirred for 1 h at room temperature under nitrogen atmosphere. The reaction was monitored by LCMS. The reaction was quenched by the addition of HCl (1 mL, 12M) at 0° C. The resulting mixture was concentrated under reduced pressure. The residue was purified by silica gel column chromatography to afford 3-chloro-7-(hydroxymethyl)-4-methyl-1H-1,5-naphthyridin-2-one (230 mg, 43.1%). LC-MS: (ES+H, m/z): [M+H]$^+$=225.1; $^1$H NMR (300 MHz, DMSO-d$_6$) δ 12.24 (br, 1H), 8.48 (d, 1H), 7.77 (d, 1H), 5.69 (s, 1H), 4.63 (s, 2H), 2.63 (s, 3H).

Step 6: Preparation of 3-chloro-7-(chloromethyl)-4-methyl-1H-1,5-naphthyridin-2-one To a stirred solution of 3-chloro-7-(hydroxymethyl)-4-methyl-1H-1,5-naphthyridin-2-one (200 mg, 0.89 mmol, 1.00 equiv.) and DMF (7 mg, 0.09 mmol, 0.10 equiv.) in DCM (10 mL) were added SOCl$_2$ (318 mg, 2.67 mmol, 3.00 equiv.) dropwise at 0° C. under nitrogen atmosphere. The resulting mixture was stirred for 10 h at room temperature. The reaction was monitored by LCMS. The resulting mixture was concentrated under reduced pressure. The residue was purified by silica gel column chromatography to afford 3-chloro-7-(chloromethyl)-4-methyl-1H-1,5-naphthyridin-2-one (98 mg, 45.2%). LC-MS: (ES+H, m/z): [M+H]$^+$ =243.0.

Step 7: Preparation of 4-{4-[(7-chloro-8-methyl-6-oxo-5H-1,5-naphthyridin-3-yl)methyl]piperazin-1-yl}benzonitrile A solution of 3-chloro-7-(chloromethyl)-4-methyl-1H-1,5-naphthyridin-2-one (25 mg, 0.10 mmol, 1.00 equiv.), DIEA (66 mg, 0.51 mmol, 5.00 equiv.), KI (4 mg, 0.02 mmol, 0.20 equiv.) and 4-(piperazin-1-yl)benzonitrile (19 mg, 0.10 mmol, 1.00 equiv.) in MeCN (2 mL) was stirred for 2 h at 80° C. under nitrogen atmosphere. The mixture was allowed to cool down to room temperature. The reaction was monitored by LCMS. The resulting mixture was concentrated under reduced pressure. The residue was purified by silica gel column chromatography. The resulting mixture was concentrated under reduced pressure. The pure fraction was concentrated then lyophilized to afford 4-{4-[(7-chloro-8-methyl-6-oxo-5H-1,5-naphthyridin-3-yl)methyl]piperazin-1-yl}benzonitrile (12 mg, 29.6%). LC-MS: (ES-H, m/z): [M-H]—=392.15; $^1$H NMR (400 MHz, DMSO-d$_6$) δ 12.30 (s, 1H), 8.51 (d, J=1.8 Hz, 1H), 7.69 (d, J=1.9 Hz, 1H), 7.58 (d, J=8.7 Hz, 2H), 7.02 (d, J=8.7 Hz, 2H), 3.67 (s, 2H), 3.38-3.34 (m, 4H), 2.64 (s, 3H), 2.57-2.54 (M, 4H).

Example 3

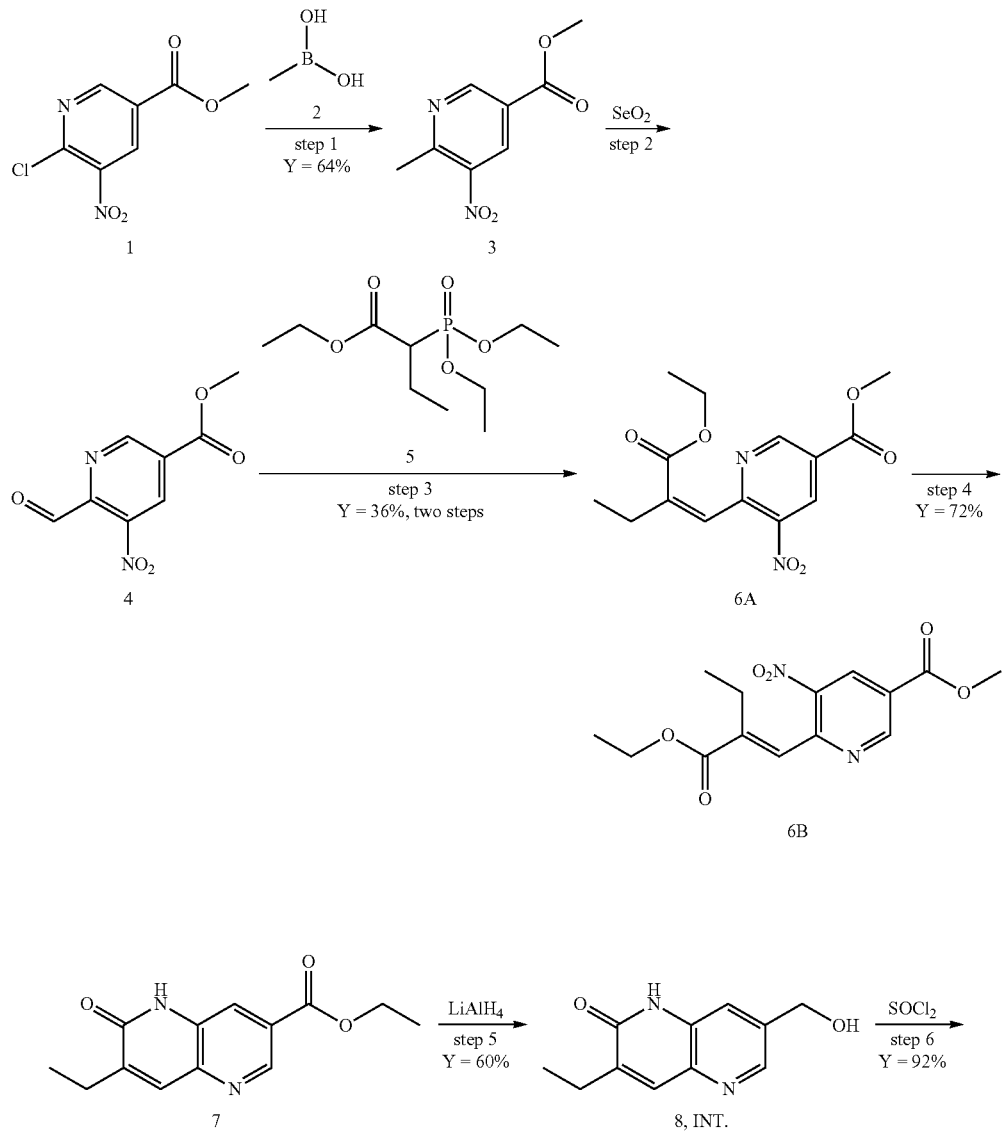

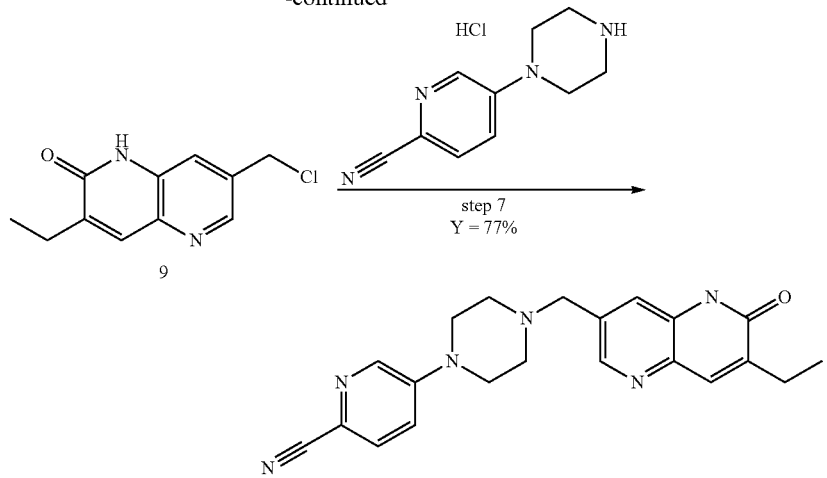

Example 3

Step 1: Preparation of methyl 6-methyl-5-nitropyridine-3-carboxylate

To a stirred mixture of methyl 6-chloro-5-nitropyridine-3-carboxylate (5 g, 273.08 mmol, 1.00 equiv) and methylboronic acid (2.75 g, 46.17 mmol, 2.00 equiv) in Toluene (60 mL) and H$_2$O (3 mL) were added Pd(dppf)Cl$_2$ (0.83 g, 1.15 mmol, 0.05 equiv) and CsF (7 g, 46.17 mmol, 2.00 equiv) at rt under nitrogen atmosphere. The resulting mixture was stirred overnight at 100° C. under nitrogen atmosphere. The resulting mixture was added to 500 mL water and extracted with EtOAc (3×200 mL). The combined organic layers were washed with brine (200 mL), dried over anhydrous Na$_2$SO$_4$, filtered and concentrated. The crude product was purified by silica gel column chromatography to afford methyl 6-methyl-5-nitropyridine-3-carboxylate (2.9 g, 64%). LC-MS: (ES+H, m/z): [M+H]$^+$=197.0; 1H NMR (400 MHz, Chloroform-d) δ 9.29 (d, 1H), 8.84 (d, 1H), 4.01 (s, 3H), 2.94 (s, 3H).

Step 2: Preparation of methyl 6-formyl-5-nitropyridine-3-carboxylate

A mixture of methyl 6-methyl-5-nitropyridine-3-carboxylate (35 g, 178.42 mmol, 1.00 equiv) and SeO$_2$ (30 g, 267.64 mmol, 1.50 equiv) in dioxane (200 mL) was stirred overnight at 110° C. under nitrogen atmosphere. The resulting mixture was then filtered and the filter cake was washed with EtOAc (5×200 mL). The filtrate was concentrated under reduced pressure and then the crude product was dissolved in THF (200 mL). The resulting mixture was filtered and the filter cake was washed with THF (3×100 mL). The filtrate was concentrated under reduced pressure to afford nitropyridine-3-carboxylate (40 g, crude). LC-MS: (ES+H, m/z): [M+H]$^+$=211.1.

Step 3: Preparation of methyl (Z)-6-(2-(ethoxycarbonyl)but-1-en-1-yl)-5-nitronicotinate To a stirred solution of NaH (11.42 g, 285.52 mmol, 1.50 equiv, 60% wt) in THF (500 mL) was added ethyl 2-(diethoxyphosphoryl)butanoate (72 g, 285.52 mmol, 1.50 equiv) in THF (50 mL) dropwise at 0° C. under nitrogen atmosphere. The resulting mixture was stirred for 10 min at 0° C. and then warmed to 40° C. and stirred for 10 min under nitrogen atmosphere. The resulting mixture was cooled to −78° C. and then methyl 6-formyl-5-nitropyridine-3-carboxylate (40 g, 190.35 mmol, 1.00 equiv) in THF (50 mL) was added dropwise. The resulting mixture was stirred for 30 min at −78° C. under nitrogen atmosphere. The reaction was monitored by LCMS. The reaction was quenched by the addition of sat. NH$_4$Cl (aq.) (100 mL) at 0° C. The resulting mixture was added 400 mL water and extracted with EtOAc (3×500 mL). The combined organic layers were washed with brine (1×500 mL), dried over anhydrous Na$_2$SO$_4$, filtered and concentrated. The residue was purified by silica gel column chromatography to afford methyl (Z)-6-(2-(ethoxycarbonyl)but-1-en-1-yl)-5-nitronicotinate (20 g, 36%, two steps) and methyl (E)-6-(2-(ethoxycarbonyl)but-1-en-1-yl)-5-nitronicotinate (8.8 g). Data for methyl (Z)-6-(2-(ethoxycarbonyl)but-1-en-1-yl)-5-nitronicotinate: LC-MS: (ES+H, m/z): [M+H]$^+$=309.1; 1 H NMR (300 MHz, Chloroform-d) δ 9.27 (d, 1H), 8.88 (d, 1H), 7.10 (t, 1H), 4.22-4.16 (m, 2H), 4.03 (s, 3H), 2.59 (qd, 2H), 1.25 (t, 3H), 1.19 (t 3H). Data for methyl (E)-6-(2-(ethoxycarbonyl)but-1-en-1-yl)-5-nitronicotinate: LC-MS: (ES+H, m/z): [M+H]$^+$=309.1; $^1$H NMR (300 MHz, Chloroform-d) δ 9.45 (d, 1H), 8.88 (d, 1H), 7.87 (s, 11H), 4.34 (q, 2H), 4.05 (s, 3H), 2.67 (q, 2H), 1.39 (t, 3H), 1.15 (t, 3H).

Step 4: Preparation of ethyl 7-ethyl-6-oxo-5H-1,5-naphthyridine-3-carboxylate To a stirred mixture of methyl 6-[(1Z)-3-ethoxy-2-ethyl-3-oxoprop-1-en-1-yl]-5-nitropyridine-3-carboxylate (9.00 g, 29.19 mmol, 1.00 equiv) and Fe (16.30 g, 291.93 mmol, 10.00 equiv) in EtOH (200 mL) was added CaCl$_2$ (19.44 g, 175.16 mmol, 6.00 equiv) at rt under nitrogen atmosphere. The resulting mixture was stirred overnight at 90° C. under nitrogen atmosphere. The reaction was monitored by LCMS. The resulting mixture was filtered and the filter cake was washed with EtOAc (5×100 mL) and the combined filtrate was concentrated. The resulting mixture was added to 250 mL water and extracted with EtOAc (3×250 mL). The combined organic layers were washed with brine (1×250 mL), dried over anhydrous Na$_2$SO$_4$. After filtration, the filtrate was concentrated under reduced pressure to afford ethyl 7-ethyl-6-oxo-5H-1,5-naphthyridine-3-carboxylate (5.2 g, 72%). LC-MS: (ES+H, m/z): [M+H]⁺=247.1; 1H NMR (400 MHz, DMSO-d₆) δ 12.06 (s, 1H), 8.90 (s, 1H), 8.16 (s, 1H), 7.83 (s, 1H), 4.38 (q, 2H), 2.58 (q, 2H), 1.36 (t, 3H), 1.20 (t, 3H).

Step 5: Preparation of 3-ethyl-7-(hydroxymethyl)-1H-1,5-naphthyridin-2-one

To a stirred solution of ethyl 7-ethyl-6-oxo-5H-1,5-naphthyridine-3-carboxylate (4.00 g, 16.24 mmol, 1.00 equiv) in THF (50 mL) was added LiAlH₄ (13 mL, 32.49 mmol, 2.00 equiv, 2.5M in THF) dropwise at 0° C. under nitrogen atmosphere. The resulting mixture was stirred for 1 h at 0° C. The reaction was monitored by LCMS. The reaction was quenched by the addition of 1M aq HCl (16 mL) at 0° C. The resulting mixture was concentrated under reduced pressure and the crude product was purified by silica gel column chromatography to afford 3-ethyl-7-(hydroxymethyl)-1H-1,5-naphthyridin-2-one (2.00 g, 60%). LC-MS: (ES+H, m/z): [M+H]⁺=204.8; 1H NMR (400 MHz, DMSO-d₆) δ 11.91 (s, 1H), 8.38 (d, 1H), 7.74 (s, 1H), 7.62 (d, 1H), 5.49 (t, 1H), 4.62 (d, 2H), 2.55 (dd, 2H), 1.18 (t, 3H).

Step 6: Preparation of 7-(chloromethyl)-3-ethyl-1H-1,5-naphthyridin-2-one

To a stirred mixture of 3-ethyl-7-(hydroxymethyl)-1H-1,5-naphthyridin-2-one (300 mg, 1.47 mmol, 1.00 equiv) and DMF (11 mg, 0.15 mmol, 0.10 equiv) in DCM (10 mL) was added SOCl₂ (1.05 g, 8.81 mmol, 6.00 equiv) dropwise at 0° C. under nitrogen atmosphere. The resulting mixture was stirred overnight at rt and then concentrated under vacuum. The residue was purified by silica gel column chromatography to afford 7-(chloromethyl)-3-ethyl-1H-1,5-naphthyridin-2-one (300 mg, 92%). LC-MS: (ES+H, m/z): [M+H]⁺=222.8; 1H NMR (400 MHz, DMSO-d₆) δ 11.99 (s, 1H), 8.50 (d, 1H), 7.76 (s, 1H), 7.70 (d, 1H), 4.93 (s, 2H), 2.56 (td, 2H), 1.19 (t, 3H).

Step 7: Preparation of 5-{4-[(7-ethyl-6-oxo-5H-1,5-naphthyridin-3-yl)methyl]piperazin-1-yl}pyridine-2-carbonitrile To a stirred mixture of 5-(piperazin-1-yl)pyridine-2-carbonitrile, HCl salt (600 mg) and 7-(chloromethyl)-3-ethyl-1H-1,5-naphthyridin-2-one (500 mg, 2.25 mmol, 1.00 equiv) in ACN (4 mL) were added DIEA (1.45 g, 11.25 mmol, 5.00 equiv) and KI (75 mg, 0.45 mmol, 0.20 equiv) in portions at rt. The resulting mixture was stirred for 1h at 80° C. under nitrogen atmosphere. The reaction was monitored by LCMS. The mixture was allowed to cool down to rt. The reaction was poured into water (20 mL). The aqueous layer was extracted with EtOAc (3×20 mL). The combined organic layers were concentrated under reduced pressure. The residue was purified by silica gel column chromatography to afford 5-{4-[(7-ethyl-6-oxo-5H-1,5-naphthyridin-3-yl)methyl]piperazin-1-yl}pyridine-2-carbonitrile (650 mg, 77%). LC-MS: (ES+H, m/z): [M+H]⁺=375.2; ¹H NMR (300 MHz, DMSO-d₆) δ 11.86 (s, 1H), 8.41-8.35 (m, 2H), 7.75 (t, 2H), 7.61 (s, 1H), 7.36 (dd, 1H), 3.64 (s, 2H), 3.52-3.42 (m, 4H), 2.61-2.54 (m, 6H), 1.18 (t, 3H).

Example 5

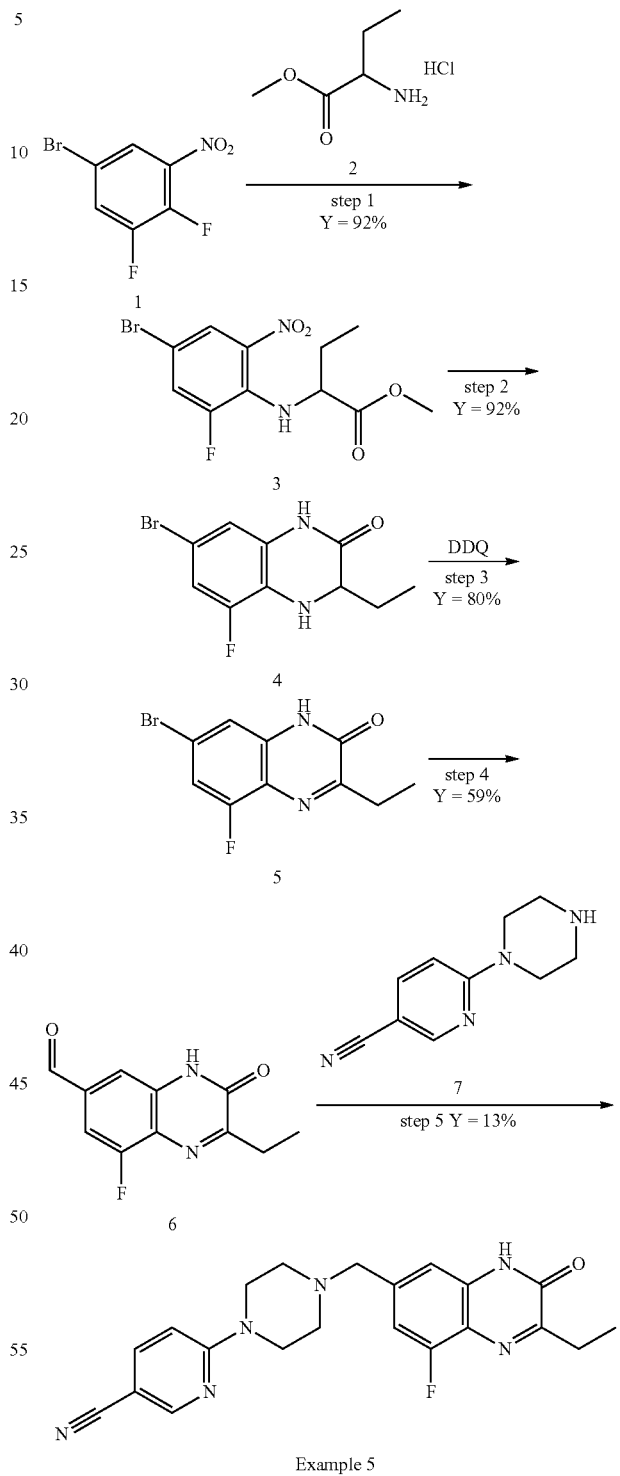

Example 5

Step 1: Preparation of methyl 2-[(4-bromo-2-fluoro-6-nitrophenyl)amino]butanoate To a stirred mixture of 5-bromo-1,2-difluoro-3-nitrobenzene (10.00 g, 42.02 mmol, 1.00 equiv) and Methyl 2-aminobutanoate hydrochloride (6.43 g, 42.02 mmol, 1.00 equiv) in NMP (200 mL) was added DIEA (27.15 g, 210.10 mmol, 5.00 equiv) dropwise at rt. The resulting mixture was diluted with water (500 mL). The resulting mixture was extracted with EtOAc (3×500 mL). The combined organic layers were washed with brine (8×300 mL), dried over anhydrous $Na_2SO_4$. After filtration, the filtrate was concentrated under reduced pressure. The residue was purified by silica gel column chromatography, the pure fraction was concentrated under vacuum to afford methyl 2-[(4-bromo-2-fluoro-6-nitrophenyl)amino]butanoate (13.00 g, 92%). LC-MS: (ES+H, m/z): $[M+H]^+$=334.9; $^1$H NMR (400 MHz, DMSO-$d_6$) δ 8.09 (t, 1H), 7.88 (dd, 1H), 7.79 (dd, 1H), 4.56 (dtd, 1H), 3.69 (s, 3H), 1.97-1.79 (m, 2H), 0.91 (t, 3H).

Step 2: Preparation of 7-bromo-3-ethyl-5-fluoro-3,4-dihydro-1H-quinoxalin-2-one

To a stirred mixture of Fe (5.00 g, 89.52 mmol, 5.00 equiv) in AcOH (100 mL) was added methyl 2-[(4-bromo-2-fluoro-6-nitrophenyl)amino]butanoate (6.00 g, 17.90 mmol, 1.00 equiv) in AcOH (20 mL) dropwise at 80° C. under nitrogen atmosphere. The resulting mixture was stirred for 2 h at 80° C. under nitrogen atmosphere. The reaction was monitored by TLC ($CH_2Cl_2$/MeOH=10/1). The mixture was allowed to cool down to rt. The resulting mixture was filtered, the filter cake was washed with EtOAc (3×50 mL). The filtrate was concentrated under reduced pressure. The residue was purified by trituration with water (3×100 mL). The precipitated solids were collected by filtration and washed with water (3×20 mL). This resulted in 7-bromo-3-ethyl-5-fluoro-3,4-dihydro-1H-quinoxalin-2-one (4.5 g, 92%). $^1$H NMR (400 MHz, DMSO-$d_6$) δ 10.52 (s, 1H), 6.99 (d, 1H), 6.72 (s, 1H), 6.17 (s, 1H), 3.78 (d, 1H), 1.72-1.62 (m, 2H), 0.88 (t, 3H).

Step 3: Preparation of 7-bromo-3-ethyl-5-fluoro-1H-quinoxalin-2-one

To a stirred solution of 7-bromo-3-ethyl-5-fluoro-3,4-dihydro-TH-quinoxalin-2-one (4.40 g, 16.11 mmol, 1.00 equiv) in DCM (100 mL) was added DDQ (4.39 g, 19.33 mmol, 1.20 equiv) in portions at rt under nitrogen atmosphere. The resulting mixture was stirred for 2 h at rt under nitrogen atmosphere. The reaction was monitored by LCMS. The reaction was quenched by the addition of sat. $NaHCO_3$ (aq.) (100 mL) at 0° C. The residue was purified by trituration with sat. $NaHCO_3$ (aq.) (5×100 mL). The precipitated solids were collected by filtration and washed with water (3×100 mL) to afford 7-bromo-3-ethyl-5-fluoro-1H-quinoxalin-2-one (3.50 g, 80%). LC-MS: (ES-H, m/z): [M–H]—=269.0; $^1$H NMR (400 MHz, DMSO-$d_6$) δ 12.51 (s, 1H), 7.44 (d, 1H), 7.24 (s, 1H), 2.79 (q, 2H), 1.21 (t, 3H).

Step 4: Preparation of 2-ethyl-8-fluoro-3-oxo-4H-quinoxaline-6-carbaldehyde

To a solution of 7-bromo-3-ethyl-5-fluoro-1H-quinoxalin-2-one (2.90 g, 10.70 mmol, 1.00 equiv) in Toluene (100 mL) was added TMEDA (1.49 g, 12.84 mmol, 1.20 equiv), bis(adamantan-1-yl)(butyl)phosphane (0.77 g, 2.14 mmol, 0.20 equiv), Pd(OAc)$_2$ (0.24 g, 1.07 mmol, 0.10 equiv) in a pressure tank. The mixture was purged with nitrogen for 5 min and then was pressurized to 30 atm with (CO:$H_2$=1:1). The mixture was stirred overnight at 100° C. The reaction was monitored by LCMS. The reaction mixture was cooled to rt and filtered to remove insoluble solids. The resulting mixture was concentrated under vacuum. The residue was purified by silica gel column chromatography, the pure fraction was concentrated under vacuum to afford 2-ethyl-8-fluoro-3-oxo-4H-quinoxaline-6-carbaldehyde (1.40 g, 59%). LC-MS: (ES-H, m/z): [M–H]—=219.0; $^1$H NMR (300 MHz, DMSO-$d_6$) δ 12.74 (s, 1H), 10.01 (d, 1H), 7.65-7.47 (m, 2H), 2.86 (q, 2H), 1.24 (t, 3H).

Step 5: Preparation of 6-(4-((2-ethyl-8-fluoro-3-oxo-3,4-dihydroquinoxalin-6-yl)methyl)piperazin-1-yl)nicotinonitrile To a stirred solution of 6-(piperazin-1-yl)pyridine-3-carbonitrile (200 mg, 1.06 mmol, 1.00 equiv) and 2-ethyl-8-fluoro-3-oxo-3,4-dihydroquinoxaline-6-carbaldehyde (304 mg, 1.38 mmol, 1.30 equiv) in THF (10 mL) was added Ti(OiPr)$_4$ (453 mg, 1.60 mmol, 1.50 equiv) at rt under nitrogen atmosphere. After 2 h, NaBH(AcO)$_3$ (901 mg, 4.25 mmol, 4.00 equiv) was added at 0° C. and the reaction was warmed to rt. After 2 h, the reaction was quenched by the addition of water (10 mL) at 0° C. The aqueous layer was extracted with EtOAc (5×30 mL). The combined organic phase was concentrated under reduced pressure and the crude product was purified by prep HPLC to afford 6-(4-((2-ethyl-8-fluoro-3-oxo-3,4-dihydroquinoxalin-6-yl)methyl)piperazin-1-yl)nicotinonitrile (56.1 mg, 13%). LC-MS: (ES+H, m/z): $[M+H]^+$=393.2; 1H NMR (300 MHz, DMSO-$d_6$) δ 12.43 (s, 1H), 8.48 (d, 1H), 7.85 (dd, 1H), 7.16-7.04 (m, 2H), 6.93 (d, 1H), 3.77-3.52 (m, 6H), 2.87-2.75 (m, 2H), 2.50-2.43 (m, 4H), 1.22 (t, 3H); $^{19}$F NMR (282 MHz, DMSO-d6) δ–125.38.

Example 12

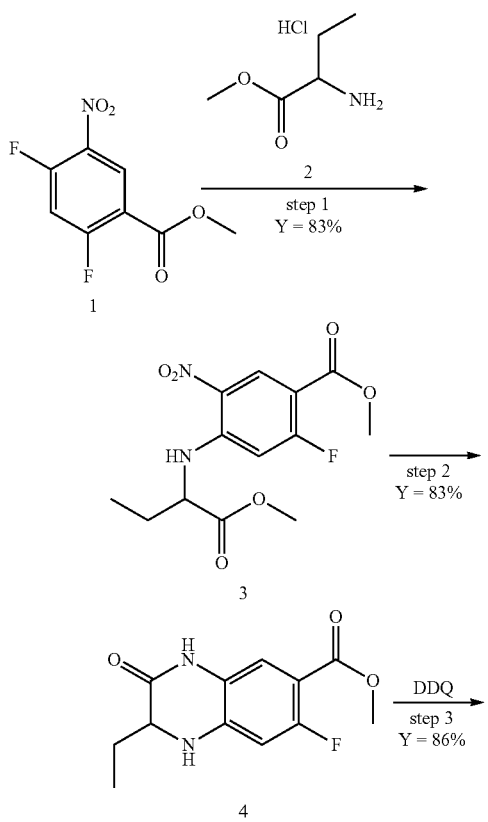

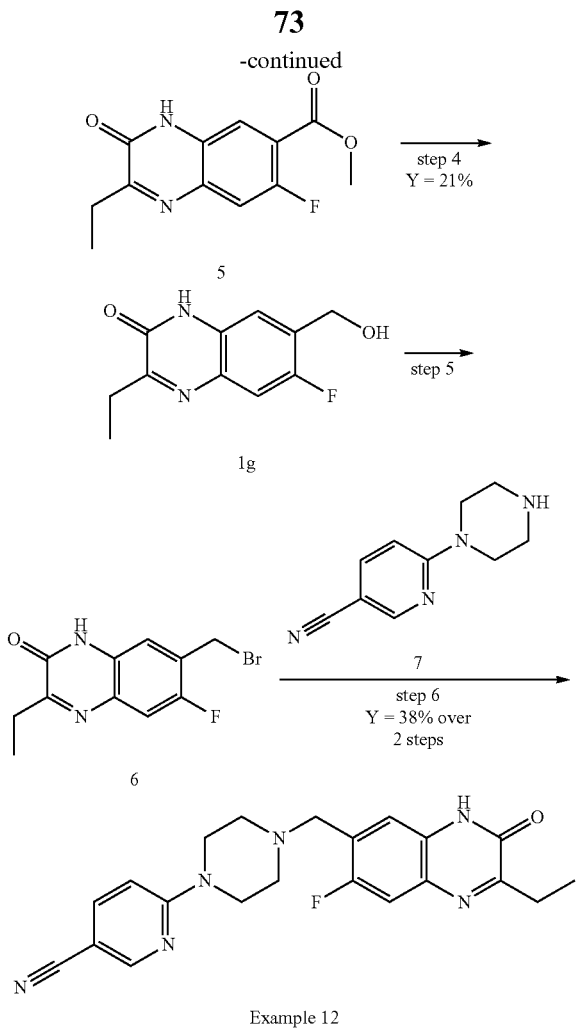

Example 12

Step 1: Preparation of methyl 2-fluoro-4-[(1-methoxy-1-oxobutan-2-yl)amino]-5-nitrobenzoate To a stirred mixture of methyl 2,4-difluoro-5-nitrobenzoate (10.00 g, 46.06 mmol, 1.00 equiv) and methyl 2-aminobutanoate, HCl salt (5.40 g, 46.06 mmol, 1.00 equiv) in NMP (100 mL) was added DIEA (48.1 mL, 276.34 mmol, 6.00 equiv) dropwise at rt under nitrogen atmosphere. The resulting mixture was stirred for 4 h at rt under nitrogen atmosphere. The reaction was monitored by LCMS. The reaction was quenched by the addition of water (200 mL) at rt. The resulting mixture was extracted with EtOAc (3×100 mL). The combined organic layers were washed with brine (8×200 mL), dried over anhydrous $Na_2SO_4$, filtered and concentrated. The crude product was purified by silica gel column chromatography to afford methyl 2-fluoro-4-[(1-methoxy-1-oxobutan-2-yl)amino]-5-nitrobenzoate (12 g, 83%). LC-MS: (ES+H, m/z): [M+H]$^+$=315.1; $^1$H NMR (400 MHz, DMSO-$d_6$) δ 8.80-8.56 (m, 2H), 7.21-6.99 (m, 1H), 4.84-4.74 (m, 1H), 3.85-3.81 (s, 3H), 3.77-3.74 (s, 3H), 2.05-1.82 (m, 2H), 0.91-0.85 (m, 3H).

Step 2: Preparation of methyl 2-ethyl-7-fluoro-3-oxo-2,4-dihydro-1H-quinoxaline-6-carboxylate To a stirred mixture of methyl 2-fluoro-4-[(1-methoxy-1-oxobutan-2-yl)amino]-5-nitrobenzoate (12.00 g, 38.18 mmol, 1.00 equiv) in MeOH (180 mL) and EtOAc (30 mL) was added Pd(OH)$_2$/C (2.40 g) portion-wise at rt under a nitrogen atmosphere. The resulting mixture was stirred overnight at rt under hydrogen atmosphere. The reaction was monitored by LCMS. Upon completion, the resulting mixture was filtered and the filter cake was washed with EtOAc (3×300 mL). The filtrate was concentrated and purified by silica gel column chromatography, (Pet. Ether/EtOAc) to afford methyl 2-ethyl-7-fluoro-3-oxo-2,4-dihydro-TH-quinoxaline-6-carboxylate (8 g, 83%). LC-MS: (ES+H, m/z): [M+H]$^+$=253.0; $^1$H NMR (400 MHz, DMSO-$d_6$) δ 10.44 (s, 1H), 7.25-7.20 (m, 1H), 7.19-7.14 (s, 1H), 4.00-3.91 (m, 1H), 3.75 (s, 3H), 1.76-1.60 (m, 2H), 0.94-0.86 (m, 3H).

Step 3: Preparation of methyl 2-ethyl-7-fluoro-3-oxo-4H-quinoxaline-6-carboxylate To a stirred mixture of methyl 2-ethyl-7-fluoro-3-oxo-2,4-dihydro-1H-quinoxaline-6-carboxylate (7.00 g, 27.75 mmol, 1.00 equiv) in DCM (70 mL) at rt was added DDQ (7.56 g, 33.30 mmol, 1.20 equiv) in DCM (70 mL). The resulting mixture was stirred for 2 h at rt under a nitrogen atmosphere. The reaction was monitored by LCMS. The residue was then dissolved in sat. aq. NaHCO$_3$ (200 mL). The precipitated solids were collected by filtration and washed with sat. aq. NaHCO$_3$ (3×200 mL) and water (3×200 mL). The solids were purified by trituration with EtOAc (30 mL)/hexane (100 mL). The resulting mixture was filtered, and the filter cake was washed with hexane (3×100 mL). The filter cake was dried under reduced pressure to afford methyl 2-ethyl-7-fluoro-3-oxo-4H-quinoxaline-6-carboxylate (6 g, 86%). LC-MS: (ES+H, m/z): [M+H]$^+$=251.1; $^1$H NMR (400 MHz, DMSO-$d_6$) δ 12.44 (s, 1H), 7.78 (d, 1H), 7.63 (d, 1H), 3.89 (s, 3H), 2.82 (q, 2H), 1.23 (t, 3H).

Step 4: Preparation of 3-ethyl-6-fluoro-7-(hydroxymethyl)-1H-quinoxalin-2-one To a stirred mixture of methyl 2-ethyl-7-fluoro-3-oxo-4H-quinoxaline-6-carboxylate (5.00 g, 19.98 mmol, 1.00 equiv) in THF (100 mL) was added LiAlH$_4$ (40 mL, 39.96 mmol, 2.00 equiv, 1 mol/L in THF) dropwise at 0° C. under nitrogen atmosphere. The reaction was monitored by LCMS. The reaction was quenched by the addition of water (1.5 mL), 15% NaOH (1.5 mL) and water (4.5 ml) at 0° C. The precipitated solids were collected by filtration and washed with water (3×30 mL). The solids were dissolved in water (500 mL) and EtOAc (200 mL). The resulting mixture was extracted with EtOAc (8×200 mL). The filtrate was concentrated under reduced pressure. The residue was purified by trituration with MeOH (5 mL) and EtOAc (20 ml). The resulting mixture was filtered and the filter cake was washed with EtOAc (3×10 mL). The solid was dried under reduced pressure to afford 3-ethyl-6-fluoro-7-(hydroxymethyl)-1H-quinoxalin-2-one (1.2 g, 27%). LC-MS: (ES+H, m/z): [M+H]$^+$=223.2; $^1$H NMR (400 MHz, DMSO-$d_6$) δ 12.38 (s, 1H), 7.48 (d, 1H), 7.41 (d, 1H), 5.52 (brs 1H), 4.64 (s, 2H), 2.80 (q, 2H), 1.18 (t, 3H).

Step 5: Preparation of 7-(bromomethyl)-3-ethyl-6-fluoro-1H-quinoxalin-2-one

To a stirred solution of 3-ethyl-6-fluoro-7-(hydroxymethyl)-1H-quinoxalin-2-one (150 mg, 0.68 mmol, 1.00 equiv) in HBr (4 mL, 33% wt in AcOH) at rt under nitrogen atmosphere. The resulting mixture was stirred for 1 h at 80° C. under nitrogen atmosphere. The reaction was monitored by LCMS. The mixture was allowed to cool down to rt. The resulting mixture was concentrated under reduced pressure. The crude product was used in the next step directly without further purification. LC-MS: (ES+H, m/z): [M+H]$^+$=285.0.

Step 6: Preparation of 6-{4-[(2-ethyl-7-fluoro-3-oxo-4H-quinoxalin-6-yl)methyl]piperazin-1-yl}pyridine-3-carbonitrile A mixture of 7-(bromomethyl)-3-ethyl-6-fluoro-1H-quinoxalin-2-one (190 mg, 0.67 mmol, 1.00 equiv), 6-(piperazin-1-yl)pyridine-3-carbonitrile (150 mg, 0.80 mmol, 1.20 equiv) and DIEA (431 mg, 3.33 mmol, 5.00 equiv) in NMP (5 mL) was stirred for 1 h at 80° C. under nitrogen atmosphere. The mixture was allowed to cool down to rt. The reaction was poured into Water (30 mL) and the aqueous layer was extracted with EtOAc (3×20 mL). The combined organic layers were concentrated under reduced pressure. The crude product (200 mg) was purified by prep HPLC to afford 6-{4-[(2-ethyl-7-fluoro-3-oxo-4H-quinoxalin-6-yl)methyl]piperazin-1-yl}pyridine-3-carbonitrile (100.2 mg, 38%). LC-MS: (ES+H, m/z): [M+H]$^+$=393.1; $^1$H NMR (300 MHz, DMSO-d$_6$) δ 12.31 (s, 1H), 8.48 (d, 1H), 7.85 (dd, 1H), 7.54 (d, 1H), 7.38 (d, 1H), 6.94 (d, 1H), 3.75-3.67 (m, 6H), 2.81 (q, 2H), 2.56-2.51 (m, 4H), 1.21 (t, 3H); $^{19}$F NMR (282 MHz, DMSO-d6) δ −124.28.

Example 16

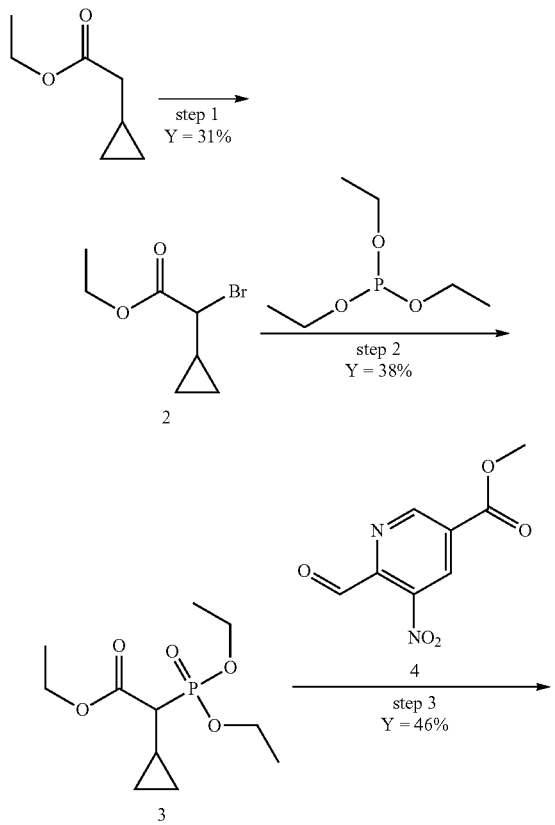

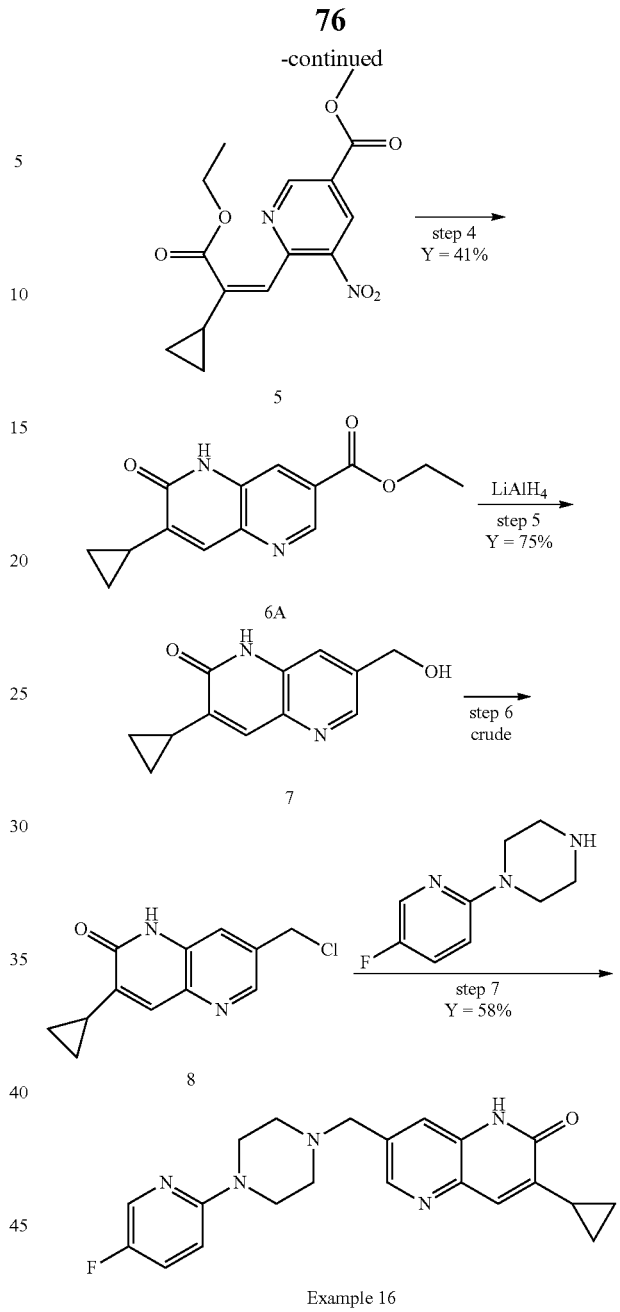

Example 16

Step 1: Preparation of ethyl 2-bromo-2-cyclopropylacetate

To a stirred solution of ethyl 2-cyclopropylacetate (10.00 g, 78.02 mmol, 1.00 equiv) in THF (100 mL) was added LDA (42.9 mL, 85.82 mmol, 1.10 equiv, 2.0 M in THF) dropwise at −78° C. under nitrogen atmosphere. The reaction was stirred for 1 hour then TMSCl (8.48 g, 78.02 mmol, 1.00 equiv) added dropwise and the reaction was stirred for 3 hours as it was warmed to rt. The reaction was cooled to −78° C. and NBS (15.28 g, 85.82 mmol, 1.10 equiv) in 50 mL THF added dropwise. The reaction was then stirred for 2 hours and allowed to warm to rt. The reaction was monitored by LCMS. The reaction was quenched by the addition of sat. NH$_4$Cl (aq.) (50 mL) at 0° C. The resulting mixture was extracted with Et$_2$O (3×200 mL). The combined organic layers were washed with brine (3×200 mL), dried over anhydrous Na$_2$SO$_4$. After filtration, the filtrate was concentrated under reduced pressure. The residue was purified by reversed phase combi-flash chromatography to afford ethyl 2-bromo-2-cyclopropylacetate (5.00 g, 310%). $^1$H NMR (300 MHz, Chloroform-d) δ 4.25 (q, 2H), 3.58 (d, 1H), 1.65-1.55 (m, 1H), 1.31 (t, 3H), 0.92-0.76 (m, 2H), 0.61-0.53 (m, 1H), 0.48-0.40 (m, 1H).

Step 2: Preparation of ethyl 2-cyclopropyl-2-(diethoxyphosphoryl)acetate

A solution of ethyl 2-bromo-2-cyclopropylacetate (5.00 g, 24.14 mmol, 1.00 equiv) and triethyl phosphite (5.22 g, 31.39 mmol, 1.30 equiv) was stirred for 24 h at 130° C. under a nitrogen atmosphere. The residue was purified by reversed phase combi-flash chromatography to afford ethyl 2-cyclopropyl-2-(diethoxyphosphoryl)acetate (2.40 g, 38%). $^1$H NMR (300 MHz, Chloroform-d) δ 4.26-4.07 (m, 6H), 2.19 (dd, 1H), 1.30 (dt 10H), 0.71 (dddd, 1H), 0.60 (ddddd, 1H), 0.47-0.37 (m, 1H), 0.24 (ddtd, 1H).

Step 3: Preparation of methyl 6-[(1Z)-2-cyclopropyl-3-ethoxy-3-oxoprop-1-en-1-yl]-5-nitropyridine-3-carboxylate To a stirred mixture of NaH (0.29 g, 7.14 mmol, 1.50 equiv, 60% wt) in THF (20 mL) was added ethyl 2-cyclopropyl-2-(diethoxyphosphoryl)acetate (1.89 g, 7.14 mmol, 1.50 equiv) dropwise at 0° C. under nitrogen atmosphere. The resulting mixture was stirred for 10 min at 0° C. and then warmed to 40° C. stirred for 10 min under nitrogen atmosphere. The resulting mixture was cooled to −78° C. followed by the addition of methyl 6-formyl-5-nitropyridine-3-carboxylate (1.00 g, 4.76 mmol, 1.00 equiv) in THF (20 mL) dropwise. The resulting mixture was stirred for 30 min at −78° C. under nitrogen atmosphere. The reaction was monitored by LCMS. The reaction was quenched by the addition of sat. NH$_4$Cl (aq.) (5 mL) at 0° C. The resulting mixture was added 20 mL water and extracted with EtOAc (3×20 mL). The combined organic layers were washed with brine (1×50 mL), dried over anhydrous Na$_2$SO$_4$. After filtration, the filtrate was concentrated under reduced pressure. The residue was purified by silica gel column chromatography to afford methyl 6-[(1Z)-2-cyclopropyl-3-ethoxy-3-oxoprop-1-en-1-yl]-5-nitropyridine-3-carboxylate (700 mg, 46%). LC-MS: (ES+H, m/z): [M+H]$^+$=320.8.

Step 4: Preparation of ethyl 7-cyclopropyl-6-oxo-5H-1,5-naphthyridine-3-carboxylate To a stirred mixture of methyl 6-[(1Z)-2-cyclopropyl-3-ethoxy-3-oxoprop-1-en-1-yl]-5-nitropyridine-3-carboxylate (600 mg, 1.87 mmol, 1.00 equiv) and Fe (1.04 g, 18.73 mmol, 10.00 equiv) in EtOH (10 mL) was added CaCl$_2$ (1.24 g, 11.24 mmol, 6.00 equiv) at rt under nitrogen atmosphere. The resulting mixture was stirred overnight at 90° C. under nitrogen atmosphere. The reaction was monitored by LCMS. The mixture was allowed to cool down to rt. The resulting mixture was filtered, the filter cake was washed with EtOAc (2×50 mL). The filtrate was concentrated under reduced pressure. The resulting mixture was added 50 mL water and extracted with EtOAc (2×50 mL). The combined organic layers were washed with brine (2×50 mL) and dried over anhydrous Na$_2$SO$_4$. After filtration, the filtrate was concentrated under reduced pressure. The residue was purified by silica gel column chromatography to afford ethyl 7-cyclopropyl-6-oxo-5H-1,5-naphthyridine-3-carboxylate (200 mg, 41%). LC-MS: (ES+H, m/z): [M+H]$^+$=259.0.

Step 5: Preparation of 3-cyclopropyl-7-(hydroxymethyl)-1H-1,5-naphthyridin-2-one To a stirred solution of ethyl 7-cyclopropyl-6-oxo-5H-1,5-naphthyridine-3-carboxylate (160 mg, 0.62 mmol, 1.00 equiv) was added LiAlH$_4$ (0.50 mL, 1.23 mmol, 2.00 equiv, 2.5M in THF) dropwise at 0° C. under nitrogen atmosphere. The resulting mixture was stirred for 1 h at 0° C. under nitrogen atmosphere. The reaction was monitored by LCMS. The reaction was quenched by the addition of 1M aq HCl (1 mL) at 0° C. The resulting mixture was concentrated under reduced pressure. The residue was purified by silica gel column chromatography to afford 3-cyclopropyl-7-(hydroxymethyl)-1H-1,5-naphthyridin-2-one (100 mg, 75%). LC-MS: (ES+H, m/z): [M+H]$^+$=217.2.

Step 6: Preparation of 7-(chloromethyl)-3-cyclopropyl-1H-1,5-naphthyridin-2-one

To a stirred mixture of 3-cyclopropyl-7-(hydroxymethyl)-1H-1,5-naphthyridin-2-one (80 mg, 0.37 mmol, 1.00 equiv) and DMF (3 mg, 0.04 mmol, 0.10 equiv) in DCM (10 mL) was added SOCl$_2$ (264 mg, 2.22 mmol, 6.00 equiv) dropwise at 0° C. under nitrogen atmosphere. The resulting mixture was stirred overnight at rt under nitrogen atmosphere. The reaction was monitored by LCMS. The resulting mixture was concentrated under reduced pressure to afford 7-(chloromethyl)-3-cyclopropyl-1H-1,5-naphthyridin-2-one. The crude product was used in the next step directly without further purification. LC-MS: (ES+H, m/z): [M+H]$^+$=235.0.

Step 7: Preparation of 3-cyclopropyl-7-{[4-(5-fluoropyridin-2-yl)piperazin-1-yl]methyl}-1H-1,5-naphthyridin-2-one To a stirred solution of 1-(5-fluoropyridin-2-yl)piperazine (100 mg, 0.55 mmol, 1.00 equiv) and 7-(chloromethyl)-3-cyclopropyl-1H-1,5-naphthyridin-2-one (130 mg, 0.55 mmol, 1.00 equiv) in ACN (3 mL) was added DIEA (357 mg, 2.76 mmol, 5.00 equiv) and KI (18 mg, 0.11 mmol, 0.20 equiv) at rt. The resulting mixture was stirred for 1 h at 80° C. under nitrogen atmosphere. The reaction was monitored by LCMS. The mixture was allowed to cool down to rt and then poured into H$_2$O (10 mL), The resulting mixture was extracted with EtOAc (3×10 mL). The combined organic layers were concentrated and the crude product was purified by prep HPLC to afford 3-cyclopropyl-7-{[4-(5-fluoropyridin-2-yl)piperazin-1-yl]methyl}-1H-1,5-naphthyridin-2-one (122.8 mg, 58%).LC-MS: (ES+H, m/z): [M+H]$^+$=380.3; $^1$H NMR (300 MHz, DMSO-d$_6$) δ 11.88 (s, 1H), 8.38 (d, 1H), 8.09 (d, 1H), 7.61 (d, 1H), 7.55-7.45 (m, 1H), 7.42 (s, 1H), 6.86 (dd, 1H), 3.62 (s, 2H), 3.49-2.38 (m, 4H), 2.50-2.45 (m, 4H), 2.20-2.08 (m, 1H), 1.02-0.92 (m, 2H), 0.86-0.78 (M, 2H); $^{19}$F NMR (282 MHz, DMSO-d6) δ−143.41.

Examples 28 and 29

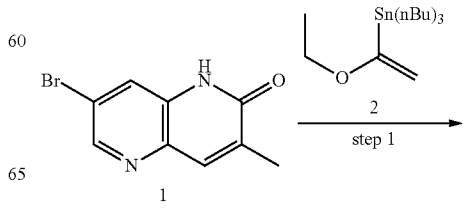

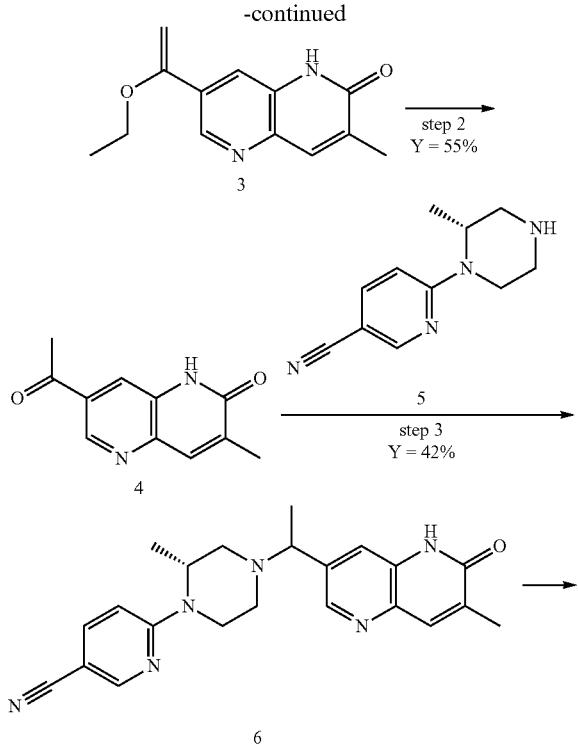

Example 28

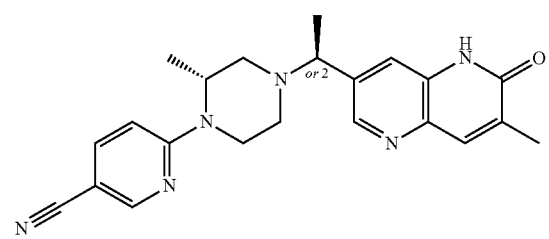

Example 29

Step 1: Preparation of 7-(1-ethoxyvinyl)-3-methyl-1,5-naphthyridin-2(1H)-one

To a stirred mixture of 7-bromo-3-methyl-1H-1,5-naphthyridin-2-one (3.00 g, 12.54 mmol, 1.00 equiv) and tributyl(1-ethoxyethenyl)stannane (13.60 g, 37.64 mmol, 3.00 equiv) in 1,4-dioxane (20 mL) was added Pd(PPh$_3$)$_2$Cl$_2$ (0.44 g, 0.62 mmol, 0.05 equiv) at rt. The resulting mixture was stirred for 2 h at 100° C. under nitrogen atmosphere. Upon completion, the reaction was cooled to rt and the resulting solution was used in the next step directly without further purification. LC-MS: (ES+H, m/z): [M+H]$^+$=231.1

Step 2: Preparation of 7-acetyl-3-methyl-1,5-naphthyridin-2(1H)-one

The solution of 7-(1-ethoxyvinyl)-3-methyl-1,5-naphthyridin-2(1H)-one from Step 1 was cooled to 0° C. and treated withed conc. HCl (4 mL) dropwise. The resulting reaction mixture was stirred for 2 h at rt and then basified to pH 8 with sat. NaHCO$_3$ (aq.). The resulting mixture was then diluted with water (100 mL) and extracted with CH$_2$Cl$_2$ (3×200 mL). The combined organic layers were washed with brine (1×300 mL), dried over anhydrous Na$_2$SO$_4$, filtered, and concentrated. The crude product was purified by silica gel column chromatography to afford 7-acetyl-3-methyl-1,5-naphthyridin-2(1H)-one (1.39 g, 55% over two steps). LC-MS: (ES+H, m/z): [M+H]$^+$=203.2

Step 3: Preparation of 6-[(2R)-2-methyl-4-[1-(7-methyl-6-oxo-5H-1,5-naphthyridin-3-yl)ethyl]piperazin-1-yl]pyridine-3-carbonitrile 7-acetyl-3-methyl-1H-1,5-naphthyridin-2-one (350 mg, 1.73 mmol, 1.00 equiv) was added to a solution 6-[(2R)-2-methylpiperazin-1-yl]pyridine-3-carbonitrile (455 mg, 2.25 mmol, 1.30 equiv) in CH$_2$Cl$_2$ (8 mL). The resulting mixture was then concentrated under reduced pressure. To the above mixture was added Ti(OiPr)$_4$ (4.6 mL, 15.58 mmol, 9.00 equiv) dropwise at rt. The resulting mixture was stirred for additional 4 h at 80° C. and then cooled to rt. To the above mixture was added EtOH (5 mL) and NaBH$_3$CN (217 mg, 3.46 mmol, 2.00 equiv) portion-wise at rt. The resulting mixture was stirred for an additional 2h at 80° C. and then cooled down to rt. The reaction mixture was poured into water (100 mL) and stirred for 1 h, filtered through a plug of Celite and washed with DCM/MeOH (3/1; 300 mL). The aqueous layer was extracted with DCM/i-PrOH (5/1; 2×100 mL) and the combined organic layers were washed with brine (2×50 mL), dried over Na$_2$SO$_4$., filtered and concentrated. The residue was purified by silica gel column chromatography to afford 6-[(2R)-2-methyl-4-[1-(7-methyl-6-oxo-5H-1,5-naphthyridin-3-yl)ethyl]piperazin-1-yl]pyridine-3-carbonitrile (280 mg, 41.6%). LC-MS: (ES-H, m/z): [M+H]$^+$=389.1. The diasteromers were separated by Chiral-HPLC to afford rel-6-[(2R)-2-methyl-4-[(1R*)-1-(7-methyl-6-oxo-5H-1,5-naphthyridin-3-yl)ethyl]piperazin-1-yl]pyridine-3-carbonitrile (Example 28 90.6 mg, de=100%) and rel-6-[(2R)-2-methyl-4-[(1R*)-1-(7-methyl-6-oxo-5H-1,5-naphthyridin-3-yl)ethyl]piperazin-1-yl]pyridine-3-carbonitrile (Example 29, 69.5 mg, de=100%). Data for Example 28: LC-MS: (ES+H, m/z): [M+H]$^+$=389.2; $^1$H NMR (300 MHz, DMSO-d$_6$) δ 11.90 (s, 1H), 8.48-8.43 (dd, 2H), 7.85-7.82 (m, 2H), 7.65-7.64 (d, 1H), 6.86-6.83 (d, 1H), 4.51 (s, 1H), 4.26-4.22 (d, 1H), 3.59-3.57 (q, 1H), 3.14-3.11 (m, 2H), 2.58-2.50 (d, 1H), 2.18-2.06 (m, 5H), 1.36-1.34 (d, 3H), 1.18-1.15 (d, 3H). Data for Example 29: LC-MS: (ES+H, m/z): [M+H]$^+$=389.1; $^1$H NMR (300 MHz, DMSO-d$_6$) δ 11.85 (s, 1H), 8.48-8.46 (dd, 2H), 7.85-7.81 (M, 2H), 7.66 (d, 1H), 6.86-6.83 (d, 1H), 4.62 (s, 1H), 4.16-4.12 (d, 1H), 3.70-3.64 (q, 1H), 3.11-3.01 (td, 1H), 2.88-2.76 (dd, 2H), 2.26-2.03 (m, 5H), 1.34 (d, 3H), 1.22 (d, 3H). The relative stereochemistry for Examples 28 and 29 was arbitrarily assigned.

Example 36

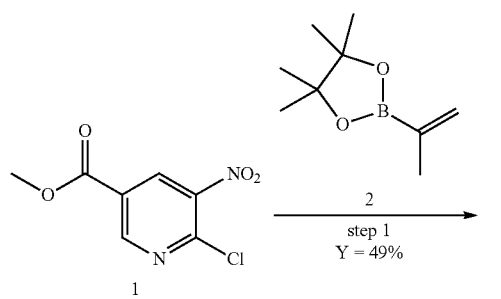
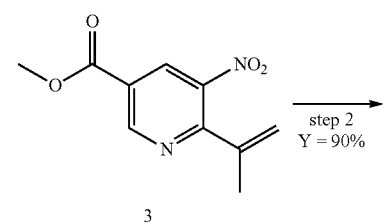
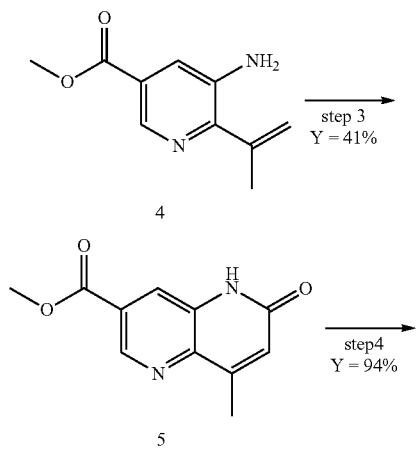
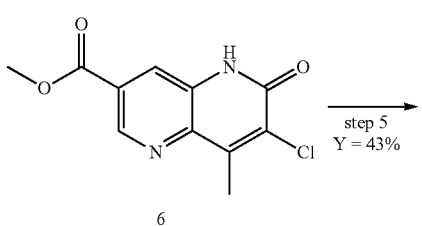
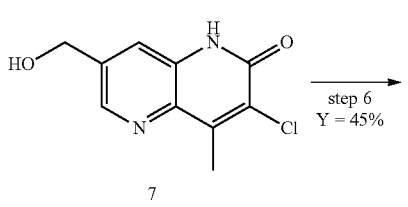
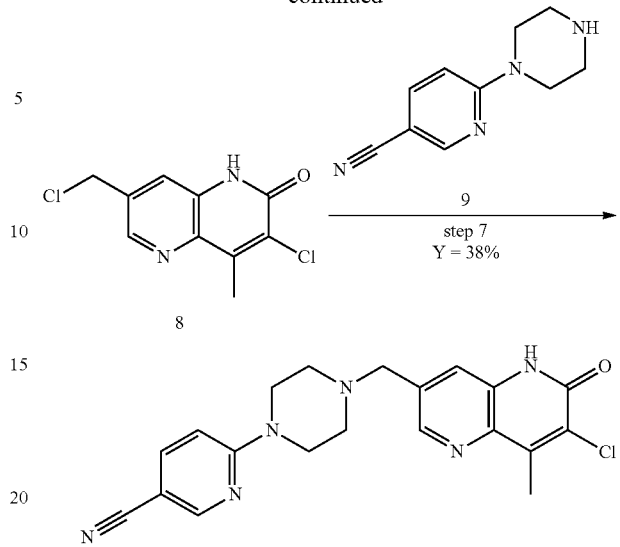

Example 36

Step 1: Preparation of methyl 5-nitro-6-(prop-1-en-2-yl)pyridine-3-carboxylate A mixture of methyl 6-chloro-5-nitropyridine-3-carboxylate (10.00 g, 46.17 mmol, 1.00 equiv), 4,4,5,5-tetramethyl-2-(prop-1-en-2-yl)-1,3,2-dioxaborolane (15.52 g, 92.34 mmol, 2.00 equiv), K2CO3 (12.76 g, 92.34 mmol, 2.00 equiv) and Pd(dppf)Cl2 (3.38 g, 4.62 mmol, 0.10 equiv) in dioxane (150 mL) and water (15 mL) was stirred for 3 h at 100° C. under nitrogen atmosphere. The reaction was monitored by LCMS. The mixture was allowed to rt. The resulting mixture was diluted with water (300 mL) and extracted with EtoAc (3×300 mL). The combined organic layers were washed with sat. NaCl (aq.) (3×100 mL), dried over anhydrous $Na_2SO_4$, filtered and concentrated under reduced pressure. The filtrate was concentrated under reduced pressure. The residue was purified by silica gel column chromatography to afford methyl 5-nitro-6-(prop-1-en-2-yl)pyridine-3-carboxylate (5.00 g, 49%) as alight yellow oil. LC-MS: (ES+H, m/z): [M+H]$^+$=222.95.

Step 2: Preparation of methyl 5-nitro-6-(prop-1-en-2-yl)pyridine-3-carboxylate To a stirred solution of methyl 5-nitro-6-(prop-1-en-2-yl)pyridine-3-carboxylate (5.00 g, 22.50 mmol, 1.00 equiv) in MeOH (100 mL) were added $NH_4Cl$ (25 mL, sat. aq.) and Fe (5.03 g, 90.01 mmol, 4.00 equiv). The reaction was stirred at 80° C. for 4 h under nitrogen atmosphere. The reaction was monitored by LCMS. The mixture was allowed to rt then concentrated under reduced pressure. The residue was diluted with $CH_2Cl_2$/2-Propanol (5:1, 200 mL) and washed with water (250 mL) and brine (250 mL). The organic layers were dried over anhydrous $Na_2SO_4$, filtered and concentrated under reduced pressure. This resulted in methyl 5-amino-6-(prop-1-en-2-yl)pyridine-3-carboxylate (3.90 g, 90%) which was used directly without further purification. LC-MS: (ES+H, m/z): [M+H]$^+$=193.15. $^1$H NMR (300 MHz, DMSO-$d_6$) δ 8.29 (d, 1H), 7.60 (d, 1H), 5.51-5.47 (m, 1H), 5.41 (s, 2H), 5.39-5.36 (m, 1H), 3.84 (s, 3H), 2.08 (t, 3H).

Step 3: Preparation of methyl 8-methyl-6-oxo-5H-1,5-naphthyridine-3-carboxylate A solution of triphosgene (1.54 g, 5.20 mmol, 0.50 equiv) in toluene (20 mL) was added to the solution of methyl 5-amino-6-(prop-1-en-2-yl)pyridine-3-carboxylate (3.90 g, 20.29 mmol, 1.00 equiv) and Et$_3$N (6.16 g, 60.87 mmol, 3.00 equiv) in toluene (40 mL) at 0° C. under nitrogen atmosphere. The resulting mixture was stirred overnight at 60° C. under nitrogen. The reaction was monitored by LCMS. The reaction was quenched with MeOH (30 mL) at 0° C. The resulting mixture was diluted with water (200 mL) and extracted with CH$_2$Cl$_2$/2-Propanol (5:1, 3×200 mL). The combined organic layers were washed with water (3×100 mL), dried over anhydrous Na$_2$SO$_4$, filtered and concentrated under reduced pressure. The residue was purified by silica gel column chromatography to afford methyl 8-methyl-6-oxo-5H-1,5-naphthyridine-3-carboxylate (1.80 g, 410%). LC-MS: (ES+H, m/z): [M+H]$^+$=219.1; $^1$H NMR (400 MHz, DMSO-d$_6$) δ 11.92 (s, 1H), 8.92 (d, 1H), 8.15 (d, 1H), 6.79 (s, 1H), 3.93 (s, 3H), 2.48 (s, 3H).

Step 4: Preparation of methyl 7-chloro-8-methyl-6-oxo-5H-1,5-naphthyridine-3-carboxylate To a solution of methyl 8-methyl-6-oxo-5H-1,5-naphthyridine-3-carboxylate (600 mg, 2.75 mmol, 1.00 equiv) and NCS (587 mg, 4.40 mmol, 1.60 equiv) in CH$_3$COOH (7 mL) was added 2,2-dichloroacetic acid (71 mg, 0.55 mmol, 0.20 equiv) dropwise at rt under nitrogen atmosphere. The resulting mixture was stirred overnight at 100° C. and then cooled to rt. The resulting mixture was concentrated under reduced pressure. The residue was purified by silica gel column chromatography to afford methyl 7-chloro-8-methyl-6-oxo-5H-1,5-naphthyridine-3-carboxylate (650 mg, 94%). LC-MS: (ES+H, m/z): [M+H]$^+$=253.0; $^1$H NMR (300 MHz, DMSO-d$_6$) δ 8.90 (d, 1H), 8.13 (d, 1H), 3.93 (s, 3H), 2.60 (s, 3H).

Step 5: Preparation of 3-chloro-7-(hydroxymethyl)-4-methyl-1H-1,5-naphthyridin-2-one To a stirred solution of methyl 7-chloro-8-methyl-6-oxo-5H-1,5-naphthyridine-3-carboxylate (600 mg, 2.38 mmol, 1.00 equiv) in THF (5 mL) was added LiAlH$_4$ (2 mL, 2.5 M in THF, 4.75 mmol, 2.00 equiv) dropwise at 0° C. under nitrogen atmosphere. The resulting mixture was stirred for 1 h at rt under nitrogen atmosphere. The reaction was monitored by LCMS. The reaction was quenched by the addition of HCl (1 mL, 12M) at 0° C. The resulting mixture was concentrated under reduced pressure. The residue was purified by silica gel column chromatography to afford 3-chloro-7-(hydroxymethyl)-4-methyl-1H-1,5-naphthyridin-2-one (230 mg, 43%). LC-MS: (ES+H, m/z): [M+H]$^+$=225.1; $^1$H NMR (300 MHz, DMSO-d$_6$) δ 12.24 (br, 1H), 8.48 (d, 1H), 7.77 (d, 1H), 5.69 (s, 1H), 4.63 (s, 2H), 2.63 (s, 3H).

Step 6: Preparation of 3-chloro-7-(chloromethyl)-4-methyl-1H-1,5-naphthyridin-2-one To a stirred solution of 3-chloro-7-(hydroxymethyl)-4-methyl-TH-1,5-naphthyridin-2-one (200 mg, 0.89 mmol, 1.00 equiv) and DMF (7 mg, 0.09 mmol, 0.10 equiv) in DCM (10 mL) were added SOCl2 (318 mg, 2.67 mmol, 3.00 equiv) dropwise at 0° C. under nitrogen atmosphere. The resulting mixture was stirred for 10 h at rt. The reaction was monitored by LCMS. The resulting mixture was concentrated under reduced pressure. The residue was purified by silica gel column chromatography to afford 3-chloro-7-(chloromethyl)-4-methyl-1H-1,5-naphthyridin-2-one (98 mg, 45%). LC-MS: (ES+H, m/z): [M+H]$^+$=243.0.

Step 7: Preparation of 6-{4-[(7-chloro-8-methyl-6-oxo-5H-1,5-naphthyridin-3-yl)methyl]piperazin-1-yl}pyridine-3-carbonitrile To a stirred mixture of 3-chloro-7-(chloromethyl)-4-methyl-1H-1,5-naphthyridin-2-one (85 mg, 0.35 mmol, 1.00 equiv) and 6-(piperazin-1-yl)pyridine-3-carbonitrile (66 mg, 0.35 mmol, 1.00 equiv) in ACN (1 mL) were added DIEA (136 mg, 1.05 mmol, 3.00 equiv) and KI (1 mg, 0.01 mmol, 0.10 equiv) at rt under nitrogen atmosphere. The resulting mixture was stirred for 1 h at 80° C. The reaction was monitored by LCMS. The mixture was allowed to cool down to rt. The resulting mixture was concentrated under reduced pressure. The residue was purified by silica gel column chromatography to afford the crude product (90 mg), which was further purified by prep HPLC to afford 6-{4-[(7-chloro-8-methyl-6-oxo-5H-1,5-naphthyridin-3-yl)methyl]piperazin-1-yl}pyridine-3-carbonitrile (52.5 mg, 28%). LC-MS: (ES+H, m/z): [M+H]$^+$=395.10; $^1$H NMR (300 MHz, DMSO-d$_6$) δ 12.30 (br, 1H), 8.50 (m, 2H), 7.85 (dd, 1H), 7.69 (d, 1H), 6.94 (d, 1H), 3.67-3.62 (m, 6H), 2.65 (s, 3H), 2.50-2.49 (m, 4H).

Example 42

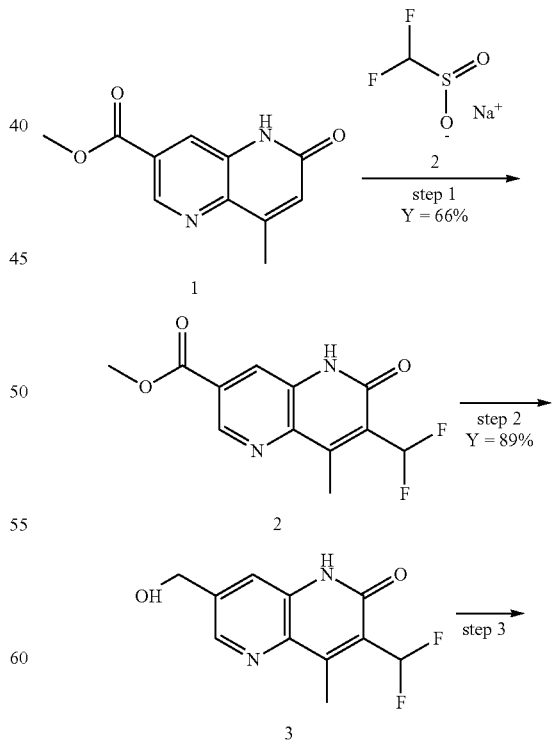

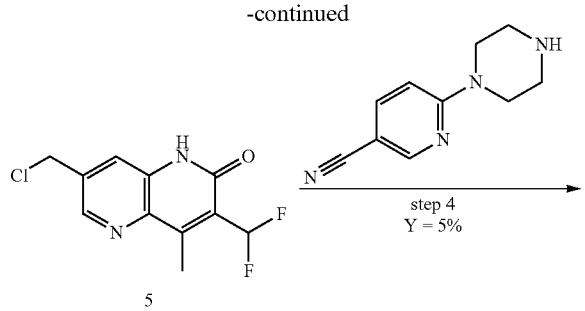

step 4
Y = 5%

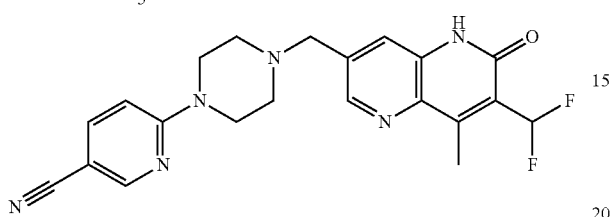

Example 42

Step 1: Preparation of methyl 7-(difluoromethyl)-8-methyl-6-oxo-5H-1,5-naphthyridine-3-carboxylate A mixture of methyl 8-methyl-6-oxo-5H-1,5-naphthyridine-3-carboxylate (800 mg, 3.67 mmol, 1.00 equiv), difluoromethanesulfinic acid sodium (1012 mg, 7.33 mmol, 2.00 equiv), 2-methylpropane-2-peroxol (991 mg, 11.00 mmol, 3.00 equiv) and TFA (418 mg, 3.67 mmol, 1.00 equiv) in CH2Cl2/H2O (2.5:1, 120 mL) was stirred overnight at rt under nitrogen atmosphere. The reaction was monitored by LCMS. The resulting mixture was then diluted with water (100 mL) and extracted with $CH_2Cl_2$/2-Propanol (5:1, 3×100 mL). The combined organic layers were washed with water (3×50 mL) and dried over anhydrous $Na_2SO_4$, filtered and concentrated under reduced pressure to afford methyl 7-(difluoromethyl)-8-methyl-6-oxo-5H-1,5-naphthyridine-3-carboxylate (650 mg, 66%). LC-MS: (ES+H, m/z): [M+H]$^+$=269.1; $^1$H NMR (400 MHz, DMSO-$d_6$) δ 12.39 (s, 1H), 8.99 (d, 1H), 8.19 (m, 1H), 7.26 (t 1H), 3.94 (s, 3H), 2.72 (s, 3H).

Step 2: Preparation of 3-(difluoromethyl)-7-(hydroxymethyl)-4-methyl-1H-1,5-naphthyridin-2-one To a stirred solution of methyl 7-(difluoromethyl)-8-methyl-6-oxo-5H-1,5-naphthyridine-3-carboxylate (650 mg, 2.42 mmol, 1.00 equiv) in THF (65 mL) was added LiAlH$_4$ solution (2.5M in THF, 3.9 mL, 9.75 mmol 4.00 equiv) dropwise at 0° C. under nitrogen atmosphere. The resulting mixture was stirred for 1 h at rt under nitrogen atmosphere. The reaction was monitored by LCMS. The reaction was quenched by the addition of saturated aqueous NH$_4$Cl (10 mL) at 0° C. and dried over anhydrous Na$_2$SO$_4$. The mixture was filtered and washed with CH$_2$Cl$_2$/MeOH (10:1, 100 mL) and the combined organic layers were concentrated under reduced pressure. The residue was purified by silica gel column chromatography to afford 3-(difluoromethyl)-7-(hydroxymethyl)-4-methyl-1H-1,5-naphthyridin-2-one (520 mg, 89%). LC-MS: (ES+H, m/z): [M+H]$^+$=241.1. $^1$H NMR (400 MHz, Methanol-d4) δ 8.58 (d, 1H), 7.73 (d, 1H), 7.20 (t, 1H), 4.79 (s, 2H), 2.81 (t, 3H).

Step 3: Preparation of 7-(chloromethyl)-3-(difluoromethyl)-4-methyl-1H-1,5-naphthyridin-2-one To a stirred mixture of 3-(difluoromethyl)-7-(hydroxymethyl)-4-methyl-1H-1,5-naphthyridin-2-one (320 mg, 1.33 mmol, 1.00 equiv) and DMF (5 mg, 0.07 mmol, 0.05 equiv) in CH$_2$Cl$_2$ (32 mL) was added SOCl2 (475 mg, 4.00 mmol, 3.00 equiv) dropwise at 0° C. under nitrogen atmosphere. The resulting mixture was stirred for 2 h at 50° C. under nitrogen atmosphere. The reaction was monitored by LCMS. The mixture was allowed to rt then concentrated under reduced pressure to afford 7-(chloromethyl)-3-(difluoromethyl)-4-methyl-1H-1,5-naphthyridin-2-one (crude, 400 mg). LC-MS: (ES+H, m/z): [M+H]$^+$=259.1

Step 4: Preparation of 6-(4-{[7-(difluoromethyl)-8-methyl-6-oxo-5H-1,5-naphthyridin-3-yl]methyl}piperazin-1-yl)pyridine-3-carbonitrile A mixture of 7-(chloromethyl)-3-(difluoromethyl)-4-methyl-1H-1,5-naphthyridin-2-one (380 mg, 1.47 mmol, 1.00 equiv), 6-(piperazin-1-yl)pyridine-3-carbonitrile (415 mg, 2.20 mmol, 1.50 equiv), KI (365 mg, 2.20 mmol, 1.50 equiv) and DIEA (569 mg, 4.40 mmol, 3.00 equiv) in MeCN (4 mL) was stirred for 1 h at 80° C. under nitrogen atmosphere. The reaction was monitored by LCMS. The mixture was allowed to rt. The resulting mixture was diluted with water (50 mL) and extracted with EtOAc (3×50 mL). The combined organic layers were washed with water (3×10 mL), dried over anhydrous Na$_2$SO$_4$. The mixture was filtered and washed with EtOAc (50 mL) and the filtrate was concentrated under reduced pressure. The residue was purified by prep HPLC to afford 6-(4-{[7-(difluoromethyl)-8-methyl-6-oxo-5H-1,5-naphthyridin-3-yl]methyl} piperazin-1-yl)pyridine-3-carbonitrile (31 mg, 5%). LC-MS: (ES+H, m/z): [M+H]$^+$=411.2; $^1$H NMR (300 MHz, DMSO-$d_6$) δ 12.17 (br, 1H), 8.57 (d, 1H), 8.41 (d, 1H), 7.85 (dd, 1H), 7.68 (d, 1H), 7.24 (t, 1H), 6.94 (d, 1H), 3.80-3.60 (m, 6H), 2.72 (s, 3H), 2.60-2.40 (m, 4H); $^{19}$F NMR (282 MHz, DMSO-$d_6$) δ–115.51.

Example 47

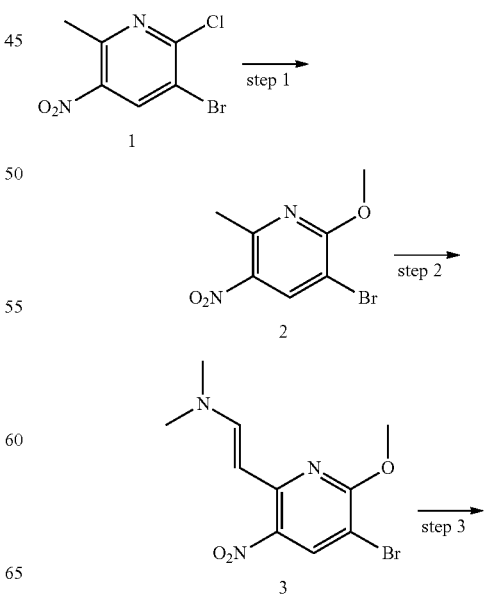

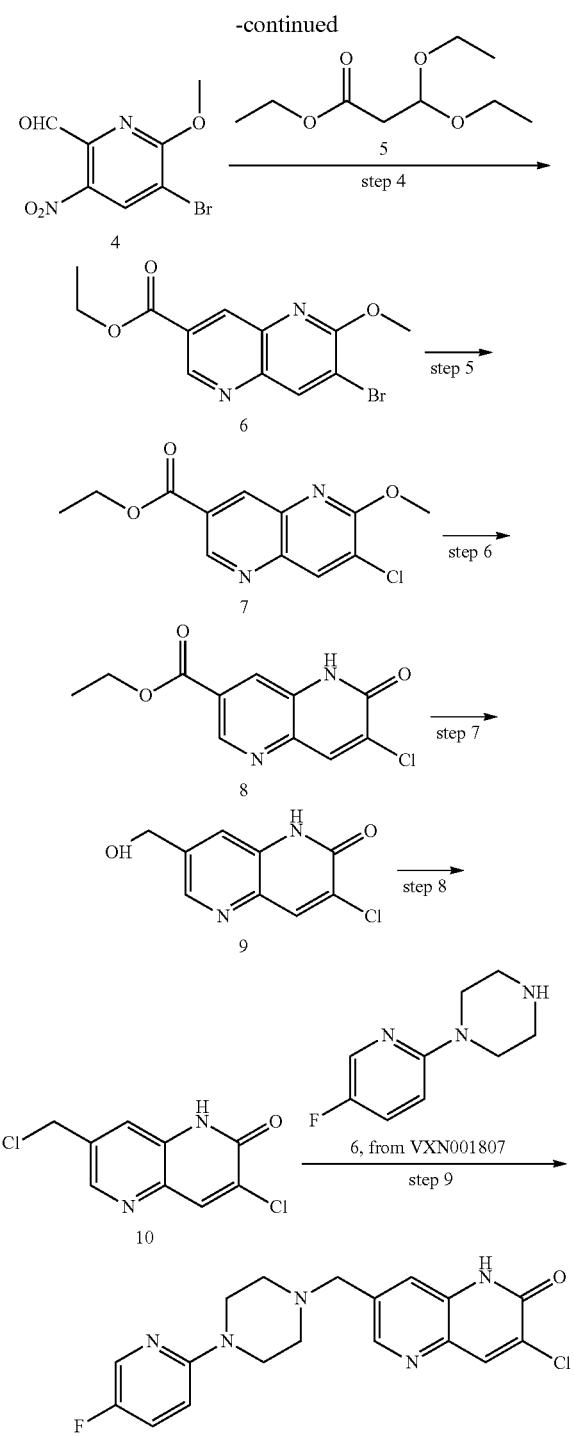

Example 47

Step 1: Preparation of 3-bromo-2-methoxy-6-methyl-5-nitropyridine

To a stirred mixture of 3-bromo-2-chloro-6-methyl-5-nitropyridine (20.00 g, 79.54 mmol, 1.00 equiv) in MeOH (50 mL) was added NaOMe (15.76 g, 87.49 mmol, 1.10 equiv, 30% wt) dropwise at 0° C. under nitrogen atmosphere. The resulting mixture was stirred overnight at rt under nitrogen atmosphere. The reaction was monitored by TLC (Pet. Ether:EtOAc=1:1, $R_f$=0.4). Upon completion, the reaction was concentrated under reduced pressure and water (100 mL) was added. The resulting mixture was extracted with EtOAc (3×100 mL). The combined organic layers were washed with brine (1×200 mL), dried over anhydrous $Na_2SO_4$, filtered and concentrated to afford 3-bromo-2-methoxy-6-methyl-5-nitropyridine (20 g, 99%). $^1$H NMR (400 MHz, DMSO-$d_6$) δ 8.66 (s, 1H), 4.04 (s, 3H), 2.70 (s, 3H).

Step 2: Preparation of (E)-2-(5-bromo-6-methoxy-3-nitropyridin-2-yl)-N,N-dimethylethen-1-amine A mixture of 3-bromo-2-methoxy-6-methyl-5-nitropyridine (15.00 g, 60.72 mmol, 1.00 equiv) in DMF-DMA (100 mL) and DMF (100 mL) was stirred overnight at 100° C. under nitrogen atmosphere. The reaction was monitored by TLC (Pet. Ether:EtOAc=1:1, $R_f$=0.5). The mixture was allowed to cool down to rt and then concentrated under reduced pressure to afford crude (E)-2-(5-bromo-6-methoxy-3-nitropyridin-2-yl)-N,N-dimethylethen-1-amine. The crude product was used in the next step directly without further purification.

Step 3: Preparation of 5-bromo-6-methoxy-3-nitropicolinaldehyde

To a stirred mixture of (E)-2-(5-bromo-6-methoxy-3-nitropyridin-2-yl)ethenyl]dimethylamine (18.01 g, crude) in THF (100 mL) and $H_2O$ (100 mL) was added $NaIO_4$ (28.00 g, 131.07 mmol, 2.20 equiv) in portions at 0° C. under nitrogen atmosphere. The resulting mixture was stirred for 2 h at rt under nitrogen atmosphere. The reaction was monitored by TLC (Pet. Ether:EtOAc=5:1, $R_f$=0.2). The reaction was quenched by the addition of sat. sodium hyposulfite (aq.) (100 mL) at rt. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The crude product was used in the next step directly without further purification $^1$H NMR (400 MHz, DMSO-$d_6$) δ 10.16 (s, 1H), 8.87 (s, 1H), 4.10 (s, 3H).

Step 4: Preparation of ethyl 7-bromo-6-methoxy-1,5-naphthyridine-3-carboxylate To a stirred mixture of 5-bromo-6-methoxy-3-nitropyridine-2-carbaldehyde (7.00 g, crude) and ethyl 3,3-diethoxypropanoate (20.40 g, 107.27 mmol, 4.00 equiv) in EtOH (100 mL) were added $SnCl_2$ (26.25 g, 134.09 mmol, 5.00 equiv) in portions at rt under nitrogen atmosphere. The resulting mixture was stirred overnight at 90° C. under nitrogen atmosphere. The reaction was monitored by LCMS. The mixture was allowed to cool down to rt. The resulting mixture was concentrated under reduced pressure. The crude mixture was poured into saturated sodium bicarbonate (100 mL). The resulting mixture was extracted with EtOAc (3×100 mL). The combined organic layers were concentrated under reduced pressure and the residue was purified by silica gel column chromatography to afford the crude product. The crude product was further purified by trituration with hexane (50 mL) to afford ethyl 7-bromo-6-methoxy-1,5-naphthyridine-3-carboxylate (3.50 g, 18.5%, over three steps). LC-MS: (ES+H, m/z): [M+H]$^+$=311.0

Step 5: Preparation of ethyl 7-chloro-6-methoxy-1,5-naphthyridine-3-carboxylate To a stirred mixture of ethyl 7-bromo-6-methoxy-1,5-naphthyridine-3-carboxylate (1.20 g, 3.85 mmol, 1.00 equiv) in DMF (10 mL) was added CuCl (0.57 g, 5.78 mmol, 1.50 equiv) at rt under nitrogen atmosphere. The resulting mixture was stirred overnight at 120° C. The reaction was monitored by LCMS. The mixture was allowed to cool down to rt. The resulting mixture was diluted with EtOAc (20 mL). The resulting mixture was washed with 3×30 mL of Water (10% $NH_3 \cdot H_2O$). The resulting mixture was concentrated under reduced pressure. The residue was purified by silica gel column chromatography to afford ethyl 7-chloro-6-methoxy-1,5-naphthyridine-3-carboxylate (800 mg, 77.78%). LC-MS: (ES+H, m/z): $[M+H]^+=267.0$; $^1$H NMR (300 MHz, DMSO-$d_6$) δ 9.27 (d, 1H), 8.63 (d, 1H), 8.57 (s, 1H), 4.41 (q, 2H), 4.12 (s, 3H), 1.37 (t, 3H).

Step 6: Preparation of ethyl 7-chloro-6-oxo-5H-1,5-naphthyridine-3-carboxylate

To a stirred mixture of ethyl 7-chloro-6-methoxy-1,5-naphthyridine-3-carboxylate (800 mg, 3.00 mmol, 1.00 equiv) in $CH_3CN$ (8 mL) was added TMSI (1.80 g, 9.00 mmol, 3.00 equiv) at rt under nitrogen atmosphere. The resulting mixture was stirred for 2 h at 50° C. The reaction was monitored by LCMS. The mixture was allowed to cool down to rt. The resulting mixture was diluted with EtOAc (50 mL). The aqueous layer was washed with 3×50 mL of water (10% $Et_3N$). The combined organic layers were washed with brine (50 mL), dried over anhydrous $Na_2SO_4$, filtered and concentrated. The residue was purified by silica gel column chromatography to afford ethyl 7-chloro-6-oxo-5H-1,5-naphthyridine-3-carboxylate (740 mg, 97.64%). LC-MS: (ES+H, m/z): $[M+H]^+=252.9$; $^1$H NMR (300 MHz, DMSO-$d_6$) δ 12.61 (s, 1H), 8.94 (d, 1H), 8.37 (d, 1H), 8.20 (s, 1H), 4.39 (q, 2H), 1.36 (t, 3H).

Step 7: Preparation of 3-chloro-7-(hydroxymethyl)-1H-1,5-naphthyridin-2-one

To a stirred mixture of ethyl 7-chloro-6-oxo-5H-1,5-naphthyridine-3-carboxylate (740 mg, 2.92 mmol, 1.00 equiv) in THF (6 mL) was added $LiAlH_4$ (2.5 mL, 5.85 mmol, 2.00 equiv) dropwise at 0° C. under nitrogen atmosphere. The resulting mixture was stirred for additional 2 h at 0° C. The reaction was monitored by LCMS. The mixture was acidified to pH 5 with 1 M HCl(aq.). The resulting mixture was concentrated under reduced pressure and the residue was purified by silica gel column chromatography to afford 3-chloro-7-(hydroxymethyl)-1H-1,5-naphthyridin-2-one (250 mg, 40.53%). LC-MS: (ES+H, m/z): $[M+H]^+=211.0$; $^1$H NMR (400 MHz, DMSO-d6) δ12.49 (s, 1H), 8.45 (d, 1H), 8.28 (s, 1H), 7.69 (d, 1H), 5.53 (t, 1H), 4.64 (d, 2H).

Step 4: Preparation of 3-chloro-7-(chloromethyl)-1H-1,5-naphthyridin-2-one

To a stirred mixture of 3-chloro-7-(hydroxymethyl)-1H-1,5-naphthyridin-2-one (250 mg, 1.18 mmol, 1.00 equiv) in $CH_2Cl_2$ (5 mL) was added $SOCl_2$ (423 mg, 3.56 mmol, 3.00 equiv) and DMF (8 mg, 0.11 mmol, 0.10 equiv) dropwise at rt under nitrogen atmosphere. The resulting mixture was stirred for 3 h at rt. The reaction was monitored by LCMS. The resulting mixture was concentrated under reduced pressure. This resulted in 3-chloro-7-(chloromethyl)-1H-1,5-naphthyridin-2-one (280 mg, crude). The crude product was used in the next step directly without further purification. LC-MS: (ES+H, m/z): $[M+H]^+=228.95$.

Step 9: Preparation of 3-chloro-7-{[4-(5-fluoropyridin-2-yl)piperazin-1-yl]methyl}-1H-1,5-naphthyridin-2-one To a stirred mixture of 3-chloro-7-(chloromethyl)-1H-1,5-naphthyridin-2-one (200 mg, 0.87 mmol, 1.00 equiv) and 1-(5-fluoropyridin-2-yl)piperazine (126 mg, 0.69 mmol, 0.80 equiv) in $CH_3CN$ (5 mL) were added DIEA (564 mg, 4.36 mmol, 5 equiv) and KI (14 mg, 0.08 mmol, 0.10 equiv) at r. The resulting mixture was stirred for 2 h at 50° C. The reaction was monitored by LCMS. The resulting mixture was cooled down to rt and poured into 20 mL of water. The resulting mixture was extracted with EtOAc (3×20 mL). The combined organic layers were washed with brine (50 mL), dried over anhydrous $Na_2SO_4$. After filtration, the filtrate was concentrated under reduced pressure. The crude product was purified by prep HPLC to afford 3-chloro-7-{[4-(5-fluoropyridin-2-yl)piperazin-1-yl]methyl}-1H-1,5-naphthyridin-2-one (42.7 mg, 13.08%). LC-MS: (ES+H, m/z): $[M+H]^+=374.0$; $^1$H NMR (300 MHz, DMSO-$d_6$) δ 12.48 (s, 1H), 8.48 (d, 1H), 8.29 (s, 1H), 8.09 (d, 1H), 7.70 (d, 1H), 7.55-7.47 (m, 1H), 6.87 (dd, 1H), 3.66 (s, 2H), 3.46-3.42 ((m, 4H), 2.53-2.50 (m, 4H); $^{19}$F NMR (282 MHz, DMSO-$d_6$) δ−143.39.

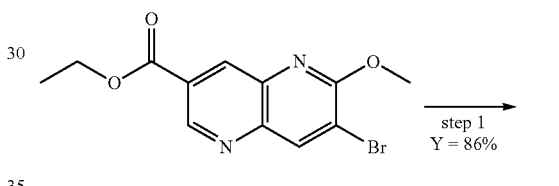

step 1
Y = 86%

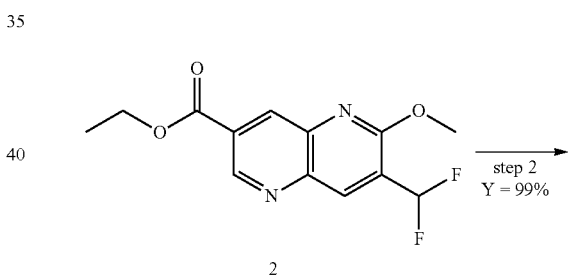

2 step 2
Y = 99%

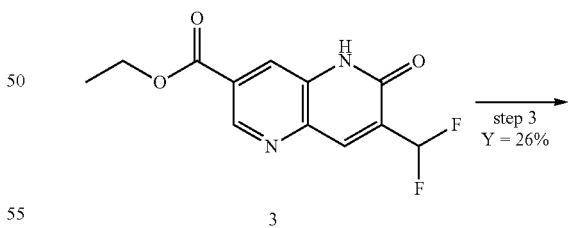

3 step 3
Y = 26%

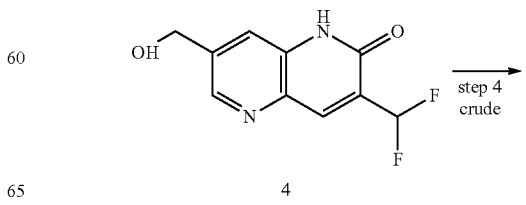

4 step 4
crude

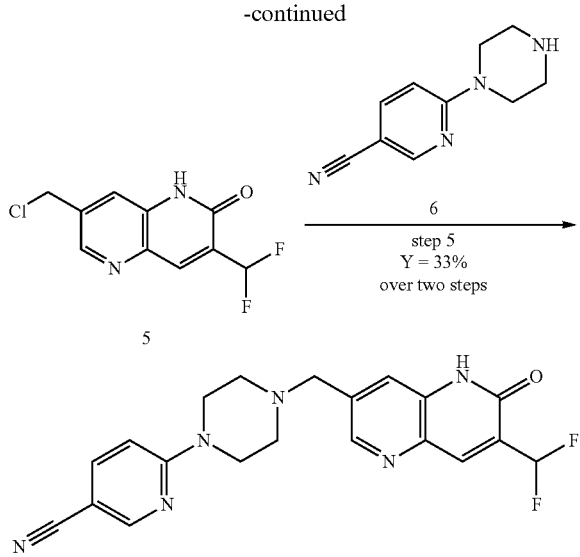

Example 48

Example 48

Step 1: Preparation of ethyl 7-(difluoromethyl)-6-methoxy-1,5-naphthyridine-3-carboxylate A solution of ethyl 7-bromo-6-methoxy-1,5-naphthyridine-3-carboxylate (300 mg, 0.96 mmol, 1.00 equiv), [1,3-Bis[2,6-bis(i-propyl)phenyl]-2-imidazolidinylidene]difluoromethylsilver(I) (97 mg, 0.17 mmol, 1.10 equiv), [2-[2-(diphenylphosphanyl)phenoxy]phenyl]diphenylphosphane (181 mg, 0.33 mmol, 0.35 equiv) and Pd(dba)2 (177 mg, 0.30 mmol, 0.32 equiv) in toluene (5 ml) was stirred for 1.5 h at 80° C. under nitrogen atmosphere. The reaction was monitored by LCMS. The mixture was allowed to cool down to rt. The resulting mixture was diluted with EtOAc (50 mL). The resulting mixture was filtered and the filter cake was washed with EtOAc (3×50 mL). The filtrate was concentrated under reduced pressure. The residue was purified by Prep-TLC (Pet. Ether/EtOAc 5:1) to afford ethyl 7-(difluoromethyl)-6-methoxy-1,5-naphthyridine-3-carboxylate (235 mg, 86%). LC-MS: (ES+H, m/z): [M+H]$^+$=283.1; $^1$H NMR (300 MHz, DMSO-d$_6$) δ 9.25 (d, 1H), 8.59 (d, 1H), 8.53 (s, 1H), 7.24 (t, 1H), 4.42 (q, 2H), 4.12 (s, 3H), 1.40 (t, 3H); $^{19}$F NMR (282 MHz, DMSO-d$_6$) δ−117.83.

Step 2: Preparation of ethyl 7-(difluoromethyl)-6-oxo-5H-1,5-naphthyridine-3-carboxylate A solution of ethyl 7-(difluoromethyl)-6-methoxy-1,5-naphthyridine-3-carboxylate (240 mg, 0.85 mmol, 1.00 equiv) in ACN (7 mL) was added TMSI (680 mg, 3.40 mmol, 4.00 equiv) dropwise at rt. The reaction mixture was then stirred for 5 h at 50° C. under nitrogen atmosphere, cooled to rt and concentrated under reduced pressure. The residue was purified by silica gel column chromatography, (Pet. Ether/EtOAc) to afford ethyl 7-(difluoromethyl)-6-oxo-5H-1,5-naphthyridine-3-carboxylate (225 mg, 99%). LC-MS: (ES+H, m/z): [M+H]$^+$=269.1.

Step 3: Preparation of 3-(difluoromethyl)-7-(hydroxymethyl)-1H-1,5-naphthyridin-2-one To a stirred solution of ethyl 7-(difluoromethyl)-6-oxo-5H-1,5-naphthyridine-3-carboxylate (230 mg, 0.85 mmol, 1.00 equiv) in THF (5 ml) was added LiAlH$_4$ (0.69 mL, 2.5 mol/L in THF, 2.00 equiv) dropwise at 0° C. under nitrogen atmosphere. The resulting mixture was stirred for 1 h at rt. The reaction was monitored by LCMS. The resulting mixture was quenched with MeOH (10 mL) and then DCM (50 mL) was added. The solution was filtered, the filter cake was washed with DCM/MeOH (5:1) (3×50 mL). The filtrate was concentrated under reduced pressure. The residue was purified by silica gel column (CH$_2$Cl$_2$/MeOH) to afford 3-(difluoromethyl)-7-(hydroxymethyl)-1H-1,5-naphthyridin-2-one (50 mg, 26%). LC-MS: (ES+H, m/z): [M+H]$^+$=227.0; $^1$H NMR (400 MHz, DMSO-d$_6$) δ 12.36 (s, 1H), 8.50 (d, 1H), 8.16 (d, 1H), 7.70 (s, 1H), 6.98 (t, 1H), 5.57 (t, 1H), 4.67 (d, 2H).

Step 4: Preparation of 7-(chloromethyl)-3-(difluoromethyl)-1H-1,5-naphthyridin-2-one To a stirred solution of 3-(difluoromethyl)-7-(hydroxymethyl)-1H-1,5-naphthyridin-2-one (80 mg, 0.35 mmol, 1.00 equiv) and DMF (1 mg, 0.02 mmol, 0.05 equiv) in DCM (4 ml) was added SOCl$_2$ (126 mg, 1.06 mmol, 3.00 equiv) dropwise at rt under nitrogen atmosphere. The resulting mixture was stirred for 5 h at rt. The reaction was monitored by LCMS. The resulting mixture was concentrated under reduced pressure. The crude product was used in the next step directly without further purification. LC-MS: (ES+H, m/z): [M+H]$^+$=245.0.

Step 5: Preparation of 6-(4-{[7-(difluoromethyl)-6-oxo-5H-1,5-naphthyridin-3-yl]methyl}piperazin-1-yl)pyridine-3-carbonitrile To a stirred solution of 7-(chloromethyl)-3-(difluoromethyl)-1H-1,5-naphthyridin-2-one (86 mg, assumed 100% yield, 0.35 mmol, 1.00 equiv), 6-(piperazin-1-yl)pyridine-3-carbonitrile (66 mg, 0.35 mmol, 1.00 equiv), KI (11 mg, 0.07 mmol, 0.20 equiv) in ACN (5 ml) was added DIEA (227 mg, 1.76 mmol, 5.00 equiv) dropwise at rt. The resulting mixture was stirred for 1 h at 80° C. The reaction was monitored by LCMS. The mixture was allowed to cool down to rt. The resulting mixture was diluted with water (50 mL). The solution was extracted with EtOAc (3×100 mL). The combined organic layers were concentrated under reduced pressure. The residue was purified by silica gel column chromatography to afford the crude product (80 mg). The crude product was purified by prep HPLC to afford 6-(4-{[7-(difluoromethyl)-6-oxo-5H-1,5-naphthyridin-3-yl]methyl}piperazin-1-yl)pyridine-3-carbonitrile (42.9 mg, 33% over two steps). LC-MS: (ES+H, m/z): [M+H]$^+$=397.1; $^1$H NMR (300 MHz, DMSO-d$_6$) δ 12.33 (s, 1H), 8.54 (d, 1H), 8.48 (d, 1H), 8.16 (s, 1H), 7.85 (dd, 1H), 7.71 (d, 1H), 7.20-6.73 (m, 2H), 3.72-3.68 (M, 4H), 3.67 (s, 2H), 2.51-2.49 (m, 4H); $^{19}$F NMR (282 MHz, DMSO-d$_6$) δ−119.30.

Example 49

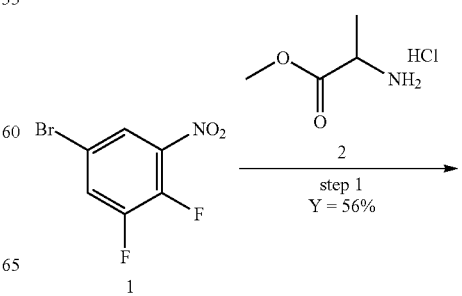

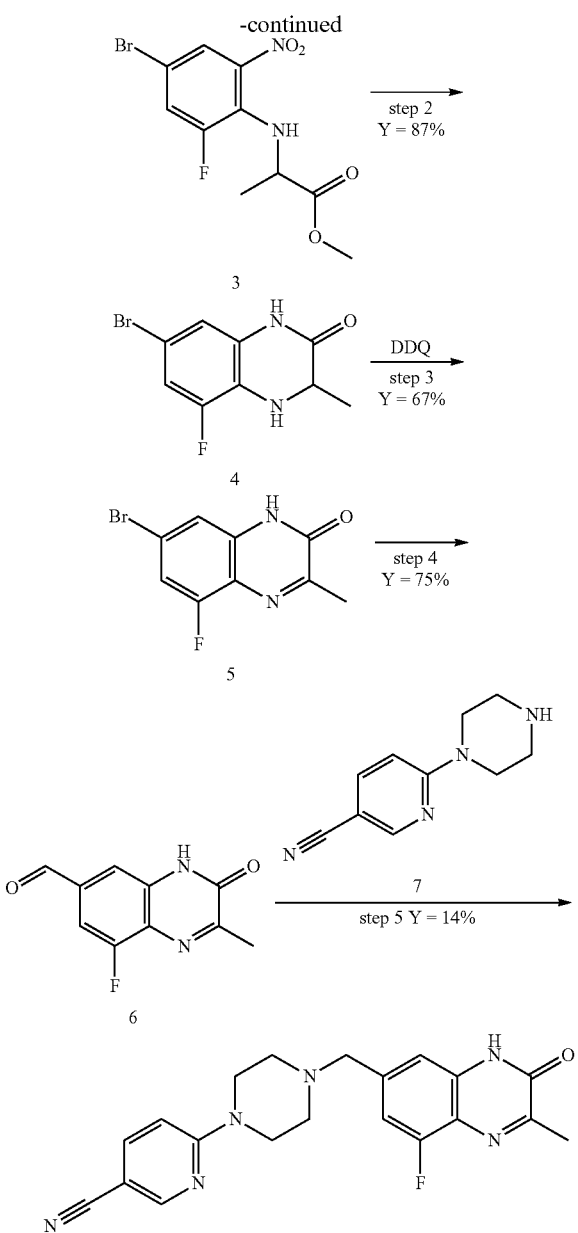

Example 49

Step 1: Preparation of methyl 2-[(4-bromo-2-fluoro-6-nitrophenyl)amino] propanoate To a stirred mixture of 5-bromo-1,2-difluoro-3-nitrobenzene (10.00 g, 42.01 mmol, 1.00 equiv) and methyl 2-aminopropanoate hydrochloride (2.93 g, 21.00 mmol, 1.00 equiv) in NMP (200 mL) was added DIEA (27.15 g, 210.09 mmol, 5.00 equiv) dropwise at rt under nitrogen atmosphere. The resulting mixture was stirred for 2 h at 100° C. under nitrogen atmosphere. The reaction was monitored by TLC (Pet. Ether/EtOAc=10/1). The mixture was allowed to cool down to rt. The resulting mixture was diluted with EtOAc (1L). The resulting mixture was washed with water (3×300 mL), dried over anhydrous $Na_2SO_4$. After filtration, the filtrate was concentrated under reduced pressure. The residue was purified by silica gel column chromatography to afford methyl 2-[(4-bromo-2-fluoro-6-nitrophenyl)amino] propanoate (7.5 g, 56%) as a red oil. $^1H$ NMR (400 MHZ, DMSO-$d_6$) δ 8.08 (t, 1H), 7.87 (dd, 1H), 7.77 (dd, 1H), 4.67-4.55 (m, 1H), 3.68 (s, 3H), 1.48 (dd, 3H); $^{19}F$ NMR (377 MHz, DMSO-$d_6$) δ-122.19.

Step 2: Preparation of 7-bromo-5-fluoro-3-methyl-3,4-dihydro-1H-quinoxalin-2-one To a stirred solution of methyl 2-[(4-bromo-2-fluoro-6-nitrophenyl)amino] propanoate (6.00 g, 18.68 mmol, 1.00 equiv) in HOAc (200 mL) was added Fe (5.22 g, 93.43 mmol, 5.00 equiv) at rt under nitrogen atmosphere. The resulting mixture was stirred for 2 h at 80° C. under nitrogen atmosphere. The reaction was monitored by LCMS. The mixture was allowed to cool down to rt. The resulting mixture was diluted with EtOAc (50 mL). The resulting mixture was filtered, the filter cake was washed with DCM:MeOH=4:1 (3×100 mL). The filtrate was concentrated under reduced pressure. The pH of the residue was adjusted to pH 7 with sat. $NaHCO_3$(aq.). The resulting mixture was then extracted with $CH_2Cl_2$ (3×300 mL). The combined organic layers were washed with brine (1×100 mL) and dried over anhydrous $Na_2SO_4$. After filtration, the filtrate was concentrated under reduced pressure to afford 7-bromo-5-fluoro-3-methyl-3,4-dihydro-1H-quinoxalin-2-one (4.2 g, 87%). LC-MS: (ES-H, m/z): [M−H]$^−$=257.1; 1H NMR (400 MHz, DMSO-$d_6$) δ 10.54 (s, 1H), 7.01 (dd, 1H), 6.76 (t, 1H), 6.20 (s, 1H), 3.90-3.80 (m, 1H), 1.28 (d, 3H). $^{19}F$ NMR (377 MHz, DMSO-$d_6$) δ-132.99.

Step 3: Preparation of 7-bromo-5-fluoro-3-methyl-1H-quinoxalin-2-one

To a stirred solution of 7-bromo-5-fluoro-3-methyl-3,4-dihydro-1H-quinoxalin-2-one (4.50 g, 17.36 mmol, 1.00 equiv) in DCM (500 mL) was added DDQ (4.34 g, 19.10 mmol, 1.10 equiv) at t. The resulting mixture was stirred for 2 h at rt under nitrogen atmosphere. The reaction was monitored by LCMS. The resulting mixture was concentrated under reduced pressure. The resulting mixture was diluted with sat. $NaHCO_3$(aq) (500 mL). The resulting mixture was stirred for 30 min at rt. The resulting mixture was filtered, the filter cake was washed with sat. $NaHCO_3$ (aq) (3×100 mL). The filter cake was dried under reduced pressure. The residue was purified by silica gel column chromatography to afford 7-bromo-5-fluoro-3-methyl-1H-quinoxalin-2-one (3 g, 67%). LC-MS: (ES-H, m/z): [M−H]$^−$=255.0; $^1H$ NMR (400 MHz, DMSO-$d_6$) δ 12.52 (s, 1H), 7.49-7.40 (m, 1H), 7.24 (q, 1H), 2.40 (q, 3H).

Step 4: Preparation of 8-fluoro-2-methyl-3-oxo-4H-quinoxaline-6-carbaldehyde

To a solution of 7-bromo-5-fluoro-3-methyl-1H-quinoxalin-2-one (500 mg, 1.94 mmol, 1.00 equiv) in Toluene (100 mL) was added bis(adamantan-1-yl)(butyl)phosphane (349 mg, 0.97 mmol, 0.50 equiv), TMEDA (1.13 g, 9.72 mmol, 5.00 equiv) and Pd(OAc)2 (218 mg, 0.97 mmol, 0.50 equiv) in a pressure tank. The mixture was purged with nitrogen for 5 min and then was pressurized to 30 Mpa with CO2:H2=1:1 at rt. The resulting mixture was stirred overnight at 100° C. The reaction mixture was cooled to rt and filtered to remove insoluble solids. The reaction was monitored by LCMS. The resulting mixture was concentrated under reduced pressure. The residue was purified by silica gel column chromatography to afford 8-fluoro-2-methyl-3-oxo-4H-quinoxaline-6-carbaldehyde (300 mg, 74.8%). LC-MS: (ES-H, m/z):

[M-H]—=205.2; $^1$H NMR (400 MHz, DMSO-d$_6$) δ 12.75 (s, 1H), 10.02 (q, 1H), 7.67-7.52 (m, 2H), 2.49-2.44 (m, 3H).

Step 5: Preparation of 6-{4-[(8-fluoro-2-methyl-3-oxo-4H-quinoxalin-6-yl)methyl]piperazin-1-yl}pyridine-3-carbonitrile To a stirred mixture of 8-fluoro-2-methyl-3-oxo-4H-quinoxaline-6-carbaldehyde (200 mg, 0.97 mmol, 1.00 equiv) and 6-(piperazin-1-yl)pyridine-3-carbonitrile (274 mg, 1.45 mmol, 1.50 equiv) in THF (20 mL) was added tetrakis (propan-2-yloxy)titanium (551 mg, 1.94 mmol, 2.00 equiv) at rt under nitrogen atmosphere. The resulting mixture was stirred for 4 h at rt under nitrogen atmosphere. To the above mixture was added NaBH(OAc)$_3$ (822 mg, 3.88 mmol, 4.00 equiv) at rt. The resulting mixture was stirred for additional 4h at rt. The reaction was monitored by LCMS. The reaction was quenched by the addition of Water (80 mL) at 0° C. The resulting mixture was extracted with EtOAc (3×100 mL). The combined organic layers were washed with brine (1×50 mL), dried over anhydrous Na$_2$SO$_4$. After filtration, the filtrate was concentrated under reduced pressure. The residue was purified by silica gel column chromatography followed by trituration with MeCN (5 mL) to afford 6-{4-[(8-fluoro-2-methyl-3-oxo-4H-quinoxalin-6-yl)methyl]piperazin-1-yl}pyridine-3-carbonitrile (51.1 mg, 14%). LC-MS: (ES+H, m/z): [M+H]$^+$=379.2; $^1$H NMR (400 MHz, DMSO-d$_6$) δ 12.44 (s, 1H), 8.48 (d, 1H), 7.85 (dd, 1H), 7.09 (d, 2H), 6.93 (d, 1H), 3.68 (t 4H), 3.60-3.55 (m, 2H), 2.47 (d, 4H), 2.41 (s, 3H); $^{19}$F NMR (377 MHz, DMSO-d$_6$) δ–125.51.

Example 60

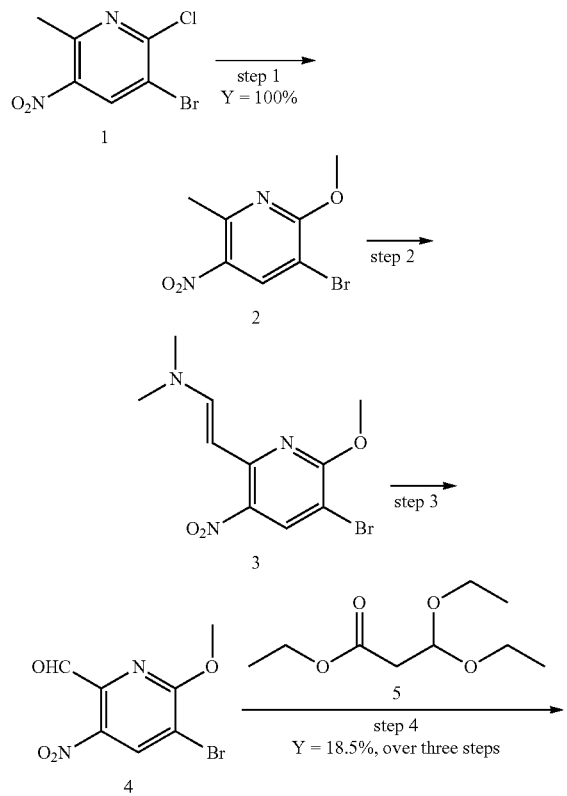

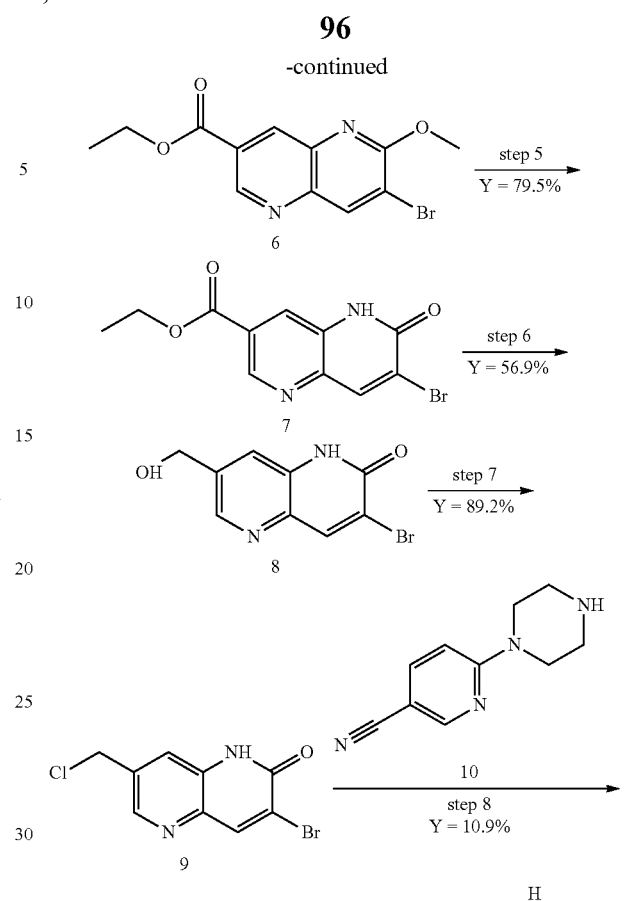

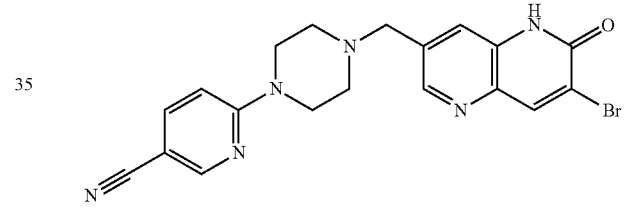

Example 60

Step 1: Preparation of 3-bromo-2-methoxy-6-methyl-5-nitropyridine

To a stirred mixture of 3-bromo-2-chloro-6-methyl-5-nitropyridine (20.00 g, 79.54 mmol, 1.00 equiv.) in MeOH (50 mL) was added NaOMe (15.76 g, 87.49 mmol, 1.10 equiv., 30% wt.) dropwise at 0° C. under nitrogen atmosphere. The resulting mixture was stirred overnight at room temperature under nitrogen atmosphere. The reaction was monitored by TLC (PE:EA=1:1, R$_f$=0.4). The resulting mixture was concentrated under reduced pressure and water (100 mL) was added. The resulting mixture was extracted with EtOAc (3×100 mL). The combined organic layers were washed with brine (1×200 mL), dried over anhydrous Na$_2$SO$_4$. After filtration, the filtrate was concentrated under reduced pressure to afford 3-bromo-2-methoxy-6-methyl-5-nitropyridine (20 g, 99%). $^1$H NMR (400 MHz, DMSO-d$_6$) δ 8.66 (s, 1H), 4.04 (s, 3H), 2.70 (s, 3H).

Step 2: Preparation of (E)-2-(5-bromo-6-methoxy-3-nitropyridin-2-yl)-N,N-dimethylethen-1-amine A mixture of 3-bromo-2-methoxy-6-methyl-5-nitropyridine (15.00 g, 60.72 mmol, 1.00 equiv.) in DMF-DMA (100 mL) and DMF (100 mL) was stirred overnight at 100° C. under nitrogen atmosphere. The reaction was monitored by TLC (PE:EA=1:1, $R_f$=0.5). The mixture was allowed to cool down to room temperature. The resulting mixture was concentrated under reduced pressure. The crude product was used in the next step directly without further purification.

Step 3: Preparation of 5-bromo-6-methoxy-3-nitropicolinaldehyde

To a stirred mixture of (E)-2-(5-bromo-6-methoxy-3-nitropyridin-2-yl)ethenyl]dimethylamine (18.01 g, crude) in THF (100 mL) and $H_2O$ (100 mL) was added $NaIO_4$ (28.00 g, 131.07 mmol, 2.20 equiv.) in portions at 0° C. under nitrogen atmosphere. The resulting mixture was stirred for 2 h at room temperature under nitrogen atmosphere. The reaction was monitored by TLC (PE:EA=5:1, $R_f$=0.2). The reaction was quenched by the addition of sat. sodium hyposulfite (aq.) (100 mL) at room temperature. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The crude product was used in the next step directly without further purification. $^1$H NMR (400 MHz, DMSO-$d_6$) δ 10.16 (s, 1H), 8.87 (s, 1H), 4.10 (s, 3H).

Step 4: Preparation of ethyl 7-bromo-6-methoxy-1,5-naphthyridine-3-carboxylate

To a stirred mixture of 5-bromo-6-methoxy-3-nitropyridine-2-carbaldehyde (7.00 g, crude) and ethyl 3,3-diethoxypropanoate (20.40 g, 107.27 mmol, 4.00 equiv.) in EtOH (100 mL) were added $SnCl_2$ (26.25 g, 134.09 mmol, 5.00 equiv.) in portions at room temperature under nitrogen atmosphere. The resulting mixture was stirred overnight at 90° C. under nitrogen atmosphere. The reaction was monitored by LCMS. The mixture was allowed to cool down to room temperature. The resulting mixture was concentrated under reduced pressure. The crude mixture was poured into saturated sodium bicarbonate (100 mL). The resulting mixture was extracted with EtOAc (3×100 mL). The combined organic layers were concentrated under reduced pressure. The residue was purified by silica gel column chromatography to afford crude product. The crude product was purified by trituration with hexane (50 mL) to afford ethyl 7-bromo-6-methoxy-1,5-naphthyridine-3-carboxylate (3.50 g, 18.5% yield over three steps). LC-MS: (ES+H, m/z): [M+H]$^+$=311.0/313.0; $^1$H NMR (400 MHz, DMSO-$d_6$) δ 9.22 (s, 1H), 8.78 (s, 1H), 8.58 (s, 1H), 4.42 (q, 2H), 4.12 (s, 3H), 1.39 (t 3H).

Step 5: Preparation of ethyl 7-bromo-6-oxo-5H-1,5-naphthyridine-3-carboxylate

A solution of ethyl 7-bromo-6-methoxy-1,5-naphthyridine-3-carboxylate (5.00 g, 16.07 mmol, 1.00 equiv.) in ACN (400 mL) were added TMSI (13.8 mL, 96.42 mmol, 6.00 equiv.) dropwise at room temperature. The final reaction mixture was stirred for 2 h at 80° C. under nitrogen atmosphere. The mixture was allowed to cool down to room temperature. The reaction was monitored by LCMS. The resulting mixture was concentrated under reduced pressure. The residue was purified by silica gel column chromatography with the following conditions: column, silica gel; mobile phase, EA in DCM, 45% to 60% gradient in 20 min; detector, UV 254 nm. The resulting mixture was concentrated under reduced pressure to afford ethyl 7-bromo-6-oxo-5H-1,5-naphthyridine-3-carboxylate (3.8 g, 79.5%). LC-MS: (ES+H, m/z): [M+H]$^+$=296.95/298.95

Step 6: Preparation of 3-bromo-7-(hydroxymethyl)-1H-1,5-naphthyridin-2-one

To a stirred mixture of ethyl 7-bromo-6-oxo-5H-1,5-naphthyridine-3-carboxylate (450 mg, 1.51 mmol, 1.00 equiv.) in THF (8 mL) was added $LiAlH_4$ (1.21 mL, 3.03 mmol, 2.00 equiv, 2.5 M in THF) dropwise at 0° C. under nitrogen atmosphere. The resulting mixture was stirred for 1 h at 0° C. under nitrogen atmosphere. The reaction was monitored by LCMS. The reaction was quenched by the addition of HCl (3.03 mL, 3.03 mmol, 2.00 equiv.) at 0° C. The resulting mixture was concentrated under reduced pressure. The residue was purified by silica gel column chromatography to afford 3-bromo-7-(hydroxymethyl)-1H-1,5-naphthyridin-2-one (220 mg, 56.9%). LC-MS: (ES+H, m/z): [M+H]$^+$=255.0/257.0.

Step 7: Preparation of 3-bromo-7-(chloromethyl)-1H-1,5-naphthyridin-2-one

To a stirred mixture of 3-bromo-7-(hydroxymethyl)-1H-1,5-naphthyridin-2-one (230 mg, 0.90 mmol, 1.00 equiv.) and DMF (6 mg, 0.09 mmol, 0.10 equiv.) in DCM (7 mL) was added $SOCl_2$ (321 mg, 2.70 mmol, 3.00 equiv.) dropwise at 0° C. under nitrogen atmosphere. The resulting mixture was stirred overnight at room temperature under nitrogen atmosphere. The reaction was monitored by LCMS. The resulting mixture was concentrated under reduced pressure to afford 3-bromo-7-(chloromethyl)-1H-1,5-naphthyridin-2-one (220 mg, 89.2%). LC-MS: (ES+H, m/z): [M+H]$^+$=272.9/274.9.

Step 8: Preparation of 6-{4-[(7-bromo-6-oxo-5H-1,5-naphthyridin-3-yl)methyl]piperazin-1-yl}pyridine-3-carbonitrile To a stirred mixture of 3-bromo-7-(chloromethyl)-1H-1,5-naphthyridin-2-one (150 mg, 0.54 mmol, 1.00 equiv.), DIEA (354 mg, 2.74 mmol, 5.00 equiv.) and 6-(piperazin-1-yl)pyridine-3-carbonitrile (113 mg, 0.60 mmol, 1.10 equiv.) in MeCN (7 mL) was added KI (18 mg, 0.11 mmol, 0.20 equiv.) in portions at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was concentrated under reduced pressure. The crude product (120 mg) was purified by Prep-HPLC, the pure fraction was concentrated then lyophilized to afford 6-{4-[(7-bromo-6-oxo-5H-1,5-naphthyridin-3-yl)methyl]piperazin-1-yl}pyridine-3-carbonitrile (25.6 mg, 10.9%). LC-MS: (ES+H, m/z): [M+H]$^+$=425.00/427.00; $^1$H NMR (400 MHz, DMSO-$d_6$) δ 12.41 (s, 1H), 8.47 (s, 3H), 7.85 (dd, J=9.1, 2.4 Hz, 1H), 7.68 (s, 1H), 6.93 (d, J=9.1 Hz, 1H), 3.78-3.59 (m, 6H), 2.48 (d, J=4.7 Hz, 4H).

Example 68 and 69

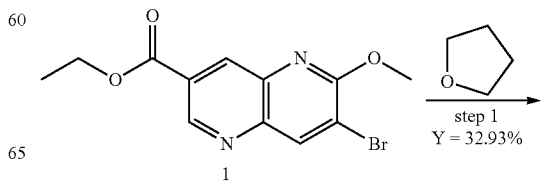

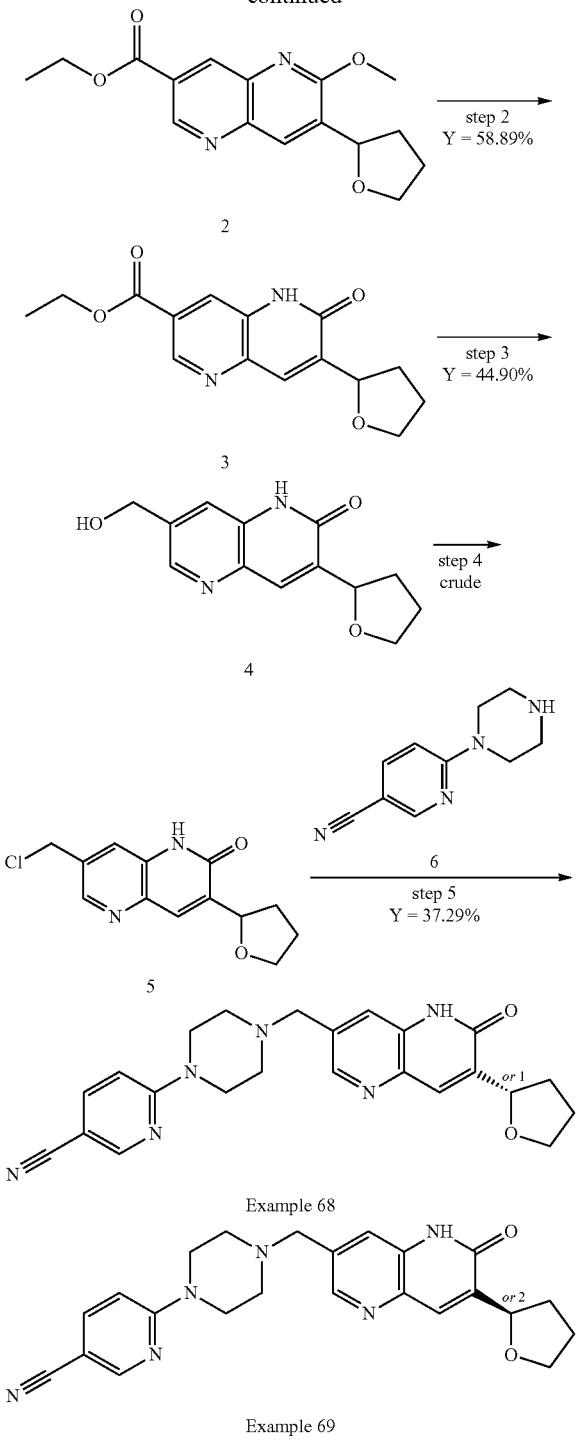

Example 68

Example 69

Step 1: Preparation of ethyl 6-methoxy-7-(oxolan-2-yl)-1,5-naphthyridine-3-carboxylate To a stirred solution of ethyl 7-bromo-6-methoxy-1,5-naphthyridine-3-carboxylate (5.00 g, 16.07 mmol, 1.00 equiv.) and (4-methoxyphenyl)[4-(trifluoromethyl)phenyl]methanone (1.12 g, 4.01 mmol, 0.25 equiv.) in THF were added 5,5'-dimethyl-2,2'-bipyridine (0.74 g, 4.01 mmol, 0.25 equiv.), nickel acetylacetonate (1.03 g, 4.01 mmol, 0.25 equiv.) and $Na_2CO_3$ (1.70 g, 16.07 mmol, 1.00 equiv.) at room temperature under nitrogen atmosphere. The resulting mixture was placed approximately ~3 cm away from two 40W Blue LED and stirred for 7 days at room temperature under nitrogen atmosphere. The reaction was monitored by LCMS. The resulting mixture was extracted with EtOAc (3×100 mL). The combined organic layers were washed with brine (50 mL), dried over anhydrous $Na_2SO_4$. After filtration, the filtrate was concentrated under reduced pressure. The residue was purified by silica gel column chromatography to afford ethyl 6-methoxy-7-(oxolan-2-yl)-1,5-naphthyridine-3-carboxylate (1.6 g, 32.93%/o). LC-MS: (ES+H, m/z): $[M+H]^+$=303.15; $^1$H NMR (400 MHz, DMSO-$d_6$) δ 9.20 (d, J=2.0 Hz, 1H), 8.57 (dd, J=2.1, 0.8 Hz, 1H), 8.27-8.10 (m, 1H), 5.13-5.04 (m, 1H), 4.41 (q, J=7.1 Hz, 2H), 4.18-4.09 (m, 1H), 4.09 (s, 3H), 3.95-3.85 (m, 1H), 2.49-2.39 (m, 1H), 2.05-1.82 (m, 2H), 1.79-1.67 (m, 1H), 1.39 (t, J=7.1 Hz, 3H).

Step 2: Preparation of ethyl 6-oxo-7-(oxolan-2-yl)-5H-1,5-naphthyridine-3-carboxylate To a stirred solution of ethyl 6-methoxy-7-(oxolan-2-yl)-1,5-naphthyridine-3-carboxylate (1.30 g, 4.30 mmol, 1.00 equiv.) in MeCN were added HBr in AcOH (0.25 ml, 33 wt. %, 2.00 equiv.) at 0° C. under nitrogen atmosphere. The resulting mixture was stirred for 0.5 h at 0° C. The reaction was monitored by LCMS. The resulting mixture was diluted with water (20 mL) and basified to pH 8 with $Et_3N$. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography to afford ethyl 6-oxo-7-(oxolan-2-yl)-5H-1,5-naphthyridine-3-carboxylate (730 mg, 58.89%). LC-MS: (ES+H, m/z): $[M+H]^+$=289.10; $^1$H NMR (400 MHz, DMSO-$d_6$) δ 12.14 (s, 1H), 8.91 (d, J=1.9 Hz, 1H), 8.18 (d, J=1.9 Hz, 1H), 7.84 (d, J=1.1 Hz, 1H), 4.96-4.87 (m, 1H), 4.39 (q, J=7.1 Hz, 2H), 4.12-4.04 (m, 1H), 3.91-3.79 (m, 1H), 2.48-2.32 (m, 1H), 1.99-1.81 (m, 2H), 1.74-1.63 (m, 1H), 1.36 (t, J=7.1 Hz, 3H).

Step 3: Preparation of 7-(hydroxymethyl)-3-(oxolan-2-yl)-1H-1,5-naphthyridin-2-one To a stirred mixture of ethyl 6-oxo-7-(oxolan-2-yl)-5H-1,5-naphthyridine-3-carboxylate (730 mg, 2.53 mmol, 1.00 equiv.) in THF (8 mL) was added $LiAlH_4$ (192 mg, 5.06 mmol, 2.00 equiv.) dropwise at 0° C. under nitrogen atmosphere. The resulting mixture was stirred for 1 h at 0° C. under nitrogen atmosphere. The reaction was monitored by LCMS. The reaction was quenched by the addition of 1M HCl (1 mL) at 0° C. The resulting mixture was concentrated under reduced pressure. The residue was purified by silica gel column chromatography to afford 7-(hydroxymethyl)-3-(oxolan-2-yl)-1H-1,5-naphthyridin-2-one (280 mg, 44.90%/o). LC-MS: (ES+H, m/z): $[M+H]^+$=247.00; $^1$H NMR (300 MHz, DMSO-$d_6$) δ 11.97 (s, 1H), 8.40 (d, J=1.9 Hz, 1H), 7.80 (s, 1H), 7.64 (d, J=1.9 Hz, 11H), 5.48 (t, J=5.6 Hz, 1H), 4.98-4.84 (m, 1H), 4.63 (d, J=5.3 Hz, 2H), 4.18-4.01 (m, 1H), 3.91-3.75 (m, 1H), 2.45-2.31 (m, 1H), 2.02-1.78 (M, 2H), 1.74-1.58 (m, 1H).

Step 4: Preparation of 7-(chloromethyl)-3-(oxolan-2-yl)-1H-1,5-naphthyridin-2-one To a stirred solution of 7-(hydroxymethyl)-3-(oxolan-2-yl)-1H-1,5-naphthyridin-2-one (280 mg, 1.13 mmol, 1.00 equiv.) and DMF (8 mg, 0.11 mmol, 0.10 equiv.) in DCM were added SOCl$_2$ (0.25 mL, 3.41 mmol, 3.00 equiv.) dropwise at 0° C. under nitrogen atmosphere. The resulting mixture was stirred for 5 h at room temperature under nitrogen atmosphere. The reaction was monitored by LCMS. The resulting mixture was concentrated under reduced pressure, to afford 7-(chloromethyl)-3-(oxolan-2-yl)-1H-1,5-naphthyridin-2-one (300 mg, crude). LC-MS: (ES+H, m/z): [M+H]$^+$=265.05.

Step 5: Preparation of 6-(4-{[6-oxo-7-(oxolan-2-yl)-5H-1,5-naphthyridin-3-yl]methyl}piperazin-1-yl)pyridine-3-carbonitrile To a stirred mixture of 7-(chloromethyl)-3-(oxolan-2-yl)-1H-1,5-naphthyridin-2-one (150 mg, 0.56 mmol, 1.00 equiv.) and 6-(piperazin-1-yl)pyridine-3-carbonitrile (106 mg, 0.56 mmol, 1.00 equiv.) in MeCN (10 mL) were added DIEA (292 mg, 2.26 mmol, 4.00 equiv.) and KI (18 mg, 0.11 mmol, 0.20 equiv.) at room temperature under nitrogen atmosphere. The resulting mixture was stirred for 2 h at 80° C. under nitrogen atmosphere. The mixture was allowed to cool down to room temperature. The reaction was monitored by LCMS. The resulting mixture was extracted with EtOAc (3×20 mL). The combined organic layers were washed with brine (20 mL) and dried over anhydrous Na$_2$SO$_4$. After filtration, the filtrate was concentrated under reduced pressure. The residue was purified by reverse flash chromatography to afford 6-(4-{[6-oxo-7-(oxolan-2-yl)-5H-1,5-naphthyridin-3-yl]methyl}piperazin-1-yl)pyridine-3-carbonitrile (88 mg, 37.29%). LC-MS: (ES+H, m/z): [M+H]$^+$=417.10. The racemate (88 mg) was separated by prep-chiral-HPLC with the following conditions: Column: CHIRALPAK IH, 2*25 cm, 5 jam; Mobile Phase A: Hex(10 mM NH$_3$-MeOH), Mobile Phase B: EtOH:ACN=5:1; Flow rate: 20 mL/min; Gradient: 50% B to 50% B in 12 min; Wave Length: 218/282 nm; RT1(min): 4.62; RT2(min): 6.76; Sample Solvent: MeOH:DCM=1:1—HPLC; Injection Volume: 0.75 mL; Number Of Runs: 6, the pure fraction was concentrated under vacuum then lyophilized to afford Example 68 (34.2 mg, 99.7% purity, ee=100%) and Example 69 (34.1 mg, 99.3% purity, ee=99.7%). Example 68: LC-MS: (ES+H, m/z): [M+H]$^+$=417.10; $^1$H NMR (300 MHz, DMSO-d$_6$) δ 11.95 (s, 1H), 8.47 (d, J=2.4 Hz, 1H), 8.43 (d, J=1.8 Hz, 1H), 7.84 (dd, J=9.1, 2.4 Hz, 1H), 7.80 (d, J=1.3 Hz, 1H), 7.64 (d, J=1.9 Hz, 1H), 6.93 (d, J=9.2 Hz, 1H), 4.89 (t, J=6.8 Hz, 1H), 4.10-4.03 (m, 1H), 3.87-3.79 (m, 1H), 3.73-3.62 (m, 6H), 2.58-2.49 (m, 4H), 2.43-2.30 (m, 1H), 2.02-1.77 (m, 2H), 1.73-1.57 (m, 1H). Example 69: LC-MS: (ES+H, m/z): [M+H]$^+$=417.10; $^1$H NMR (300 MHz, DMSO-d$_6$) δ 11.95 (s, 1H), 8.48 (d, J=2.4 Hz, 1H), 8.43 (d, J=1.8 Hz, 1H), 7.85 (dd, J=9.1, 2.4 Hz, 1H), 7.82-7.77 (m, 1H), 7.64 (d, J=1.9 Hz, 1H), 6.93 (d, J=9.1 Hz, 1H), 4.90 (t, J=6.8 Hz, 1H), 4.15-4.00 (m, 1H), 3.92-3.76 (m, 1H), 3.74-3.59 (m, 6H), 2.50-2.45 (m, 4H), 2.44-2.31 (m, 1H), 2.02-1.78 (m, 2H), 1.74-1.57 (m, 1H).

Example 71

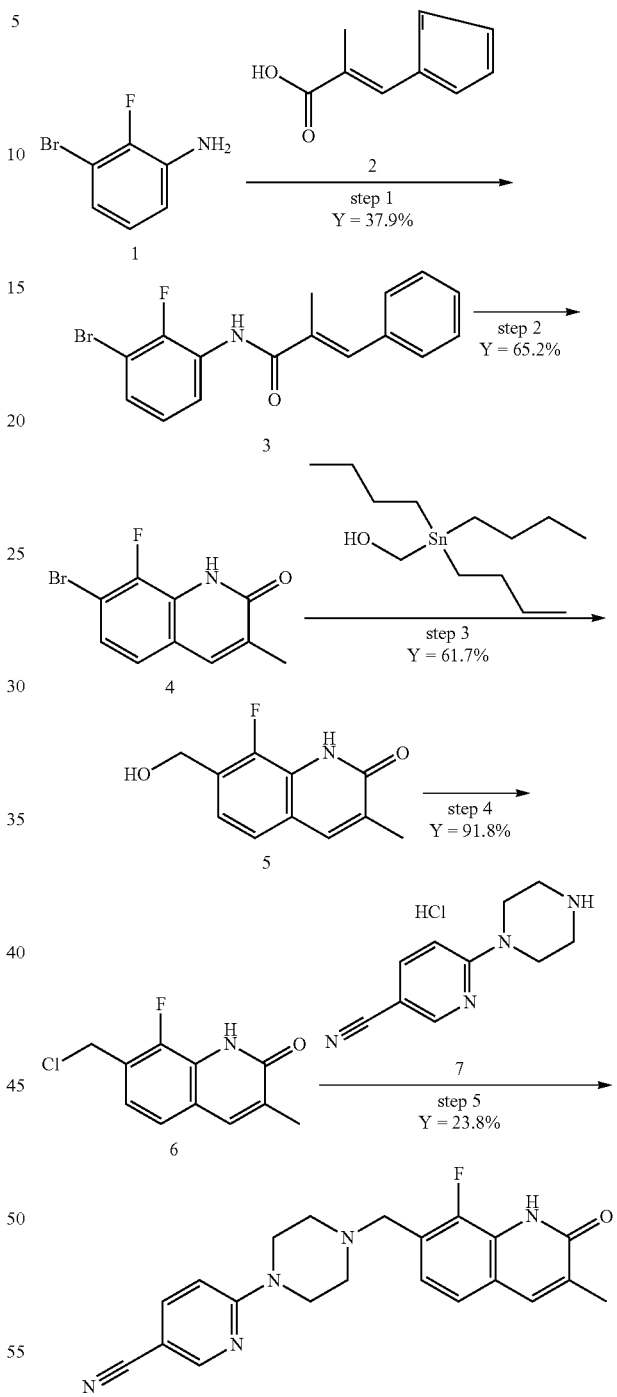

Example 71

Step 1: Preparation of (2E)-N-(3-bromo-2-fluorophenyl)-2-methyl-3-phenylprop-2-enamide A solution of α-methylcinnamic acid (2.56 g, 15.78 mmol, 1.00 equiv.) in DCM (30 mL) was treated with DIEA (8.16 g, 63.15 mmol, 4.00 equiv.), T$_3$P (15.07 g, 23.68 mmol, 1.50 equiv., 50 wt % in DCM) for 5 min at room temperature under nitrogen atmosphere followed by the addition of 3-bromo-2-fluoroaniline (3.00 g, 15.78 mmol, 1.00 equiv.) at room temperature. The resulting mixture was stirred overnight at room temperature under nitrogen atmosphere. The reaction was monitored by LCMS. The resulting mixture was diluted with water (100 mL). The resulting mixture was extracted with EtOAc (3×100 mL). The combined organic layers were washed with brine (2×100 mL), dried over anhydrous $Na_2SO_4$. After filtration, the filtrate was concentrated under reduced pressure. The residue was purified by silica gel column chromatography to afford (2E)-N-(3-bromo-2-fluorophenyl)-2-methyl-3-phenylprop-2-enamide (2.00 g, 37.9%). LC-MS: (ES+H, m/z): $[M+H]^+$=333.95/335.95; $^1H$ NMR (400 MHz, DMSO-$d_6$) δ 9.89 (s, 1H), 7.62-7.41 (m, 7H), 7.21-7.13 (m, 1H), 6.85-6.69 (m, 1H), 2.12 (d, J=1.4 Hz, 3H).

Step 2: Preparation of 7-bromo-8-fluoro-3-methyl-1H-quinolin-2-one

To a stirred solution (2E)-N-(3-bromo-2-fluorophenyl)-2-methyl-3-phenylprop-2-enamide (2.00 g, 5.98 mmol, 1.00 equiv.) in chlorobenzene (20 mL) was added $AlCl_3$ (2.39 g, 17.95 mmol, 3.00 equiv.) at 0° C. under nitrogen atmosphere. The resulting mixture was stirred for 3 h at 120° C. under nitrogen atmosphere. The reaction was monitored by LCMS. The mixture was allowed to cool down to room temperature. The resulting mixture was concentrated under reduced pressure. The residue was purified by silica gel column chromatography to afford 7-bromo-8-fluoro-3-methyl-TH-quinolin-2-one (1.00 g, 65.2%). LC-MS: (ES+H, m/z): $[M+H]^+$=255.80/257.80; $^1H$ NMR (400 MHz, DMSO-$d_6$) δ 11.94 (s, 1H), 7.82 (s, 1H), 7.44-7.34 (m, 2H), 2.09 (s, 3H).

Step 3: Preparation of 8-fluoro-7-(hydroxymethyl)-3-methyl-1H-quinolin-2-one

A solution of 7-bromo-8-fluoro-3-methyl-1H-quinolin-2-one (800 mg, 3.12 mmol, 1.00 equiv.) and (tributylstannyl)methanol (1.10 g, 3.43 mmol, 1.10 equiv.), 2nd Generation XPhos Precatalyst (123 mg, 0.15 mmol, 0.05 equiv.) in 1,4-dioxane (10 mL) was stirred overnight at 80° C. under nitrogen atmosphere. The reaction was monitored by LCMS. The mixture was allowed to cool down to room temperature. The resulting mixture was concentrated under reduced pressure. The residue was purified by silica gel column chromatography to afford 8-fluoro-7-(hydroxymethyl)-3-methyl-1H-quinolin-2-one (400 mg, 61.7%). LC-MS: (ES+H, m/z): $[M+H]^+$=208.15

Step 4: Preparation of 7-(chloromethyl)-8-fluoro-3-methyl-1H-quinolin-2-one

To a stirred solution 8-fluoro-7-(hydroxymethyl)-3-methyl-1H-quinolin-2-one (400 mg, 1.93 mmol, 1.00 equiv.) and DMF (14 mg, 0.19 mmol, 0.10 equiv.) in DCM (5 mL) was added $SOCl_2$ (2.30 g, 19.30 mmol, 10.00 equiv.) dropwise at 0° C. under nitrogen atmosphere. The resulting mixture was stirred for 2 h at room temperature under nitrogen atmosphere. The reaction was monitored by LCMS. The resulting mixture was concentrated under reduced pressure to afford 7-(chloromethyl)-8-fluoro-3-methyl-1H-quinolin-2-one (400 mg, 91.8%). LC-MS: (ES+H, m/z): $[M+H]^+$=226.3

Step 5: Preparation of 6-{4-[(8-fluoro-3-methyl-2-oxo-1H-quinolin-7-yl)methyl] piperazin-1-yl}pyridine-3-carbonitrile A solution of 6-(piperazin-1-yl)pyridine-3-carbonitrile hydrochloride (229 mg, assumed 100% yield, 0.88 mmol, 1.00 equiv.) in MeCN (10 mL) was treated with DIEA (573 mg, 4.43 mmol, 5.00 equiv.) for 5 min at room temperature under nitrogen atmosphere followed by the addition of KI (17 mg, 0.10 mmol, 0.10 equiv.) and 7-(chloromethyl)-8-fluoro-3-methyl-1H-quinolin-2-one (200 mg, 0.88 mmol, 1.00 equiv.). The resulting mixture was stirred for 2 h at 100° C. under nitrogen atmosphere. The reaction was monitored by LCMS. The mixture was allowed to cool down to room temperature. The resulting mixture was concentrated under reduced pressure. The residue was purified by silica gel column chromatography to afford 6-{4-[(8-fluoro-3-methyl-2-oxo-TH-quinolin-7-yl)methyl] piperazin-1-yl} pyridine-3-carbonitrile (92.1 mg, 23.8%). LC-MS: (ES+H, m/z): $[M+H]^+$=378.10; $^1H$ NMR (400 MHz, DMSO-$d_6$) δ 11.77 (s, 1H), 8.47 (d, J=4.0 Hz, 1H), 7.87-7.76 (m, 2H), 7.38 (d, J=8.1 Hz, 1H), 7.18 (dd, J=8.1, 6.4 Hz, 1H), 6.91 (d, J=8.0 Hz, 1H), 3.66-3.65 (m, 6H), 2.51-2.48 (m, 4H), 2.10 (d, J=1.3 Hz, 3H). $^{19}F$ NMR (377 MHz, DMSO-$d_6$) δ−135.84.

Example 82

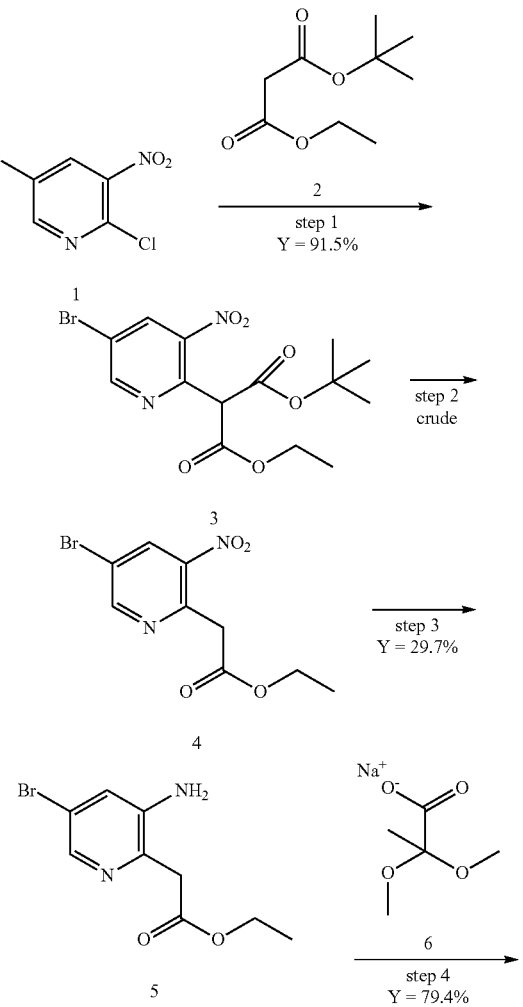

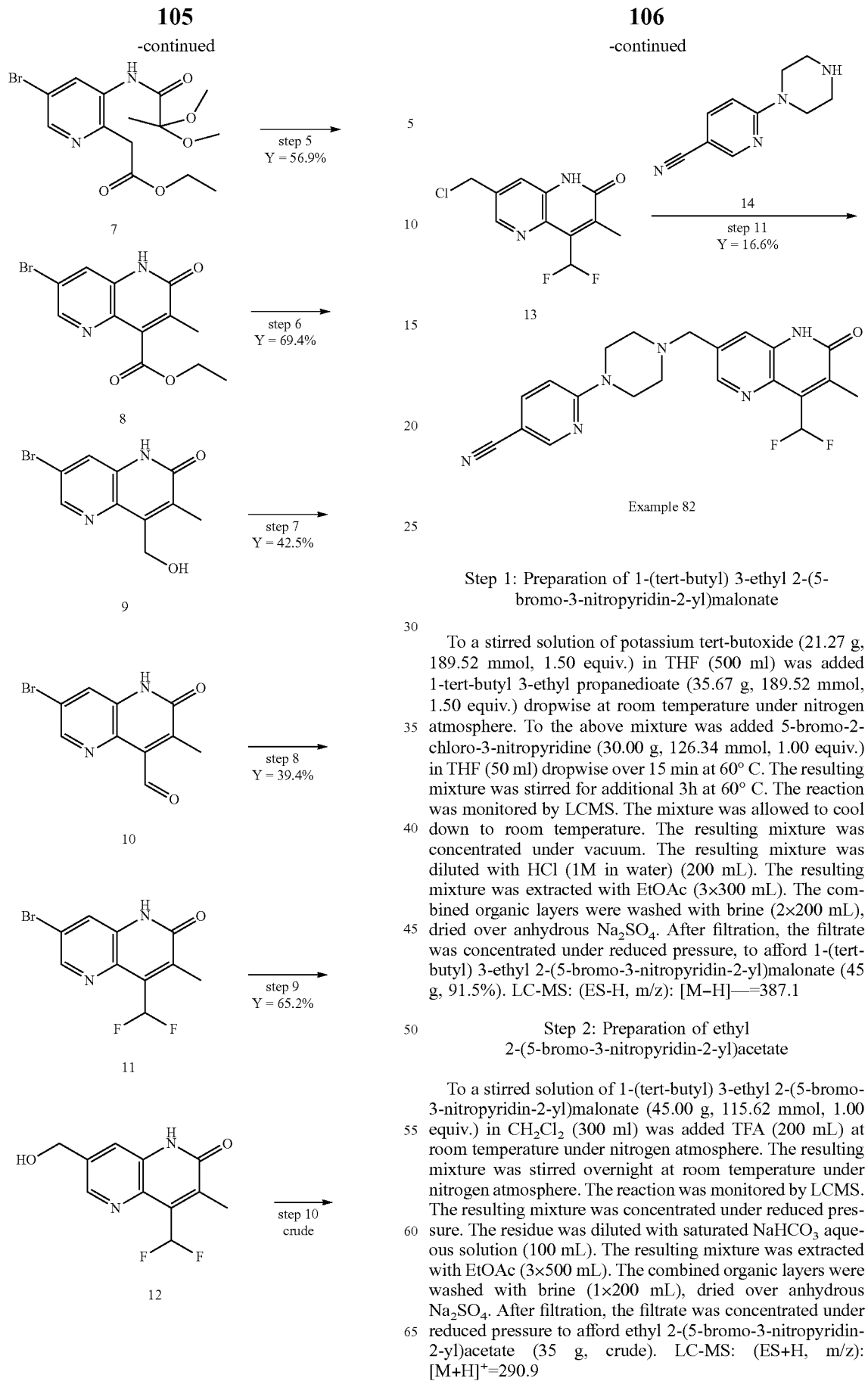

Example 82

Step 1: Preparation of 1-(tert-butyl) 3-ethyl 2-(5-bromo-3-nitropyridin-2-yl)malonate To a stirred solution of potassium tert-butoxide (21.27 g, 189.52 mmol, 1.50 equiv.) in THF (500 ml) was added 1-tert-butyl 3-ethyl propanedioate (35.67 g, 189.52 mmol, 1.50 equiv.) dropwise at room temperature under nitrogen atmosphere. To the above mixture was added 5-bromo-2-chloro-3-nitropyridine (30.00 g, 126.34 mmol, 1.00 equiv.) in THF (50 ml) dropwise over 15 min at 60° C. The resulting mixture was stirred for additional 3h at 60° C. The reaction was monitored by LCMS. The mixture was allowed to cool down to room temperature. The resulting mixture was concentrated under vacuum. The resulting mixture was diluted with HCl (1M in water) (200 mL). The resulting mixture was extracted with EtOAc (3×300 mL). The combined organic layers were washed with brine (2×200 mL), dried over anhydrous $Na_2SO_4$. After filtration, the filtrate was concentrated under reduced pressure, to afford 1-(tert-butyl) 3-ethyl 2-(5-bromo-3-nitropyridin-2-yl)malonate (45 g, 91.5%). LC-MS: (ES-H, m/z): [M−H]−=387.1

Step 2: Preparation of ethyl 2-(5-bromo-3-nitropyridin-2-yl)acetate

To a stirred solution of 1-(tert-butyl) 3-ethyl 2-(5-bromo-3-nitropyridin-2-yl)malonate (45.00 g, 115.62 mmol, 1.00 equiv.) in $CH_2Cl_2$ (300 ml) was added TFA (200 mL) at room temperature under nitrogen atmosphere. The resulting mixture was stirred overnight at room temperature under nitrogen atmosphere. The reaction was monitored by LCMS. The resulting mixture was concentrated under reduced pressure. The residue was diluted with saturated $NaHCO_3$ aqueous solution (100 mL). The resulting mixture was extracted with EtOAc (3×500 mL). The combined organic layers were washed with brine (1×200 mL), dried over anhydrous $Na_2SO_4$. After filtration, the filtrate was concentrated under reduced pressure to afford ethyl 2-(5-bromo-3-nitropyridin-2-yl)acetate (35 g, crude). LC-MS: (ES+H, m/z): [M+H]+=290.9

Step 3: Preparation of ethyl 2-(3-amino-5-bromopyridin-2-yl)acetate

To a stirred solution of ethyl 2-(5-bromo-3-nitropyridin-2-yl)acetate (35.00 g, 121.07 mmol, 1.00 equiv.) and Fe (79.72 g, 1219.36 mmol, 7.50 equiv.) in EtOH (250 ml) were added saturated NH₄Cl aqueous solution (250 mL) at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was diluted with EtOAc (300 mL). The resulting mixture was stirred for 10 min at room temperature. The resulting mixture was filtered, the filter cake was washed with EtOAc (3×70 mL). The resulting mixture was extracted with EtOAc (3×300 mL). The combined organic layers were washed with brine (2×200 mL), then dried over anhydrous Na₂SO₄. After filtration, the filtrate was concentrated under reduced pressure. The residue was purified by silica gel column chromatography to afford ethyl 2-(3-amino-5-bromopyridin-2-yl)acetate (9.3 g, 29.7%) as a light yellow oil. LC-MS: (ES+H, m/z): [M+H]⁺=259.1

Step 4: Preparation of ethyl 2-(5-bromo-3-(2,2-dimethoxypropanamido)pyridin-2-yl)acetate To a stirred solution of methyl 2,2-dimethoxypropanoate (12.00 g, 80.99 mmol, 1.00 equiv.) in MeOH (120 mL) were added NaOH (9.72 g, 242.98 mmol, 3.00 equiv.) in H₂O (120 mL) dropwise at room temperature under nitrogen atmosphere. The resulting mixture was stirred for 4 h at room temperature under nitrogen atmosphere. The reaction was monitored by TLC. The mixture was acidified to pH 8 with HCl (2M in water). The resulting mixture was concentrated under reduced pressure. The resulting mixture was diluted with EtOH (500 mL). The resulting mixture was stirred for 2 h at room temperature. The resulting mixture was filtered, the filter cake was washed with EtOH (3×100 mL). The filtrate was concentrated under reduced pressure to afford sodium 2,2-dimethoxypropanoate (8.5 g, 78.2%). ¹H NMR (300 MHz, D₂O) δ 3.12 (d, J=1.7 Hz, 6H), 1.33 (s, 3H).

To a stirred solution of sodium 2,2-dimethoxypropanoate (7.59 g, 48.63 mmol, 1.50 equiv.) in dioxane (100 ml) were added DIEA (12.57 g, 97.26 mmol, 3.00 equiv.) and T₃P (30.95 g, 97.26 mmol, 3.00 equiv, 50 wt % in EtOAc) at room temperature under nitrogen atmosphere. The resulting mixture was stirred for 1 h at room temperature under nitrogen atmosphere. To the above mixture was added ethyl 2-(3-amino-5-bromopyridin-2-yl)acetate (8.40 g, 32.42 mmol, 1.00 equiv.) at room temperature. The resulting mixture was stirred overnight at 100° C. The reaction was monitored by LCMS. The mixture was allowed to cool down to room temperature. The resulting mixture was diluted with water (100 mL). The resulting mixture was extracted with EtOAc (3×200 mL). The combined organic layers were washed with brine (1×100 mL), dried over anhydrous Na₂SO₄. After filtration, the filtrate was concentrated under reduced pressure. The residue was purified by silica gel column chromatography to afford ethyl 2-(5-bromo-3-(2,2-dimethoxypropanamido)pyridin-2-yl)acetate (9.3 g, 79.4%). LC-MS: (ES+H, m/z): [M+H]⁺=375.1

Step 5: Preparation of ethyl 7-bromo-3-methyl-2-oxo-1,2-dihydro-1,5-naphthyridine-4-carboxylate To a stirred solution of ethyl 2-(5-bromo-3-(2,2-dimethoxypropanamido)pyridin-2-yl)acetate (7.00 g, 18.65 mmol, 1.00 equiv.) in TFA (100 ml) were added H₂O (7 mL) and followed by 2 drops of 12 fresh solution (30 mg of 12 was suspended in TFA (10 mL)) at room temperature under nitrogen atmosphere. The resulting mixture was stirred overnight at 50° C. under nitrogen atmosphere. The resulting mixture was concentrated under vacuum. The residue was dissolved in toluene (100 mL) and piperidine (6 mL). The resulting mixture was refluxed at 120° C. for 2h, then concentrated under reduced pressure. The residue was purified by silica gel column chromatography to afford ethyl 7-bromo-3-methyl-2-oxo-1H-1,5-naphthyridine-4-carboxylate (3.3 g, 56.9%). LC-MS: (ES+H, m/z): [M+H]⁺=313.0; ¹H NMR (400 MHz, DMSO-d₆) δ 12.20 (s, 1H), 8.55 (d, J=2.1 Hz, 1H), 7.86 (d, J=2.1 Hz, 1H), 4.42 (q, J=7.1 Hz, 2H), 2.06 (s, 3H), 1.33 (t, J=7.1 Hz, 3H).

Step 6: Preparation of 7-bromo-4-(hydroxymethyl)-3-methyl-1,5-naphthyridin-2(1H)-one To a stirred solution of ethyl 7-bromo-3-methyl-2-oxo-1H-1,5-naphthyridine-4-carboxylate (3.00 g, 9.64 mmol, 1.00 equiv.) in THF (50 ml) were added LiEt₃BH (30 ml, 1M in THF) dropwise at OC under nitrogen atmosphere. The resulting mixture was stirred for 2 h at 0° C. under nitrogen atmosphere. The reaction was monitored by LCMS. The reaction was quenched by the addition of Water/ice (6 mL) at 0° C. The resulting mixture was concentrated under vacuum. The residue was purified by silica gel column chromatography, eluted with CH₂Cl₂/MeOH (0 to 10:1 gradient in 30 min) to afford 7-bromo-4-(hydroxymethyl)-3-methyl-1,5-naphthyridin-2(1H)-one (1.8 g, 69.4%). LC-MS: (ES-H, m/z): [M−H]⁻=267.0/269.0; ¹H NMR (300 MHz, DMSO-d₆) δ 11.95 (s, 1H), 8.57 (d, J=2.1 Hz, 1H), 7.83 (d, J=2.1 Hz, 1H), 5.04 (t, J=5.5 Hz, 1H), 4.90 (d, J=5.2 Hz, 2H), 2.21 (s, 3H).

Step 7: Preparation of 7-bromo-3-methyl-2-oxo-1,2-dihydro-1,5-naphthyridine-4-carbaldehyde To a stirred mixture of 7-bromo-4-(hydroxymethyl)-3-methyl-1,5-naphthyridin-2(1H)-one (1.80 g, 6.68 mmol, 1.00 equiv.) in THF (20 ml) was added 1,1-bis(acetyloxy)-3-oxo-3H-1l⁵[5],2-benziodaoxol-1-yl acetate (3.40 g, 8.02 mmol, 1.20 equiv.) at room temperature under nitrogen atmosphere. The resulting mixture was stirred for 2 h at room temperature under nitrogen atmosphere. The reaction was monitored by LCMS. The resulting mixture was diluted with water (10 mL). The precipitated solids were collected by filtration and washed with water (3×5 mL). The residue was purified by reversed combi-flash chromatography to afford 7-bromo-3-methyl-2-oxo-1,2-dihydro-1,5-naphthyridine-4-carbaldehyde (760 mg, 42.5%).LC-MS: (ES-H, m/z): [M−H]⁻=264.9; ¹H NMR (300 MHz, DMSO-d₆) δ 12.28 (s, 1H), 10.88 (s, 1H), 8.62 (d, J=2.1 Hz, 1H), 7.89 (d, J=2.1 Hz, 1H), 2.25 (s, 3H).

Step 8: Preparation of 7-bromo-4-(difluoromethyl)-3-methyl-1,5-naphthyridin-2(1H)-one To a stirred solution of 7-bromo-3-methyl-2-oxo-1,2-dihydro-1,5-naphthyridine-4-carbaldehyde (750 mg, 2.80 mmol, 1 equiv.) in THF (5 ml) were added BAST (2.49 g, 11.23 mmol, 4 equiv.) dropwise at 0° C. under nitrogen atmosphere. The resulting mixture was stirred for 2 h at 50° C. under nitrogen atmosphere. The reaction was monitored by LCMS. The mixture was allowed to cool down to room temperature. The reaction was quenched with sat. NH₄Cl (aq.) (3 ml) at 0° C. The resulting mixture was extracted with EtOAc (3×20 mL), dried over anhydrous $Na_2SO_4$. After filtration, the filtrate was concentrated under reduced pressure. The residue was purified by silica gel column chromatography to afford 7-bromo-4-(difluoromethyl)-3-methyl-1H-1,5-naphthyridin-2-one (320 mg, 39.4%). LC-MS: (ES-H, m/z): [M–H]—=287.0

Step 9: Preparation of 4-(difluoromethyl)-7-(hydroxymethyl)-3-methyl-1,5-naphthyridin-2(1H)-one To a stirred solution of 7-bromo-4-(difluoromethyl)-3-methyl-1H-1,5-naphthyridin-2-one (360 mg, 1.24 mmol, 1.00 equiv.) and 2nd GenerationXPhos Precatalyst/(195 mg, 0.24 mmol, 0.20 equiv.) in dioxane (5 ml) were added (Tributylstannyl)methanol (959 mg, 2.98 mmol, 2.40 equiv.) at room temperature under nitrogen atmosphere. The resulting mixture was stirred for 2 h at 80° C. under nitrogen atmosphere. The reaction was monitored by LCMS. The resulting mixture was concentrated under vacuum. The residue was purified by silica gel column chromatography to afford 4-(difluoromethyl)-7-(hydroxymethyl)-3-methyl-1,5-naphthyridin-2(1H)-one (195 mg, 65.2%). LC-MS: (ES+H, m/z): $[M+H]^+$=241.1.

Step 10: Preparation of 7-(chloromethyl)-4-(difluoromethyl)-3-methyl-1,5-naphthyridin-2(1H)-one To a stirred solution of 4-(difluoromethyl)-7-(hydroxymethyl)-3-methyl-1,5-naphthyridin-2(1H)-one (185 mg, 0.25 mmol, 1.00 equiv.) and DMF (2 mg, 0.02 mmol, 0.10 equiv.) in $CH_2Cl_2$ (3 ml) were added $SOCl_2$ (183 mg, 1.54 mmol, 6.00 equiv.) dropwise at 0° C. under nitrogen atmosphere. The resulting mixture was stirred overnight at room temperature under nitrogen atmosphere. The reaction was monitored by LCMS. The resulting mixture was concentrated under vacuum to afford 7-(chloromethyl)-4-(difluoromethyl)-3-methyl-1,5-naphthyridin-2(1H)-one (195 mg, crude). The crude product was used in the next step directly without further purification. LC-MS: (ES+H, m/z): $[M+H]^+$=259.0

Step 11: Preparation of 6-(4-((8-(difluoromethyl)-7-methyl-6-oxo-5,6-dihydro-1,5-naphthyridin-3-yl)methyl)piperazin-1-yl)nicotinonitrile To a stirred solution of 7-(chloromethyl)-4-(difluoromethyl)-3-methyl-1,5-naphthyridin-2(1H)-one (104 mg, 0.40 mmol, 1.00 equiv.) and 6-(piperazin-1-yl)pyridine-3-carbonitrile (91 mg, 0.48 mmol, 1.20 equiv.) in MeCN (5 ml) were added DIEA (260 mg, 2.01 mmol, 5.00 equiv.) and KI (13 mg, 0.08 mmol, 0.20 equiv.) at room temperature under nitrogen atmosphere. The resulting mixture was stirred for 3 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford 6-(4-((8-(difluoromethyl)-7-methyl-6-oxo-5,6-dihydro-1,5-naphthyridin-3-yl)methyl)piperazin-1-yl)nicotinonitrile (crude). The crude product was further purified by trituration with MeOH (6 mL) to afford 6-(4-((8-(difluoromethyl)-7-methyl-6-oxo-5, 6-dihydro-1,5-naphthyridin-3-yl)methyl)piperazin-1-yl) nicotinonitrile (28.3 mg, 16.6%). LC-MS: (ES+H, m/z): $[M+H]^+$=411.10; $^1$H NMR (300 MHz, DMSO-$d_6$) δ 12.25 (s, 1H), 8.48 (t, J=1.8 Hz, 2H), 8.14-7.74 (m, 2H), 7.70 (d, J=1.9 Hz, 1H), 6.94 (d, J=9.1 Hz, 1H), 3.39-3.67 (m, 6H), 2.50-2.48 (m, 4H), 2.33 (t, J=2.8 Hz, 3H). $^{19}$F NMR (282 MHz, DMSO-$d_6$) δ–117.71.

Example 83

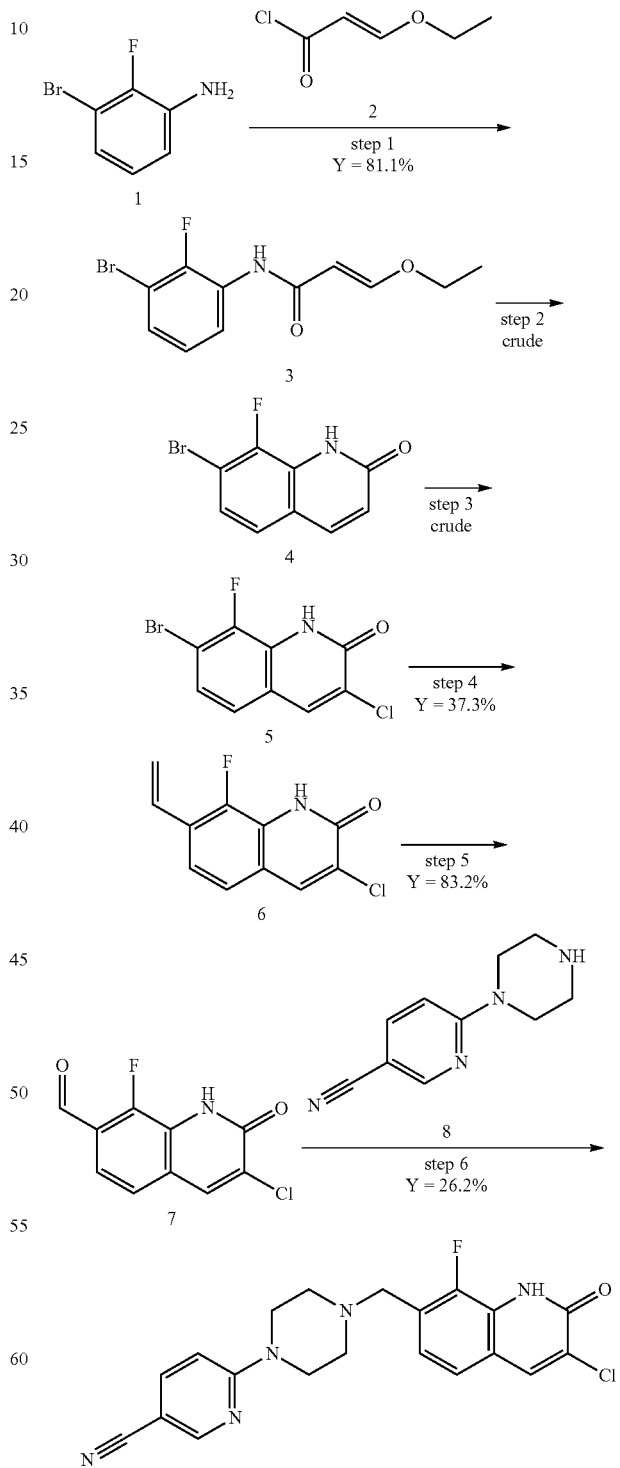

Example 83

Step 1: Preparation of (2E)-N-(3-bromo-2-fluorophenyl)-3-ethoxyprop-2-enamide To a stirred mixture of 3-bromo-2-fluoroaniline (20.00 g, 105.25 mmol, 1.00 equiv.) in DCM (300 mL) was added pyridine (14.99 g, 189.45 mmol, 1.80 equiv.) dropwise at room temperature under nitrogen atmosphere. The resulting mixture was stirred for 5 min at room temperature under nitrogen atmosphere. To the above mixture was added (2E)-3-ethoxyprop-2-enoyl chloride (21.24 g, 157.88 mmol, 1.50 equiv.) dropwise over 5 min at room temperature. The resulting mixture was stirred for additional 2h at room temperature. The reaction was monitored by LCMS. The resulting mixture was concentrated under reduced pressure. The residue was dissolved in EtOAc (500 mL). The resulting mixture was washed with water (3×500 mL). The resulting mixture was concentrated under reduced pressure. The residue was purified by silica gel column chromatography to afford (2E)-N-(3-bromo-2-fluorophenyl)-3-ethoxyprop-2-enamide (24.6 g, 81.1%). LC-MS: (ES+H, m/z): [M+H]$^+$=288.0/290.0.

Step 2: Preparation of 7-bromo-8-fluoro-1H-quinolin-2-one

A mixture of (2E)-N-(3-bromo-2-fluorophenyl)-3-ethoxyprop-2-enamide (17.00 g, 59.00 mmol, 1.00 equiv.) in $H_2SO_4$ (85 mL) was stirred for 3 h at room temperature under nitrogen atmosphere. The resulting mixture was added to ice water (1 L) dropwise and stirred for 1 h. The precipitated solids were collected by filtration and washed with water (3×200 mL). The resulting mixture was concentrated under reduced pressure to afford 7-bromo-8-fluoro-1H-quinolin-2-one (14.30 g, crude). LC-MS: (ES+H, m/z): [M+H]$^+$=242.0/244.0.

Step 3: Preparation of 7-bromo-3-chloro-8-fluoro-1H-quinolin-2-one

To a stirred mixture of 7-bromo-8-fluoro-1H-quinolin-2-one (3.00 g, 12.39 mmol, 1.00 equiv.) and NCS (2.65 g, 19.83 mmol, 1.60 equiv.) in $CH_3COOH$ (50 mL) was added 2,2-dichloroacetic acid (0.32 g, 2.47 mmol, 0.20 equiv.) dropwise at room temperature under nitrogen atmosphere. The resulting mixture was stirred overnight at 100° C. under nitrogen atmosphere. The reaction was monitored by LCMS. The mixture was allowed to cool down to room temperature. The resulting mixture was concentrated under reduced pressure. The residue was purified by silica gel column chromatography to afford 7-bromo-3-chloro-8-fluoro-1H-quinolin-2-one (2.48 g, crude). LC-MS: (ES+H, m/z): [M+H]$^+$=275.9/277.9; $^1$H NMR (400 MHz, DMSO-d$_6$) δ 12.52 (s, 1H), 8.38 (d, J=1.6 Hz, 1H), 7.52-7.42 (m, 2H).

Step 4: Preparation of 3-chloro-7-ethenyl-8-fluoro-1H-quinolin-2-one

To a stirred mixture of 7-bromo-3-chloro-8-fluoro-1H-quinolin-2-one (2.48 g, 8.97 mmol, 1.00 equiv.), CsF (4.09 g, 26.91 mmol, 3.00 equiv.), Pd(dppf)Cl$_2$ (0.33 g, 0.44 mmol, 0.05 equiv.) and 2-ethenyl-4,4,5,5-tetramethyl-1,3,2-dioxaborolane (1.38 g, 8.97 mmol, 1.00 equiv.) in dioxane (50 mL) was added $H_2O$ (5 mL) dropwise at room temperature under nitrogen atmosphere. The resulting mixture was stirred for 2 h at 100° C. under nitrogen atmosphere. The reaction was monitored by LCMS. The mixture was allowed to cool down to room temperature. The resulting mixture was concentrated under reduced pressure. The residue was purified by silica gel column chromatography to afford 3-chloro-7-ethenyl-8-fluoro-1H-quinolin-2-one (750 mg, 37.3%). LC-MS: (ES+H, m/z): [M+H]$^+$=224.0; $^1$H NMR (300 MHz, DMSO-d$_6$) δ 12.38 (s, 1H), 8.34 (d, J=1.6 Hz, 1H), 7.53-7.46 (m, 2H), 6.95 (dd, J=17.7, 11.2 Hz, 1H), 6.07 (dd, J=17.7, 1.0 Hz, 1H), 5.57 (dd, J=11.2, 1.0 Hz, 1H).

Step 5: Preparation of 3-chloro-8-fluoro-2-oxo-1H-quinoline-7-carbaldehyde

To a stirred mixture of 3-chloro-7-ethenyl-8-fluoro-1H-quinolin-2-one (750 mg, 3.35 mmol, 1.00 equiv.), $K_2OsO_2(OH)_4$ (123 mg, 0.33 mmol, 0.10 equiv.), NaIO$_4$ (2.87 g, 13.41 mmol, 4.00 equiv.) and 2,6-dimethylpyridine (718 mg, 6.70 mmol, 2.00 equiv.) in THF (15 mL) was added $H_2O$ (1.5 mL) dropwise at room temperature under nitrogen atmosphere. The resulting mixture was stirred overnight at room temperature under nitrogen atmosphere. The reaction was monitored by LCMS. The resulting mixture was concentrated under reduced pressure. The residue was purified by silica gel column chromatography to afford 3-chloro-8-fluoro-2-oxo-1H-quinoline-7-carbaldehyde (630 mg, 83.2%). LC-MS: (ES-H, m/z): [M-H]—=224.1.

Step 6: Preparation of 6-{4-[(3-chloro-8-fluoro-2-oxo-1H-quinolin-7-yl)methyl]piperazin-1-yl}pyridine-3-carbonitrile A mixture of 3-chloro-8-fluoro-2-oxo-1H-quinoline-7-carbaldehyde (150 mg, 0.66 mmol, 1.00 equiv.) and 6-(piperazin-1-yl)pyridine-3-carbonitrile (137 mg, 0.73 mmol, 1.10 equiv.) in DCM(2 ml) was stirred for 10 min at room temperature. The resulting mixture was concentrated under reduced pressure. The resulting mixture was added HOAc (19 mg, 0.33 mmol, 0.50 equiv.) in EtOH (3 mL) and stirred for 4 h at 50° C. under nitrogen atmosphere. The mixture was allowed to cool down to room temperature. To the stirred mixture was added NaBH$_3$CN (83 mg, 1.33 mmol, 2.00 equiv.) in portions at 0° C. under nitrogen atmosphere. The resulting mixture was stirred overnight at room temperature under nitrogen atmosphere. The precipitated solids were collected by filtration and washed with EtOH (3×2 mL). The residue was purified by silica gel column chromatography. The resulting mixture was concentrated under reduced pressure to afford 6-{4-[(3-chloro-8-fluoro-2-oxo-1H-quinolin-7-yl)methyl]piperazin-1-yl}pyridine-3-carbonitrile (69.3 mg, 26.2%). LC-MS: (ES+H, m/z): [M+H]$^+$=398.10; $^1$H NMR (400 MHz, DMSO-d$_6$) δ 12.46 (s, 1H), 8.47 (d, J=2.0 Hz, 1H), 8.36 (d, J=1.5 Hz, 1H), 7.85 (dd, J=9.1, 2.4 Hz, 1H), 7.49 (d, J=8.1 Hz, 1H), 7.28 (dd, J=8.1, 6.3 Hz, 1H), 6.97-36.87 (t, 1H), 3.71-3.63 (m, 6H), 2.50-2.44 (m, 4H); $^{19}$F NMR (282 MHz, DMSO-d6) δ−134.50.

The following compound were synthesized as described above.

TABLE 2

Characterization Data

| Ex. | NMR | MS | Synthesized as described in Example |
|---|---|---|---|
| 4 | 1H NMR (400 MHz, DMSO-$d_6$) δ 11.85 (s, 1H), 8.43 (d, 1H), 8.08 (d, 1H), 7.75 (t, 1H), 7.62 (d, 1H), 7.53-7.45 (m, 1H), 6.86 (dd, 1H), 3.63 (t, 2H), 3.47-3.41 (m, 4H), 2.60-2.56 (m, 2H), 2.53-2.46 (m, 4H), 1.19 (t, 3H) | $[M + H]^+$ = 368.15 | 3 |
| 6 | $^1$H NMR (400 MHz, DMSO-$d_6$) δ 11.86 (s, 1H), 8.47 (d, 1H), 8.39 (d, 1H), 7.87-7.81 (m, 2H), 7.61 (d, 1H), 6.93 (d, 1H), 3.67 (t, 4H), 3.63 (s, 2H), 2.50-2.45(m, 4H), 2.14 (d, 3H) | $[M + H]^+$ = 361.2 | 3 |
| 7 | $^1$H NMR (400 MHz, DMSO-$d_6$) δ 11.84 (s, 1H), 8.40 (d, 1H), 8.16 (d, 1H), 7.75 (s, 1H), 7.71-7.56 (m, 2H), 6.82 (d, 1H), 3.62 (s, 2H), 3.54-3.40 (m, 4H), 2.59-2.52 (m, 2H), 2.50-2.44 (m, 4H), 1.24-1.13 (m, 3H) | $[M + H]^+$ = 428.1 | 3 |
| 8 | $^1$H NMR (300 MHz, DMSO-$d_6$) δ 11.85 (s, 1H), 8.40 (d, 1H), 8.10 (d, 1H), 7.75 (s, 1H), 7.66-7.54 (m, 2H), 6.86 (d, 1H), 3.63 (s, 2H), 3.52-3.45 (m, 4H), 2.60-2.52 (m, 2H), 2.50-2.46 (m, 4H), 1.19 (t, 3H) | $[M + H]^+$ = 384.1 | 3 |
| 9 | $^1$H NMR (400 MHz, DMSO-$d_6$) δ 11.86 (s, 1H), 8.40 (d, 1H), 7.75 (s, 1H), 7.62 (d, 1H), 7.58 (d, 2H), 7.05-6.99 (m, 2H), 3.64 (s, 2H), 3.4-3.35 (m, 4H), 2.57-2.51 (m, 6H), 1.18 (t, 3H) | $[M + H]^+$ = 374.20 | 3 |
| 10 | $^1$H NMR (400 MHz, DMSO-$d_6$) δ 11.85 (s, 1H), 8.48 (d, 1H), 8.40 (d, 1H), 7.85 (dd, 1H), 7.75 (s, 1H), 7.62 (d, 1H), 7.05-6.93 (m, 1H), 3.69-3.64 (m, 4H), 3.63 (s, 2H), 2.57-2.55 (m, 2H), 2.53-2.48 (m, 4H), 1.18 (t, 3H) | $[M + H]^+$ = 375.05 | 3 |
| 11 | 1H NMR (300 MHz, DMSO-$d_6$) δ 11.86 (s, 1H), 8.40 (dd, 2H), 7.83 (s, 1H), 7.75 (d, 1H), 7.61 (d, 1H), 7.36 (dd, 1H), 3.64 (s, 2H), 3.42 (t, 4H), 2.53 (m, 4H), 2.14 (s, 3H) | $[M + H]^+$ = 361.1 | 3 |
| 13 | $^1$H NMR (400 MHz, DMSO-$d_6$) δ 11.86 (s, 1H), 8.39 (d, J = 1.8 Hz, 1H), 7.83 (d, J = 1.6 Hz, 1H), 7.77 (dd, J = 13.1, 6.3 Hz, 1H), 7.60 (d, J = 1.9 Hz, 1H), 7.09 (dd, J = 12.0, 7.2 Hz, 1H), 3.63 (s, 2H), 3.30-3.26 (m, 4H), 2.57-2.54 (m, 4H), 2.14 (d, J = 1.3 Hz, 3H). $^{19}$F NMR (377 MHz, DMSO-$d_6$) δ −111.68, −111.72, −124.88, −124.92. | $[M + H]^+$ = 396.2 | 3 |
| 14 | $^1$H NMR (400 MHz, DMSO-$d_6$) δ 11.84 (s, 1H), 8.43 (d, 1H), 8.35 (d, 1H), 7.80-7.73 (m, 2H), 7.65 (d, 1H), 7.25 (dd, 1H), 3.95-3.81 (m, 2H), 3.60-3.52 (m, 1H), 3.27-3.15 (m, 1H), 2.83-2.69 (m, 2H), 2.60-2.51 (m, 4H), 1.25-1.16 (m, 3H), 0.82-0.78 (m, 1H), 0.42-0.38 (m, 1H) | $[M + H]^+$ = 387.2 | 3 |
| 15 | $^1$H NMR (300 MHz, DMSO-$d_6$) δ 11.86 (s, 1H), 8.50 (d, 1H), 8.43 (d, 1H), 7.91 (dd, 1H), 7.75 (s, 1H), 7.66 (s, 1H), 6.89 (d, 1H), 4.31 (brs, 1H), 3.94-3.75 (m, 2H), 3.16-2.99 (m, 1H), 2.93-2.71 (m, 2H), 2.69-2.52 (m, 3H), 2.42-2.16 (m, 1H), 1.18 (t, 3H), 0.75 (q, 1H), 0.51 (q, 1H) | $[M + H]^+$ = 387.2 | 3 |
| 17 | $^1$H NMR (400 MHz, DMSO-$d_6$) δ 11.88 (s, 1H), 8.47 (d, 1H), 8.37 (d, 1H), 7.84 (dd, 1H), 7.60 (d, 1H), 7.42 (s, 1H), 6.93 (d, 1H), 3.69-3.64 (m, 4H), 3.62 (s, 2H), 2.54-2.49 (m, 4H), 2.20-2.09 (m, 1H), 1.00-0.93 (m, 2H), 0.85-0.79 (m, 2H) | $[M + H]^+$ = 387.3 | 16 |
| 18 | $^1$H NMR (300 MHz, DMSO-$d_6$) δ 11.87 (s, 1H), 8.40 (d, 1H), 7.83 (d, 1H), 7.70 (dd, 1H), 7.64-7.52 (m, 2H), 7.13 (t, 1H), 3.65 (s, 2H), 3.20 (t, 4H), 2.56 (t, 4H), 2.14 (d, 3H) $^{19}$F NMR (282 MHz, DMSO-$d_6$) δ −119.88 | $[M + H]^+$ = 378.15 | 3 |
| 19 | $^1$H NMR (300 MHz, DMSO-$d_6$) δ 11.87 (s, 1H), 8.50 (d, 1H), 8.43 (d, 1H), 7.91 (m, 1H), 7.83 (d, 1H), 7.66 (d, 1H), 6.89 (d, 1H), 4.32 (s, 1H), 3.95-3.73 (m, 2H), 3.05 (t, 1H), 2.92-2.70 (m, 2H), 2.62 (d, 1H), 2.32 (t, 1H), 2.14 (d, 3H), 0.75 (q, 1H), 0.51 (q, 1H) | $[M + H]^+$ = 373.10 | 3 |
| 20 | $^1$H NMR (300 MHz, DMSO-$d_6$) δ 11.89 (s, 1H), 8.50 (d, 1H), 8.41 (d, 1H), 7.92 (dd, 1H), 7.64 (d, 1H), 7.42 (s, 1H), 6.89 (d, 1H), 4.32 | $[M + H]^+$ = 399.20 | 16 |

TABLE 2-continued

Characterization Data

| Ex. | NMR | MS | Synthesized as described in Example |
|---|---|---|---|
| | (s, 1H), 3.93-3.72 (m, 2H), 3.05 (t, 1H), 2.91-2.71 (m, 2H), 2.62 (q, 1H), 2.34 (d, 1H), 2.16-2.11 (m, 1H), 1.04-0.92 (m, 2H), 0.87-0.68 (m, 3H), 0.50 (q, 1H) | | |
| 21 | $^1$H NMR (300 MHz, DMSO-$d_6$) δ 11.92 (s, 1H), 8.49-8.48 (d, 1H), 8.41-8.40 (d, 1H), 7.87-7.83 (dd, 1H), 7.75 (s, 1H), 7.67 (d, 1H), 6.89-6.86 (d, 1H), 4.59 (m, 1H), 4.24-4.20 (d, 1H), 3.72-3.68 (d, 1H), 3.57-3.52 (d, 1H), 3.17-3.13 (td, 1H), 2.95-2.91 (d, 1H), 2.73-2.70 (d, 1H), 2.58-2.51 (m, 2H), 2.28-2.05 (m, 2H), 1.22-1.16 (m, 6H) | $[M + H]^+$ = 389.15 | 3 |
| 22 | $^1$H NMR (300 MHz, DMSO-$d_6$) δ 11.90 (s, 1H), 8.39 (d, 1H), 8.08 (d, 1H), 7.65 (d, 1H), 7.55-7.35 (m, 2H), 6.78 (dd, 1H), 4.46-4.34 (m, 1H), 3.92-3.88 (m, 1H), 3.74-3.62 (m, 1H), 3.58-3.46 (m, 1H), 3.08-2.95 (m, 1H), 2.92-2.88 (m, 1H), 2.70-2.68(m, 1H), 2.26-2.08 (m, 3H), 1.12 (d, 3H), 1.01-0.92 (m, 2H), 0.85-0.77 (m, 2H)<br>$^{19}$F NMR (282 MHz, DMSO-$d_6$) δ −144.32 | $[M +H]^+$ = 394.20 | 16 |
| 23 | $^1$H NMR (300 MHz, DMSO-$d_6$) δ 11.89 (s, 1H), 8.41 (d, 1H), 8.08 (d, 1H), 7.83 (d, 1H), 7.67 (d, 1H), 7.52-7.44 (m, 1H), 6.78 (dd, 1H), 4.45-4.35 (m, 1H), 3.90 (d, 1H), 3.74-3.64 (m, 1H), 3.60-3.49 (m, 1H), 3.09-2.96 (m, 1H), 2.91 (d, 1H), 2.70 (d, 1H), 2.28-2.21 (m, 1H), 2.20-2.06 (m, 4H), 1.13 (d, 3H)<br>$^{19}$F NMR (282 MHz, DMSO-$d_6$) δ −144.32 | $[M + H]^+$ = 368.20 | 3 |
| 24 | $^1$H NMR (300 MHz, DMSO-$d_6$) δ 11.91 (s, 1H), 8.49-8.48 (d, 1H), 8.41-8.40 (d, 1H), 7.87-7.83 (m, 2H), 7.66 (d, 1H), 6.89-6.86 (d, 1H), 4.60 (s, 1H), 4.24-4.20 (d, 1H), 3.71-3.67 (d, 1H), 3.57-3.53 (d, 1H), 3.18-3.09 (td, 1H), 2.95-2.91 (d, 1H), 2.74-2.70 (d, 1H), 2.24-2.07 (m, 5H), 1.22 (d, 3H) | $[M + H]^+$ = 375.10 | 3 |
| 25 | $^1$H NMR (300 MHz, DMSO-$d_6$) δ 11.94 (s, 1H), 8.49-8.48 (d, 1H), 8.39-8.39 (d, 1H), 7.87-7.83 (dd, 1H), 7.65 (d, 1H), 7.42 (s, 1H), 6.89-6.86 (d, 1H), 4.59 (s, 1H), 4.24-4.20 (d, 1H), 3.71-3.67 (d, 1H), 3.56-3.51 (m, 1H), 3.17-3.13 (m, 1H), 2.94-2.91 (d, 1H), 2.73-2.69 (d, 1H), 2.23-2.07 (m, 3H), 1.22-1.20 (d, 3H), 1.01-0.94 (m, 2H), 0.85-0.80 (m, 2H) | $[M + H]^+$ = 401.25 | 16 |
| 26 | 1H NMR (300 MHz, DMSO-$d_6$) δ 11.87 (s, 1H), 8.39 (d, 1H), 8.10 (d, 1H), 7.86-7.74 (m, 2H), 7.62 (d, 1H), 3.63 (s, 2H), 3.31 (d, 4H), 2.55 (d, 4H), 2.14 (d, 3H)<br>$^{19}$F NMR (282 MHz, DMSO-$d_6$) δ −123.56, −136.44 | $[M + H]^+$ = 372.20 | 3 |
| 27 | $^1$H NMR (300 MHz, DMSO-$d_6$) δ 11.88 (s, 1H), 8.40 (d, 1H), 7.84 (d, 1H), 7.70 (d, 1H), 7.61 (d, 1H), 7.43 (d, 1H), 3.68 (s, 2H), 3.20-2.93 (m, 4H), 2.75-2.58 (m, 4H), 2.30 (tt, 1H), 2.14 (d, 3H), 1.11-0.93 (m, 4H) | $[M + H]^+$ = 401.15 | 3 |
| 30 | $^1$H NMR (400 MHz, DMSO-$d_6$) δ 11.87 (s, 1H), 8.43-8.36 (m, 2H), 8.00 (dd, 1H), 7.83 (s, 1H), 7.60 (s, 1H), 3.73-3.65 (m, 4H), 3.63 (s, 2H), 2.57-2.51 (m, 4H), 2.14 (s, 3H)<br>$^{19}$F NMR (377 MHz, DMSO-$d_6$) δ −127.13 | $[M + H]^+$ = 379.10 | 3 |
| 31 | $^1$H NMR (400 MHz, DMSO-$d_6$) δ 11.88 (s, 1H), 8.40 (s, 1H), 8.11 (d, 1H), 7.83 (d, 2H), 7.60 (s, 1H), 7.12 (t, 1H), 3.67 (s, 2H), 3.10-3.08 (m, 4H), 2.61-2.56 (m, 4H), 2.14 (d, 3H)<br>$^{19}$F NMR (377 MHz, DMSO-$d_6$) δ−116.453 | $[M + H]^+$ = 411.10 | 3 |
| 32 | $^1$H NMR (300 MHz, DMSO-$d_6$) δ 11.83 (s, 1H), 8.45 (m, 2H), 7.83 (m, 2H), 7.60 (d, 1H), 6.90 (d, 1H), 3.77-3.55 (m, 5H), 2.56 (d, 2H), 2.40 (m, 2H), 2.14 (s, 3H), 1.36 (d, 3H) | $[M + H]^+$ = 375.20 | 28 and 29 |
| 33 | $^1$H NMR (300 MHz, DMSO-$d_6$) δ 11.83 (s, 1H), 8.51-8.38 (m, 2H), 7.87-7.77 (m, 2H), 7.60 (d, 1H), 6.92-6.85 (m, 1H), 3.72-3.56 (m, 5H), 2.56 (d, 2H), 2.40 (m, 2H), 2.14 (d, 3H), 1.36 (d, 3H) | $[M + H]^+$ = 375.20 | 28 and 29 |

TABLE 2-continued

Characterization Data

| Ex. | NMR | MS | Synthesized as described in Example |
|---|---|---|---|
| 34 | ¹H NMR (400 MHz, DMSO-$d_6$) δ 11.85 (s, 1H), 8.40 (d, 1H), 7.81 (dd, 1H), 7.76-7.74 (m, 1H), 7.64-7.54 (m, 2H), 7.02 (dd, 1H), 3.65 (s, 2H), 3.62-3.16 (m, 4H), 2.59-2.54 (m, 6H), 1.18 (t, 3H)<br>¹⁹F NMR (377 MHz, DMSO-$d_6$) δ −80.70 | [M + H]⁺ = 368.1 | 3 |
| 35 | ¹H NMR (300 MHz, DMSO-$d_6$) δ 11.89 (s, 1H), 8.40 (d, 1H), 7.83 (d, 1H), 7.72 (dd, 1H), 7.61 (d, 1H), 7.51-7.48 (m, 1H), 7.22 (dd, 1H), 3.67 (s, 2H), 3.19-3.05 (m, 4H), 2.75-2.55 (m, 4H), 2.14 (d, 3H)<br>¹⁹F NMR (300 MHz, DMSO-$d_6$) δ −120.30 | [M + H]⁺ = 378.10 | 3 |
| 37 | ¹H NMR (400 MHz, DMSO-$d_6$) δ 11.87 (s, 1H), 8.47 (d, 1H), 8.39 (d, 1H), 7.88-7.81 (m, 2H), 7.61 (d, 1H), 6.93 (d, 1H), 3.66 (t, 4H), 2.48 (t,4H), 2.14 (d, 3H) | [M + H]⁺ = 363.15 | 3 |
| 38 | ¹H NMR (400 MHz, DMSO-$d_6$) δ 11.85 (s, 1H), 8.40 (d, 1H), 7.75 (s, 1H), 7.64-7.55 (m, 2H), 6.95 (dd, 1H), 6.85 (dd, 1H), 3.64 (s, 2H), 3.43-3.37 (m, 4H), 2.59-2.52 (m, 2H), 2.49-2.46 (m, 4H), 1.18 (t, 3H)<br>¹⁹F NMR (377 MHz, DMSO-$d_6$) δ −108.10 | [M + H]⁺ = 392.10 | 3 |
| 39 | ¹H NMR (400 MHz, DMSO-$d_6$) δ 11.85 (s, 1H), 8.39 (d, 1H), 7.74 (s, 1H), 7.61 (d, 1H), 7.34-7.32 (m, 2H), 6.95 (d, 1H), 3.82 (s, 3H), 3.63 (s, 2H), 3.10 (t, 4H), 2.56-2.50 (m, 6H), 1.18 (t, 3H) | [M + H]⁺ = 404.15 | 3 |
| 40 | ¹H NMR (300 MHz, DMSO-$d_6$) δ 11.87 (s, 1H), 8.41 (d, 1H), 7.75 (s, 1H), 7.72 (dd, 1H), 7.61 (d, 1H), 7.53-7.48 (m, 1H), 7.22 (dd, 1H), 3.67 (s, 2H), 3.10 (t, 4H), 2.60-2.53 (m, 6H), 1.19 (t, 3H)<br>¹⁹F NMR (300 MHz, DMSO-$d_6$) δ −120.30 | [M + H]⁺ = 392.10 | 3 |
| 41 | ¹H NMR (400 MHz, DMSO-$d_6$) δ 11.86 (s, 1H), 8.40 (d, 1H), 7.83-7.72 (m, 2H), 7.61 (d, 1H), 7.09 (dd, 1H), 3.64 (s, 2H), 3.30-3.21 (m, 4H), 2.61-2.51 (m, 6H), 1.18 (t, 3H)<br>¹⁹F NMR (377 MHz, DMSO-$d_6$) δ −111.70, −124.90 | [M + H]⁺ = 410.15 | 3 |
| 43 | ¹H NMR (400 MHz, DMSO-$d_6$) δ 11.88 (br, 1H), 8.39 (d, 1H), 7.83 (d, 1H), 7.61-7.57 (m, 3H), 7.02-7.01 (m, 2H), 3.63 (d, 2H), 3.63-3.37 (m, 4H), 2.59-2.51 (m, 2H), 2.49-2.42 (m, 2H), 2.14 (d, 3H) | [M + H]⁺ = 360.10 | 3 |
| 44 | ¹H NMR (400 MHz, DMSO-$d_6$) δ 11.87 (s, 1H), 8.39 (d, 1H), 7.83 (d, 1H), 7.64-7.55 (m, 2H), 6.95 (dd, 1H), 6.85 (dd, 1H), 3.63 (s, 2H), 3.40 (t, 4H), 2.50-2.46 (m, 4H), 2.14 (d, 3H)<br>¹⁹F NMR(377 MHz, DMSO-$d_6$) δ −108.09 | [M + H]⁺ = 378.10 | 3 |
| 45 | ¹H NMR (400 MHz, DMSO-$d_6$) δ 11.85 (s, 1H), 8.40 (d, 1H), 7.75 (s, 1H), 7.69 (dd, 1H), 7.61 (d, 1H), 7.57 (dd, 1H), 7.12 (t, 1H), 3.65 (s, 2H), 3.23-3.14 (m, 4H), 2.59-2.51 (m, 6H), 1.18 (t, 3H)<br>¹⁹F NMR (282 MHz, DMSO-$d_6$) δ −119.88 | [M + H]⁺ = 392.10 | 3 |
| 46 | ¹H NMR (300 MHz, DMSO-$d_6$) δ 11.87 (s, 1H), 8.38 (d, 1H), 7.69 (dd, 1H), 7.63-7.53 (m, 2H), 7.42 (s, 1H), 7.12 (t, 1H), 3.70-3.54 (m, 2H), 3.25-3.14 (m, 4H), 2.61-2.52 (m, 4H), 2.19-2.09 (m, 1H), 1.03-0.92 (m, 2H), 0.88-0.78 (m, 2H)<br>¹⁹F NMR (377 MHz, DMSO-$d_6$) δ −119.88 | [M + H]⁺ = 404.20 | 16 |
| 50 | ¹H NMR (400 MHz, DMSO-$d_6$) δ 11.87 (s, 1H), 8.40 (d, 1H), 8.25 (d, 1H), 7.95-7.92 (m, 1H), 7.83 (s, 1H), 7.60 (d, 1H), 7.22 (d, 1H), 3.67 (s, 2H), 3.40-3.38 (m, 4H), 2.59-2.57 (m, 4H), 2.14 (d, 3H) | [M + H]⁺ = 385.15 | 3 |
| 51 | ¹H NMR (300 MHz, DMSO-$d_6$) δ 11.87 (s, 1H), 8.41 (d, 1H), 7.86-7.84 (m, 2H), 7.67-7.61 (m, 2H), 7.18 (d, 1H), 3.67 (s, 2H), 3.17-3.15 (m, 4H), 2.61-2.59 (m, 4H), 2.35 (s, 3H) | [M + H]⁺ = 394.05 | 3 |
| 52 | ¹H NMR (300 MHz, DMSO-$d_6$) δ 11.87 (s, 1H), 8.40 (s, 1H), 8.25 (d, 1H), 7.96-7.92 (m, 1H), 7.76 (s, 1H), 7.61 (s, 1H), 7.24 (d, 1H), 3.67 (s, 2H), 3.40-3.29 (m, 4H), 2.59-2.51 (m, 6H), 1.23-1.16 (m, 3H) | [M + H]⁺ = 399.20 | 3 |

TABLE 2-continued

Characterization Data

| Ex. | NMR | MS | Synthesized as described in Example |
|---|---|---|---|
| 53 | $^1$H NMR (300 MHz, DMSO-d$_6$) δ 11.88 (s, 1H), 8.40 (d, 1H), 8.02 (dd, 1H), 7.83 (d, 1H), 7.61 (d, 1H), 7.31(dd, 1H), 3.66 (s, 2H), 3.16 (t, 4H), 2.58 (t, 4H), 2.14 (d, 3H) $^{19}$F NMR (282 MHz, DMSO-D$_6$) δ −126.55, −126.64, −145.14, −145.23 | [M + H]$^+$ = 396.20 | 3 |
| 54 | $^1$H NMR (300 MHz, DMSO-d$_6$) δ 11.86 (s, 1H), 8.44-8.37 (m, 2H), 8.00 (dd, 1H), 7.75 (s, 1H), 7.61 (d, 1H), 3.74-3.65 (m, 4H), 3.63 (s, 2H), 2.60-2.51 (m, 6H), 1.18 (t, 3H) $^{19}$F NMR (282 MHz, DMSO-d$_6$) δ −127.14 | [M + H]$^+$ = 393.15 | 3 |
| 55 | $^1$H NMR (400 MHz, DMSO-d$_6$) δ 11.89 (s, 1H), 8.40 (d, 1H), 8.00 (d, 1H), 7.83(d, 1H), 7.66 (d, 1H), 7.61 (d, 1H), 3.67 (s, 2H), 3.18 (t, 4H), 2.59 (t, 4H), 2.14 (d, 3H) | [M + H]$^+$ = 395.00 | 3 |
| 56 | $^1$H NMR (400 MHz, DMSO-d$_6$) δ 11.86 (s, 1H), 8.49 (d, 1H), 8.40(d, 1H), 8.24 (dd, 1H), 7.75 (s, 1H), 7.62 (d, 1H), 3.65 (s, 2H), 3.55-3.45 (m, 4H), 2.60-2.52 (m, 6H), 1.18 (t, 3H) $^{19}$F NMR (400 MHz, DMSO-d$_6$) δ −139.11 | [M + H]$^+$ = 393.20 | 3 |
| 57 | $^1$H NMR (400 MHz, DMSO-d$_6$) δ 12.46 (s, 1H), 8.48 (d, 2H), 8.29 (s, 1H), 7.85 (dd, 1H), 7.70-7.67 (m, 1H), 6.93 (d, 1H), 3.69-3.65 (m, 6H). 2.49-2.45(m, 4H) | [M + H]$^+$ = 381.10 | 47 |
| 58 | $^1$H NMR (300 MHz, DMSO-d$_6$) δ 11.85 (s, 1H), 8.39 (d, 1H), 8.23 (dd, 1H), 7.83 (d, 1H), 7.62 (d, 1H), 6.95 (dd, 1H), 3.63 (s, 2H), 3.53-3.41 (m, 4H), 2.50-2.44 (m, 4H), 2.14 (d, 3H) $^{19}$F NMR (282 MHz, DMSO-d$_6$) δ −127.56, −127.64, −168.25, −168.33 | [M + H]$^+$ = 372.20 | 3 |
| 59 | $^1$H NMR (400 MHz, DMSO-d$_6$) δ 12.33 (s, 1H), 8.54 (d, 1H), 8.16 (s, 1H), 7.71 (d, 1H), 7.59 (s, 1H), 7.57 (s, 1H), 7.03 (s, 1H), 7.01 (s, 1H), 6.99 (t, 1H), 3.69 (s, 2H), 3.48-3.34 (m, 4H), 2.62-2.52 (m, 4H) $^{19}$F NMR (377 MHz, DMSO-d$_6$) δ −119.31 | [M + H]$^+$ = 396.10 | 48 |
| 61 | $^1$H NMR (300 MHz, DMSO-d$_6$) δ 12.45 (brs, 1H), 8.48 (d, J = 1.8 Hz, 1H), 8.28 (s, 1H), 7.90-7.87 (m, 1H), 7.68 (s, 1H), 7.55 (dd, J = 10.5, 8.1 Hz, 1H), 3.68 (s, 2H), 3.30-3.15 (m, 4H), 2.67-2.51 (m, 4H) $^{19}$F NMR (300 MHz, DMSO-d$_6$) δ −68.78. | [M + H]$^+$ = 399.15 | 47 |
| 62 | $^1$H NMR (300 MHz, DMSO-d$_6$) δ 12.33 (s, 1H), 8.53 (d, J = 1.8 Hz, 1H), 8.16 (s, 1H), 7.89 (dd, J = 8.1, 1.5 Hz, 1H), 7.70 (d, J = 1.8 Hz, 1H), 7.56 (dd, J = 10.5, 8.2 Hz, 1H), 6.98 (t, J = 54.4 Hz, 1H), 3.71(s, 2H), 3.30-3.28 (m, 4H), 2.58 (m, 4H) $^{19}$F NMR (282 MHz, DMSO-d$_6$) δ −68.78, −119.29. | [M − H]$^-$ = 413.05 | 48 |
| 63 | $^1$H NMR (300 MHz, DMSO-d$_6$) δ 12.33 (s, 1H), 8.54 (d, J = 1.8Hz, 1H), 8.48 (d, J = 2.3 Hz, 1H), 8.17 (d, J =2.0 Hz, 1H), 7.85 (dd, J = 9.1, 2.4 Hz, 1H), 7.71 (d, J = 1.8 Hz, 1H), 7.18-6.78 (m, 2H), 3.69-3.66 (m, 4H), 2.73-2.50 (m, 4H). $^{19}$F NMR(282 MHz, DMSO-d$_6$) δ −119.30 | [M + H]$^+$ = 399.15 | 48 |
| 64 | $^1$H NMR (400 MHz, DMSO-d$_6$) δ 11.83 (s, 1H), 8.95 (d, 1H), 8.39(d, 1H), 8.23 (dd, 1H), 7.75 (s, 1H), 7.63 (d, 1H), 7.54 (d, 1H), 3.62 (s, 2H), 2.93 (dd, 2H), 2.84-2.75 (m, 1H), 2.56-2.51 (m, 2H), 2.20-2.07 (m, 2H), 1.84-1.72 (m, 4H), 1.18 (t,3H) | [M + H]$^+$ = 374.3 | 3 |
| 65 | $^1$H NMR (300 MHz, DMSO-d$_6$) δ 11.85 (s, 1H), 8.41 (d, J = 1.7 Hz, 1H), 8.33 (s, 1H), 7.94 (s, 1H), 7.75 (s, 1H), 7.62 (s, 1H), 3.67 (s, 2H), 3.21-3.25 (m, 4H), 2.63-2.50 (m, 6H), 1.18 (t, J = 7.4 Hz, 3H) | [M + H]$^+$ = 409.20 | 3 |
| 66 | $^1$H NMR (400 MHz, DMSO-d$_6$) δ 12.45 (brs, 1H), 8.48 (d, J = 1.8 Hz, 1H), 8.28 (s, 1H), 7.70 (d, J = 1.8 Hz, 1H), 7.57 (d, J = 8.9 Hz, 2H), 7.01 (d, J = 8.6 Hz, 2H), 3.65 (s, 2H), 3.37-3.33 (m, 4H), 2.57-2.51 (m, 4H) | [M + H]$^+$ = 380.15 | 47 |
| 67 | $^1$H NMR (400 MHz, DMSO-d$_6$) δ 11.86 (s, 1H), 8.41 (d, J = 1.8 Hz, 1H), 7.75 (s, 1H), | [M + H]$^+$ = 394.20 | 3 |

TABLE 2-continued

Characterization Data

| Ex. | NMR | MS | Synthesized as described in Example |
|---|---|---|---|
|  | 7.71 (dd, J = 8.4, 3.1 Hz, 1H), 7.62 (d, J = 2.0 Hz, 1H), 7.50 (td, J = 8.7, 3.1 Hz, 1H), 7.22 (dd, J = 9.2, 4.7 Hz, 1H), 3.14-3.04 (m, 4H), 2.64-2.57 (m, 4H), 2.55-2.50 (m, 2H), 1.19 (t, J = 7.4 Hz, 3H).<br>$^{19}$F NMR (400 MHz, DMSO-$d_6$) δ −122.50 |  |  |
| 70 | $^1$H NMR (300 MHz, DMSO-$d_6$) δ 12.44 (s, 1H), 8.47 (d, J = 2.3 Hz, 1H), 7.84 (dd, J = 9.1, 2.4 Hz, 1H), 7.52 (d, J = 8.3 Hz, 1H), 7.29 (t, J = 7.7 Hz, 1H), 6.92 (d, J = 9.1 Hz, 1H), 3.74-3.62(m, 6H), 2.50-2.48 (m, 4H), 2.42 (s, 3H).<br>$^{19}$F NMR (282 MHz, DMSO-$d_6$) δ −135.46 | [M + H]$^+$ = 379.10 | 49 |
| 72 | $^1$H NMR (400 MHz, DMSO-$d_6$) δ 12.44 (s, 1H), 8.48 (d, J = 2.0 Hz, 1H), 7.85 (dd, J = 9.1, 2.4 Hz, 1H), 7.16 (d, J = 4.8 Hz, 1H), 6.93 (d, J = 9.3 Hz, 1H), 3.83-3.53 (m, 6H), 2.53-2.50 (m, 4H), 2.43 (s, 3H).<br>$^{19}$F NMR (377 MHz, DMSO-$d_6$) δ −150.02, −150.45 | [M + H]$^+$ = 397.15 | 49 |
| 73 | $^1$H NMR (400 MHz, DMSO-$d_6$) δ 12.45 (s, 1H), 8.00 (d, J = 8.2 Hz, 1H), 7.64 (d, J = 8.3 Hz, 1H), 7.52 (d, J = 8.3 Hz, 1H), 7.29 (t, J = 7.6 Hz, 1H), 3.71 (s, 2H), 3.22-3.17 (m, 4H), 2.64-2.57 (m, 4H), 2.41 (s, 3H).<br>$^{19}$F NMR(377 MHz, DMSO-$d_6$) δ −135.44 | [M + H]$^+$ = 413.05 | 49 |
| 74 | $^1$H NMR (400 MHz, DMSO-$d_6$) δ 12.45 (s, 1H), 7.98 (dd, J = 8.1, 1.4 Hz, 1H), 7.57-7.49 (m, 2H), 7.28 (t, J = 7.7 Hz, 1H), 3.69 (s, 2H), 3.29-3.22 (m, 4H), 2.60-2.55 (m, 4H), 2.41 (s, 3H).<br>$^{19}$F NMR (377 MHz, DMSO-$d_6$) δ −68.82, −135.47 | [M + H]$^+$ = 397.05 | 49 |
| 75 | $^1$H NMR (400 MHz, DMSO-$d_6$) δ 12.33 (s, 1H), 8.54 (d, J = 1.8 Hz, 1H), 8.16 (s, 1H), 7.71 (s, 1H), 7.60-7.58 (m, 2H), 7.13-6.83 (m, 2H), 3.72 (s, 2H), 3.00-2.90 (m, 4H), 2.60-2.55 (m, 4H), 2.26 (s, 3H).<br>$^{19}$F NMR (377 MHz, DMSO-$d_6$) δ −119.31 | [M + H]$^+$ = 410.10 | 48 |
| 76 | $^1$H NMR (300 MHz, DMSO-$d_6$) δ 12.53 (s, 1H), 8.56 (d, J = 1.8 Hz, 1H), 8.36 (s, 1H), 7.82-7.71 (m, 2H), 7.64 (dd, J = 8.4, 2.0 Hz, 1H), 7.20 (t, J = 8.8 Hz, 1H), 3.75 (s, 2H), 3.30-3.23 (m, 4H), 2.68-2.60 (m, 4H).<br>$^{19}$F NMR (282 MHz, DMSO-$d_6$) δ −119.88 | [M + H]$^+$ = 398.05 | 47 |
| 77 | $^1$H NMR (300 MHz, DMSO-$d_6$) δ 12.45 (brs, 1H), 8.49 (d, J = 1.8 Hz, 1H), 8.28 (s, 1H), 8.00 (d, J = 8.2 Hz, 1H), 7.68-7.64 (m, 2H), 3.70 (s, 2H), 3.24-3.12 (m, 4H), 2.68-2.54 (m, 4H) | [M + H]$^+$ = 415.10 | 47 |
| 78 | $^1$H NMR (400 MHz, DMSO-$d_6$) δ 11.87 (s, 1H), 8.39 (d, J = 1.8 Hz, 1H), 7.89 (dd, J = 8.1, 1.4 Hz, 1H), 7.83 (d, J = 1.6 Hz, 1H), 7.60 (d, J = 1.9 Hz, 1H), 7.55 (dd, J = 10.5, 8.2 Hz, 1H), 3.64 (s, 2H), 3.30-3.27 (m, 4H), 2.60-2.56 (m, 4H), 2.13 (d, J = 1.3 Hz, 3H).<br>$^{19}$F NMR (400 MHz, DMSO-$d_6$) δ −68.79 | [M + H]$^+$ = 379.20 | 3 |
| 79 | $^1$H NMR (400 MHz, DMSO-$d_6$) δ 11.93 (s, 1H), 8.48 (d, J = 2.4 Hz, 1H), 7.86-7.83 (m, 2H), 7.11 (s, 1H), 6.98-6.91 (m, 2H), 3.68 (t, J = 4.9 Hz, 4H), 3.67 (s, 2H), 2.47 (t, J = 5.0 Hz, 4H), 2.10 (d, J = 1.3 Hz, 3H).<br>$^{19}$F NMR (377 MHz, DMSO-$d_6$) δ −122.75. | [M + H]$^+$ = 378.15 | 71 |
| 80 | $^1$H NMR (300 MHz, DMSO-$d_6$) δ 12.34 (s, 1H), 8.55 (d, J = 1.8 Hz, 1H), 8.17 (s, 1H), 8.02 (s, 1H), 7.95 (dd, J = 8.4, 2.1 Hz, 1H), 7.70 (s, 1H), 7.40 (d, J = 8.6 Hz, 1H), 7.33-6.78 (m, 2H), 3.73 (s, 2H), 3.08-2.96 (m, 4H), 2.65-2.57 (m, 4H).<br>$^{19}$F NMR (282 MHz, DMSO-$d_6$) δ −109.85, −110.15 | [M + H]$^+$ = 446.15 | 48 |
| 81 | $^1$H NMR (300 MHz, DMSO-$d_6$): δ 12.32 (s, 1H), 8.54 (d, J = 1.8 Hz, 1H), 8.16 (s, 1H), 8.00 (d, J = 8.2 Hz, 1H), 7.75-7.62 (m, 2H), 6.98 (t, J = 54.5 Hz, 1H), 3.73 (s, 2H), | [M + H]$^+$ = 431.10 | 48 |

TABLE 2-continued

Characterization Data

| Ex. | NMR | MS | Synthesized as described in Example |
|---|---|---|---|
| | 3.26-3.10 (m, 4H), 2.61 (t, J = 4.7 Hz, 4H). $^{19}$F NMR (282 MHz, DMSO-$d_6$) δ −119.28 | | |
| 84 | $^1$H NMR (400 MHz, DMSO-$d_6$) δ 12.27 (s, 1H), 8.47 (d, J = 2.3 Hz, 1H), 7.84 (dd, J = 9.1, 2.4 Hz, 1H), 7.65 (d, J = 8.2 Hz, 1H), 7.26-7.22 (m, 2H), 6.92 (d, J = 9.1 Hz, 1H), 3.67 (t, J = 5.0 Hz, 4H), 3.59 (s, 2H), 2.45 (t, J = 5.1 Hz, 4H), 2.39 (s, 3H) | $[M + H]^+ =$ 361.15 | 49 |

Example A: Cell Growth Inhibition Assay

Cell proliferation was measured through the cell viability assay using DLD-1 BRCA2(−/−) and parental isogenic pair and MDA-MB-436 (mutated BRCA1) cell lines. The Cell-Titer-Glo (CTG) based cell viability assay is designed to determine the number of viable cells in the culture because of compound effect, by quantifying ATP, which indicates the presence of metabolically active cells.

DLD-1 BRCA2(−/−) and parental isogenic pair were cultured in RPMI 1640 supplemented with 1000 fetal bovine serum (FBS), and MDA-NM-436 cells were cultured in DMEM supplemented with 10% FBS. Both were cultured at 37° C. with 500 $CO_2$. Invention compounds were distributed to the 384 well plate (Corning, 3764) using Echo acoustic liquid handler to form a 1:3 serially diluted final concentration with top dose of 10 or 30 μM. The cells were seeded into the plate in the density of 50 cells/well (DLD-1 parental), 200 cells/well (DLD-1 BRCA2−/−), or 500 cells/well (MDA-MB-436). After a short spun, the cells were cultured in a well moisturized incubator at 37° C. with 5% $CO_2$ for 7 days without disturbance. The cell viability was measured by CellTiter Glo 2.0 assay kit (Promega, G9243), and growth inhibition rate was calculated and plotted against final compound concentration, and the data were fitted in Xfit to generate $IC_{50}$ values.

Example B: Biochemical (FP) Assay

Assays based on fluorescent polarization (FP) have been widely utilized in drug discovery due to the homogenous format, robust performance and lack of interference seen in other assays. Compounds were characterized using an assay measuring the displacement of a commercially available fluorescently labeled PARP 1/2 inhibitor (PARPi-FL, Tocris Biosciences, #6461) as exemplified in assays performed in WO2014/064149 and WO2021/013735A1. The assay was performed utilizing the following method:

Compounds were dissolved in DMSO an Echo550 liquid handler was utilized to make serial dilations in the desired concentration range in Optiplate-384F plates. 100% DMSO was used for the high (with protein) and low (without protein) control samples. 20 nL of compound or DMSO alone was added to individual assay plate wells.

PARP1 and PARP2 protein were expressed, purified, and diluted in assay buffer containing 50 mM Tris pH 8.0, 0.001% Triton X-100, 10 mM $MgCl_2$, 150 mM NaCl to a final concentration of 20 nM. The PARPi-FL was then added at a final concentration of 3 nM.

The assay plate was centrifuged at 1000 rpm for 1 min and incubated for 4 h at room temperature.

The fluorescent polarization was read using an Envision plate reader using the following settings:
Excitation filter —FITC FP 480-Ex Slot 3
Emission filter —FITC FP P-pol 535-Em Slot4
2nd Emission filter —FITC FP S-pol 535-Em Slot 3
Mirror module —FITC FP Dual Enh-Slot 1
The inhibition rate was calculated using the percentage of permuted Mahalanobis distances greater than the control samples (mP value) following the equation below:

$mP_c$: the mP value of compounds
$mP_L$: the mP value of Low controls
$mP_H$: the mP value of High controls $$\text{Inhibition (\%)} = \left(1 - \frac{mP_C - mP_L}{mP_H - mP_L}\right) \times 100\%$$

XLFit (equation 201) is used to calculate a reported $IC_{50}$ for each compound.

The data from examples A and B are provided in Table 3.

TABLE 3

| Ex. | FP PARP1 pIC50 | FP PARP2 pIC50 | DLD-1 BRCA2(−/−) pEC50 | DLD-1 parental pEC50 | MDA-MB-436 pEC50 |
|---|---|---|---|---|---|
| 1 | 7.8 | 4.0 | 7.2 | | 7.2 |
| 2 | 7.3 | 5.1 | 8.8 | | 8.9 |
| 3 | 8.4 | 5.1 | 8.5 | <4.5 | 8.6 |
| 4 | 8.4 | 5.3 | 8.7 | | 8.7 |
| 5 | 8.5 | <4.0 | 8.4 | | 8.4 |
| 6 | 8.3 | 5.3 | 8.6 | <4.5 | 8.6 |
| 7 | 7.6 | <4.0 | 8.2 | | 8.2 |
| 8 | 7.8 | <4.0 | 8.3 | | 8.5 |
| 9 | 8.2 | 5.8 | 9.3 | | 9.3 |
| 10 | 8.3 | 5.3 | 9.1 | | 9.1 |
| 11 | 8 | 4.1 | 7.7 | | 7.4 |
| 12 | 8.1 | 4 | 8 | | 8 |
| 13 | 8.3 | <4.0 | 8.3 | | 8.4 |
| 14 | 8.3 | 5.2 | 7.2 | | 7.3 |
| 15 | 8.3 | 5 | 8.1 | | 8.3 |
| 16 | 8.5 | 5.6 | 8 | | 8 |
| 17 | 8.4 | 5.7 | 8.6 | | 8.7 |
| 18 | 8.3 | <4.0 | 8.5 | | 8.6 |
| 19 | 8.2 | <4.0 | 6.7 | | 6.8 |
| 20 | 8.3 | 5.6 | 7.3 | | 7.4 |
| 21 | 8.3 | 5.9 | 8.1 | | 7.9 |
| 22 | 8.1 | 4.9 | 6.9 | | 6.8 |
| 23 | 7.4 | <4.0 | 7 | | 6.7 |
| 24 | 8 | <4.0 | 7.1 | | 7.3 |
| 25 | 8.2 | <4.0 | 7.5 | | 7.3 |
| 26 | <7.0 | <4.0 | <6.0 | | <6.0 |
| 27 | 8.1 | <4.0 | 7.9 | | 7.4 |
| 28 | <7.0 | <4.0 | 7.2 | | 7.2 |

TABLE 3-continued

| Ex. | FP PARP1 pIC50 | FP PARP2 pIC50 | DLD-1 BRCA2(−/−) pEC50 | DLD-1 parental pEC50 | MDA-MB-436 pEC50 |
|---|---|---|---|---|---|
| 29 | 8.2 | <4.0 | 7.2 | | 7.1 |
| 30 | 7.8 | <4.0 | <6.0 | | <6.0 |
| 31 | 8.2 | <4.0 | 7.8 | | 8.2 |
| 32 | 8.4 | <4.0 | 7.9 | | 8.1 |
| 33 | 8.6 | 5.2 | 8.5 | | 8.6 |
| 34 | 8 | 4.3 | 7.3 | | 7.4 |
| 35 | 8 | 4.2 | 8.5 | | 8.6 |
| 36 | 8.3 | 5.7 | 8.9 | | 9 |
| 37 | 8.5 | <4.0 | 8.5 | | 8.8 |
| 38 | 8.3 | 6.3 | 9.2 | | 9.3 |
| 39 | 8.2 | <4.0 | 8.7 | | 8.9 |
| 40 | 8.2 | 4.9 | 9 | | 9.1 |
| 41 | 7.9 | 5.7 | 9.1 | | 9 |
| 42 | 7.3 | 6.5 | 8.7 | | 9 |
| 43 | 8.3 | 5.2 | 8.5 | | 8.6 |
| 44 | 8.0 | 5.5 | 8.6 | | 8.8 |
| 45 | 7.8 | 4.9 | 8.9 | | 9 |
| 46 | 8.0 | 4.0 | 8.7 | | 8.8 |
| 47 | 8.0 | 4.0 | 8.6 | | 8.1 |
| 48 | 8.4 | 5.9 | 9 | | 9 |
| 49 | 8.0 | 4.0 | 8 | | 7.9 |
| 50 | 7.6 | 4.0 | 8.7 | | 8.8 |
| 51 | 7.7 | 4.0 | 8.4 | | 8.6 |
| 52 | 7.6 | 4.9 | 9.1 | | 9.2 |
| 53 | 7.9 | 4.0 | 8.2 | | 8.3 |
| 54 | 7.2 | 4.0 | 7.2 | | 7.1 |
| 55 | 8.1 | <4.0 | 8.9 | | 9 |
| 56 | 7.8 | 4.0 | 7 | | 7.2 |
| 57 | 8.3 | 4.3 | 8.6 | 4.7 | 8.7 |
| 58 | 7.9 | 4.8 | 8.1 | | 8.1 |
| 59 | 8.2 | <4.0 | 8.9 | | 9 |
| 60 | 8.2 | 5.7 | 8.8 | | 8.9 |
| 61 | 8.2 | <4.0 | 8.5 | | 8.7 |
| 62 | 7.2 | 4.0 | 8.8 | | 8.9 |
| 63 | 7.8 | 6.1 | 8.8 | | 8.9 |
| 64 | 8.3 | <4.0 | 8.3 | | 8.7 |
| 65 | 7.0 | 4.0 | 8.5 | | 8.6 |
| 66 | 8.3 | <4.0 | 8.7 | | 8.8 |
| 67 | 7.8 | 4.6 | 8.8 | | 8.8 |
| 68 | 7.9 | 4.1 | 7.4 | | 7.6 |
| 69 | 8.0 | 4.4 | 7.4 | | 7.8 |
| 70 | 8.0 | 4.0 | 7.6 | | 7.5 |
| 71 | 8.0 | 4.0 | 7.9 | | 7.8 |
| 72 | 7.8 | 4.0 | 7.2 | | 7.4 |
| 73 | 7.6 | 4.0 | 7.7 | | 7.8 |
| 74 | 7.8 | 4.0 | 7.7 | | 7.5 |
| 75 | 7.6 | 4.0 | 9.2 | | 9.3 |
| 76 | 7.2 | 4.0 | 8.3 | | 8.3 |
| 77 | 8.2 | <4.0 | 9.1 | | 9.1 |
| 78 | 8.2 | <4.0 | 8.4 | | 8.5 |
| 79 | 8.0 | 4.9 | 8.1 | | 8.3 |
| 80 | 7.8 | 4.0 | 8.9 | | 9 |
| 81 | 8.0 | 4.0 | 9.2 | | 9.2 |
| 82 | 7.5 | 4.0 | 7 | | 7.4 |
| 83 | 8.0 | 4.0 | 8 | | 8.2 |
| 84 | 8.0 | 4.3 | 8.2 | | 8.1 |

Example C: In Vitro Human Transporter Efflux

Madin-Darby canine kidney (MDCKII) cells expressing MDR1 and BCRP were seeded onto Corning HITS Transwell® 96-well polycarbonate permeable (0.4 m pore) supports at a density of 545,000 cells/cm2. Cells were incubated for 4-8 days prior to assay, and monolayer integrity was assessed by measuring transepithelial electrical resistance (TEER). Test and reference compounds were diluted with the transport buffer (HBSS HEPES pH7.4) to concentrations of 10 and 1 µM, respectively. The final organic solvent concentration was 0.5% (v/v). Bidirectional (apical-to-basolateral and basolateral-to-apical) flux of the test and reference compounds was determined over a 2-hour incubation at 37° C. and 5% CO2 with a relative humidity of 95%. At the end of the incubation, samples from the apical and basolateral side were taken and then precipitated with acetonitrile containing internal standard. After centrifugation at 3200×g, supernatants were diluted 1:1 (v/v) with water and subjected to analysis via HPLC-MS/MS. The integrity The apparent permeability (Papp, units of ×10−6 cm/s) was calculated using the following equation:

$$Papp = (dQ/dt)/(A \times D0)$$

Where dQ/dt was the rate of drug transport (pmol/s), A was the surface area of the membrane (0.143 cm$^2$), and D0 was the initial donor concentration (nM or pmol/cm3).

$$\text{Efflux ratio} = Papp(B \to A)/Papp(A \to B)$$

Where Papp(B→A) is the apparent permeability in the basolateral-to-apical direction, and Papp(A→B) is the apparent permeability in the apical-to-basolateral direction Example D: In Vivo Determination of Rat Kp,uu Determination of Fraction Unbound in Plasma (Pu)

The equilibrium dialysis method was used to investigate the in vitro binding of test articles and reference compounds to plasma proteins. Plasma samples containing 5 µM test article or blank dialysis buffer solution (PBS, pH 7.4) were added to separate chambers of the dialysis wells of the High Throughput equilibrium Dialysis (HTD) device. The dialysis plate was sealed and placed in an incubator at 37° C. with 5% $CO_2$ with shaking at approximately 100 rpm for 6 hours. All experiments were performed in duplicate. Ketoconazole (5 µM) was used as the reference compound. After incubation, the seal was removed, and 50 µL of post-dialysis samples were pipetted from both buffer and plasma chambers into fresh 96-well plates. Samples were equimatrilyzed by either addition of blank plasma to buffer samples or the addition of blank buffer to plasma samples. Subsequently, 400 µL (4 volumes) of acetonitrile containing internal were added to all samples to precipitate proteins prior to analysis by UPLC-MS/MS to determine the relative concentrations of test articles. The unbound fractions in plasma were calculated using the concentrations of test articles in buffer and plasma samples according to the following equation:

$$\text{Percentage unbound (\%)} = \frac{\text{Analyte to } IS \text{ Peak Area Ratio (buffer chamber)}}{\text{Analyte to } IS \text{ Peak Area Ratio (plasma chamber)}} \times 100$$

Determination of Fraction Unbound in Brain Homogenate (Bu)

The equilibrium dialysis method was used to investigate the in vitro binding of test articles and reference compounds to rodent brain homogenate. Brains collected from naïve animals were weighed and homogenized in 4 volumes of PBS, pH 7.4. Brain homogenate samples containing 1 µM test article or blank dialysis buffer solution (PBS, pH 7.4) were added to separate chambers of the dialysis wells of the High Throughput equilibrium Dialysis (HTD) device. The dialysis plate was sealed and placed in an incubator at 37° C. with 5% $CO_2$ with shaking at approximately 100 rpm for 6 hours. All experiments were performed in duplicate. Telmisartan (5 μM) was used as the reference compound. After incubation, the seal was removed, and 50 μL of post-dialysis samples were pipetted from both buffer and brain homogenate chambers into fresh 96-well plates. Samples were equimatrilyzed by either addition of blank homogenate to buffer samples or the addition of blank buffer to homogenate samples. Subsequently, 400 μL (4 volumes) of acetonitrile containing internal were added to all samples to precipitate proteins prior to analysis by UPLC-MS/MS to determine the relative concentrations of test articles. The unbound fractions in diluted brain homogenate were calculated using the concentrations of test articles in buffer and homogenate samples according to the following equation:

$$\text{Percentage unbound homogenate (\%)} = \frac{\text{Analyte to } IS \text{ Peak Area Ratio (buffer chamber)}}{\text{Analyte to } IS \text{ Peak Area Ratio (homogenate chamber)}} \times 100$$

Correction to percentage unbound in undiluted brain was achieved with the following equation:

$$\text{Percentage unbound brain (\%)} = 100 \times \frac{1/5}{\left(\frac{1}{\text{Percentage unbound homogenate}/100} - 1\right) + 1/5}$$

Determination of the Drug Brain-to-Plasma Partition Coefficient (Kp) and Drug Unbound Kp (Kp,uu) in Rat Compounds were formulated either individually or in a cassette (as a mixture) at a concentration of 0.1 mg/mL/compound in sterile water containing 0.5% (w/v) methylcellulose 400 cP and administered to male Sprague-Dawley rats via oral gavage at a dose volume of 10 mL/kg. One animal was sacrificed at each of the following time points: 0.5, 1, 2, 4, 8, and 24 hours post-dose, and brain and blood samples were collected. Plasma was prepared from blood via refrigerated centrifugation, and plasma samples were stored frozen at −80° C. until bioanalysis. Brain samples were rinsed with saline to remove residual blood and blotted dry with a paper wipe. Brain samples were then weighed and homogenized with 3 volumes (v/w) of water and stored frozen at −80° C. until bioanalysis.

Prior to bioanalysis, plasma and brain samples were extracted with 4 volumes of acetonitrile containing internal standard and centrifuged for 15 minutes. Supernatants were diluted with 2 volumes of water and injected for analysis via HPLC-MS/MS. Plasma and brain homogenate drug concentrations were determined against calibration curves generated by spiking blank rat plasma or brain homogenate with drug across an appropriate concentration range. The brain homogenate concentration was corrected for the homogenization buffer dilution factor yielding total brain drug concentrations.

The brain-to-plasma partition coefficient (Kp) was determined for each compound, calculated as: AUCbrain:AUCplasma, provided tlast was identical in each matrix. If the drug concentration versus time profile for one matrix fell below the lower limit of quantification at a time point earlier than in the other matrix, then the brain Kp was calculated as the average of the ratios of total brain drug concentration to total plasma drug concentration measured at each time point where drug concentrations in both matrices were quantifiable.

The Kp,uu was then calculated from the Kp using the following equation: Kp,uu=Kp*(fraction unbound in brain homogenate/fraction unbound in plasma).

The data from examples C and D are provided in Table 4.

TABLE 4

| Example | MDCK-MDR1 Papp AB | MDCK-MDR1 Papp BA | MDCK-MDR1 Ratio | BCRP Papp AB | BCRP Papp BA | BCRP Ratio | rat Kp,uu |
|---|---|---|---|---|---|---|---|
| 3 | 11.5 | 36.0 | 3.1 | 22.9 | 25.5 | 1.1 | 0.021 |
| 4 | 21.8 | 27.8 | 1.3 | 17.0 | 22.3 | 1.3 | 0.71 |
| 5 | 12.6 | 10.6 | 0.9 | 6.4 | 6.4 | 1.0 | |
| 6 | 28.4 | 41.5 | 1.5 | 30.4 | 28.5 | 0.9 | 0.48 |
| 9 | 18.1 | 22.5 | 1.3 | | | | |
| 10 | 18.7 | 33.7 | 1.8 | 27.8 | 21.7 | 0.8 | |
| 11 | 12.7 | 36.2 | 2.9 | 19.9 | 19.6 | 1.0 | |
| 15 | 24.2 | 33.3 | 1.4 | 23.4 | 22.8 | 1.0 | |
| 18 | 21.4 | 24.0 | 1.1 | 24.2 | 22.4 | 0.9 | 0.38 |
| 36 | 7.1 | 11.4 | 1.6 | | | | |
| 42 | 7.0 | 11.0 | 1.6 | | | | |
| 43 | 20.2 | 24.5 | 1.2 | | | | 0.35 |
| 44 | 11.4 | 20.1 | 1.8 | | | | |
| 48 | 12.1 | 25.2 | 2.1 | | | | 0.24 |
| 55 | 9.5 | 29.3 | 3.1 | | | | 0.072 |
| 57 | 13.4 | 28.0 | 2.1 | 14.2 | 15.2 | 1.1 | 0.42 |
| 59 | 9.9 | 10.9 | 1.1 | | | | 0.58 |
| 60 | 4.4 | 11.6 | 2.7 | | | | |

What is claimed is:
1. A compound which is:

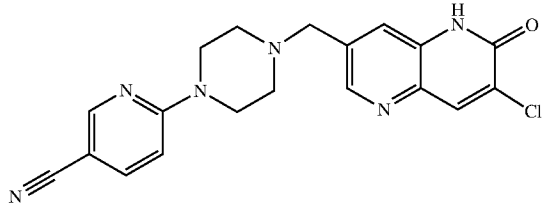 [SMILES: N#Cc1ccc(N2CCN(Cc3cnc4cc(Cl)c(=O)[nH]c4c3)CC2)nc1]

or a pharmaceutically acceptable salt thereof.
2. A pharmaceutical composition comprising a compound of claim 1, or a pharmaceutically acceptable salt thereof, and a pharmaceutically acceptable excipient.

* * * * *